(12) United States Patent
Murray

(10) Patent No.: US 9,849,213 B2
(45) Date of Patent: Dec. 26, 2017

(54) METHODS AND PRODUCTS FOR TISSUE REPAIR

(71) Applicant: Children's Medical Center Corporation, Boston, MA (US)

(72) Inventor: Martha M. Murray, Sherborn, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 15/082,235

(22) Filed: Mar. 28, 2016

(65) Prior Publication Data

US 2016/0206779 A1    Jul. 21, 2016

Related U.S. Application Data

(63) Continuation of application No. 13/862,554, filed on Apr. 15, 2013, now Pat. No. 9,308,242, which is a continuation of application No. 12/412,692, filed on Mar. 27, 2009, now abandoned, which is a continuation of application No. PCT/US2007/021009, filed on Sep. 28, 2007.

(60) Provisional application No. 60/847,743, filed on Sep. 28, 2006.

(51) Int. Cl.
| | |
|---|---|
| *A61K 8/65* | (2006.01) |
| *A61L 27/24* | (2006.01) |
| *A61K 38/39* | (2006.01) |
| *A61K 45/06* | (2006.01) |
| *A61L 27/54* | (2006.01) |
| *A61L 27/56* | (2006.01) |
| *A61L 27/58* | (2006.01) |
| *A61K 31/401* | (2006.01) |
| *A61K 35/17* | (2015.01) |
| *A61K 35/19* | (2015.01) |
| *A61L 27/36* | (2006.01) |
| *A61L 27/50* | (2006.01) |

(52) U.S. Cl.
CPC ............ *A61L 27/24* (2013.01); *A61K 31/401* (2013.01); *A61K 35/17* (2013.01); *A61K 35/19* (2013.01); *A61K 38/39* (2013.01); *A61K 45/06* (2013.01); *A61L 27/3616* (2013.01); *A61L 27/3662* (2013.01); *A61L 27/50* (2013.01); *A61L 27/54* (2013.01); *A61L 27/56* (2013.01); *A61L 27/58* (2013.01); *A61L 2300/252* (2013.01); *A61L 2300/406* (2013.01); *A61L 2300/432* (2013.01); *A61L 2300/602* (2013.01); *A61L 2300/64* (2013.01); *A61L 2400/06* (2013.01); *A61L 2430/10* (2013.01)

(58) Field of Classification Search
None
See application file for complete search history.

(56) References Cited

U.S. PATENT DOCUMENTS

| | | | |
|---|---|---|---|
| 2,127,903 | A | 8/1938 | Bowen |
| 3,176,316 | A | 4/1965 | Bodell |
| 3,373,906 | A | 3/1968 | De Hart et al. |
| 3,587,982 | A | 6/1971 | Campbell |
| 3,738,535 | A | 6/1973 | Nicholls |
| 3,774,604 | A | 11/1973 | Danielsson |
| 3,797,499 | A | 3/1974 | Schneider |
| 4,069,814 | A | 1/1978 | Clemens |
| 4,186,448 | A | 2/1980 | Brekke |
| 4,265,618 | A | 5/1981 | Herskovitz et al. |
| 4,458,678 | A | 7/1984 | Yannas et al. |
| 4,467,806 | A | 8/1984 | Bhiwandiwala et al. |
| 4,578,067 | A | 3/1986 | Cruz |
| 4,585,458 | A | 4/1986 | Kurland |
| 4,753,536 | A | 6/1988 | Spehar et al. |
| 4,808,184 | A | 2/1989 | Tepic |
| 4,808,570 | A | 2/1989 | Michaeli |
| 4,846,835 | A | 7/1989 | Grande |
| 4,851,513 | A | 7/1989 | Devore et al. |
| 4,894,063 | A | 1/1990 | Nashef |
| 4,932,942 | A | 6/1990 | Maslanka |
| 4,955,893 | A | 9/1990 | Yannas et al. |
| 4,959,058 | A | 9/1990 | Michelson |
| 4,973,321 | A | 11/1990 | Michelson |
| 5,007,934 | A | 4/1991 | Stone |
| 5,037,396 | A | 8/1991 | Streeter |
| 5,078,744 | A | 1/1992 | Chvapil |
| 5,119,669 | A | 6/1992 | Silvis et al. |
| 5,152,462 | A | 10/1992 | Evans |
| 5,171,273 | A | 12/1992 | Silver et al. |
| 5,206,023 | A | 4/1993 | Hunziker |
| 5,275,826 | A | 1/1994 | Badylak et al. |

(Continued)

FOREIGN PATENT DOCUMENTS

| | | |
|---|---|---|
| EP | 0295721 A2 | 12/1988 |
| EP | 0445951 A2 | 9/1991 |

(Continued)

OTHER PUBLICATIONS

Kliment et al., A novel method for accurate collagen and biochemical assessment of pulmonary tissue utilizing one animal, Int J Clin Exp Pathol. Apr. 30, 2011; 4(4):349-355.*
Neuman and Logan, The determination of hydroxyproline. J Biol Chem. May 1950; 184(1):299-306.*
Stenzel, Annu. Rev. Biophys. Bioeng. 1974.3:231-253.*
U.S. Appl. No. 14/765,064, filed Jul. 31, 2015, Murray.
U.S. Appl.No. 15/066,482, filed Mar. 10, 2016, Murray et al.
U.S. Appl. No. 13/461,269, filed May 1, 2012, Murray.

(Continued)

*Primary Examiner* — Satyanarayana R Gudibande
(74) *Attorney, Agent, or Firm* — Wolf, Greenfield & Sacks, P.C.

(57) ABSTRACT

Methods and devices for the repair of articular tissue using collagen material are provided. Compositions of collagen material and related kits are also provided.

9 Claims, 21 Drawing Sheets

(56) References Cited

U.S. PATENT DOCUMENTS

| | | |
|---|---|---|
| 5,281,422 A | 1/1994 | Badylak et al. |
| 5,380,087 A | 1/1995 | Haber et al. |
| 5,436,135 A | 7/1995 | Tayot et al. |
| 5,455,833 A | 10/1995 | Herre et al. |
| 5,467,786 A | 11/1995 | Allen et al. |
| 5,503,616 A | 4/1996 | Jones |
| 5,522,840 A | 6/1996 | Krajicek |
| 5,556,429 A | 9/1996 | Felt |
| 5,595,621 A | 1/1997 | Light et al. |
| 5,652,077 A | 7/1997 | Obinata |
| 5,655,546 A | 8/1997 | Halpern |
| 5,681,353 A | 10/1997 | Li et al. |
| 5,713,374 A | 2/1998 | Pachence et al. |
| 5,749,895 A | 5/1998 | Sawyer et al. |
| 5,810,884 A | 9/1998 | Kim |
| 5,897,591 A | 4/1999 | Kobayashi |
| 5,902,741 A | 5/1999 | Purchio et al. |
| RE36,370 E | 11/1999 | Li |
| 6,045,569 A | 4/2000 | Kensey et al. |
| 6,080,192 A | 6/2000 | Demopulos et al. |
| 6,087,113 A | 7/2000 | Caplan et al. |
| 6,096,309 A | 8/2000 | Prior et al. |
| 6,117,425 A | 9/2000 | MacPhee et al. |
| 6,129,757 A | 10/2000 | Weadock |
| 6,139,520 A | 10/2000 | McCrory et al. |
| 6,153,292 A | 11/2000 | Bell et al. |
| 6,171,610 B1 | 1/2001 | Vacanti et al. |
| 6,176,880 B1 | 1/2001 | Plouhar et al. |
| 6,214,049 B1 | 4/2001 | Gayer et al. |
| 6,234,795 B1 | 5/2001 | Fischer |
| 6,280,474 B1 | 8/2001 | Cassidy et al. |
| 6,309,372 B1 | 10/2001 | Fischer et al. |
| 6,365,149 B2 | 4/2002 | Vyakarnam et al. |
| 6,454,129 B1 | 9/2002 | Green |
| 6,472,210 B1 | 10/2002 | Holy et al. |
| 6,629,997 B2 | 10/2003 | Mansmann et al. |
| 6,689,153 B1 | 2/2004 | Skiba |
| 6,699,214 B2 | 3/2004 | Gellman |
| 6,946,003 B1 | 9/2005 | Wolowacz et al. |
| 6,964,685 B2 | 11/2005 | Murray et al. |
| 6,971,787 B2 | 12/2005 | Botrie et al. |
| 6,989,034 B2 | 1/2006 | Hammer et al. |
| 7,119,062 B1 | 10/2006 | Alvis et al. |
| 7,148,209 B2 | 12/2006 | Hoemann et al. |
| 7,156,880 B2 | 1/2007 | Evans et al. |
| 7,250,057 B2 | 7/2007 | Forsberg |
| 7,335,220 B2 | 2/2008 | Khosravi et al. |
| 7,652,077 B2 | 1/2010 | Cook et al. |
| 7,838,630 B2 | 11/2010 | Murray et al. |
| 7,901,461 B2 | 3/2011 | Harmon et al. |
| 8,002,813 B2 | 8/2011 | Scarborough et al. |
| 8,137,686 B2 | 3/2012 | Kladakis et al. |
| 8,308,681 B2 | 11/2012 | Slocum et al. |
| 8,642,735 B2 | 2/2014 | Murray et al. |
| 9,308,242 B2 * | 4/2016 | Murray .................. A61K 38/39 |
| 2002/0022884 A1 | 2/2002 | Mansmann |
| 2002/0123805 A1 | 9/2002 | Murray et al. |
| 2002/0161450 A1 | 10/2002 | Doi et al. |
| 2002/0183845 A1 | 12/2002 | Mansmann et al. |
| 2003/0012805 A1 | 1/2003 | Chen et al. |
| 2003/0078659 A1 | 4/2003 | Yang |
| 2003/0147935 A1 | 8/2003 | Binette et al. |
| 2003/0163144 A1 | 8/2003 | Weadock et al. |
| 2003/0167053 A1 | 9/2003 | Taufig |
| 2004/0059416 A1 | 3/2004 | Murray et al. |
| 2004/0078077 A1 | 4/2004 | Binette et al. |
| 2004/0170664 A1 | 9/2004 | Spector et al. |
| 2004/0243235 A1 | 12/2004 | Goh et al. |
| 2004/0258729 A1 | 12/2004 | Czernuszka et al. |
| 2004/0262332 A1 | 12/2004 | Pauser et al. |
| 2004/0267362 A1 | 12/2004 | Hwang et al. |
| 2005/0027307 A1 | 2/2005 | Schwartz et al. |
| 2005/0129730 A1 | 6/2005 | Pang et al. |
| 2005/0183731 A1 | 8/2005 | Hunter et al. |
| 2005/0230422 A1 | 10/2005 | Muller et al. |
| 2005/0261736 A1 | 11/2005 | Murray et al. |
| 2008/0195205 A1 | 8/2008 | Schwartz |
| 2009/0143765 A1 | 6/2009 | Slocum et al. |
| 2009/0254104 A1 | 10/2009 | Murray |
| 2009/0306776 A1 | 12/2009 | Murray |
| 2011/0027338 A1 | 2/2011 | Murray et al. |
| 2011/0306555 A1 | 12/2011 | Murray et al. |
| 2012/0201896 A1 | 8/2012 | Murray et al. |
| 2012/0283831 A1 | 11/2012 | Murray |
| 2013/0231609 A1 | 9/2013 | Slocum et al. |
| 2013/0273017 A1 | 10/2013 | Murray |
| 2014/0134249 A1 | 5/2014 | Murray et al. |
| 2014/0369984 A1 | 12/2014 | Murray et al. |
| 2015/0367030 A1 | 12/2015 | Murray |
| 2016/0263279 A1 | 9/2016 | Murray et al. |

FOREIGN PATENT DOCUMENTS

| | | |
|---|---|---|
| GB | 2106794 | 4/1983 |
| WO | WO 85/00511 | 2/1985 |
| WO | WO 92/13565 A1 | 8/1992 |
| WO | WO 93/11723 A1 | 6/1993 |
| WO | WO 93/21857 A1 | 11/1993 |
| WO | WO 95/25550 A1 | 9/1995 |
| WO | WO 99/40771 A2 | 8/1999 |
| WO | WO 00/74760 A2 | 12/2000 |
| WO | WO 02/067812 A2 | 9/2002 |
| WO | WO 03/105737 A1 | 12/2003 |
| WO | WO 2004/078134 A2 | 9/2004 |
| WO | WO 2008/036393 A1 | 3/2008 |
| WO | WO 2008/109407 A2 | 9/2008 |
| WO | WO 2008/109807 A2 | 9/2008 |
| WO | WO 2010/048418 A1 | 4/2010 |
| WO | WO 2010/084481 A1 | 7/2010 |
| WO | WO 2010/108237 A1 | 9/2010 |

OTHER PUBLICATIONS

U.S. Appl. No. 13/862,554, filed Apr. 15, 2013, Murray.

U.S. Appl. No. 14/376,212, filed Aug. 1, 2014, Murray.

PCT/US2014/014141, date of mailing May 13, 2014, International Search Report and Written Opinion.

PCT/US2014/014141, date of mailing Aug. 13, 2015, International Preliminary Report on Patentability.

PCT/US2002/023885, date of mailing Mar. 11, 2004, International Preliminary Examination Report.

PCT/US2002/023885, date of mailing Apr. 4, 2003, International Search Report.

PCT/US2002/023885, date of mailing Jun. 26, 2003, Written Opinion.

EP 06720499.0, date of mailing Jul. 16, 2009, Extended European Search Report.

PCT/US2006/004445, date of mailing Jul. 1, 2008, International Search Report and Written Opinion.

PCT/US2006/004445, date of mailing Feb. 26, 2009, International Preliminary Report on Patentability.

PCT/US2007/001908, date of mailing Oct. 31, 2007, International Search Report and Written Opinion.

PCT/US2007/001908, date of mailing Aug. 7, 2008, International Preliminary Report on Patentability.

PCT/US2007/021009, date of mailing Sep. 8, 2009, Invitation to Pay Additional Fees.

PCT/US2007/021009, date of mailing Dec. 22, 2009, International Search Report and Written Opinion.

PCT/US2007/021009, date of mailing Jan. 21, 2010, International Preliminary Report on Patentability.

EP 13743583.0, date of mailing Sep. 17, 2015, Extended European Search Report.

PCT/US2013/024467, date of mailing Apr. 29, 2013, International Search Report and Written Opinion.

PCT/US2013/024467, date of mailing Aug. 14, 2014, International Preliminary Report on Patentability.

[No Author Listed] Guidance document for testing biodegradable polymer implant devices, Division of General and Restorative Devices, Center for Devices and Radiological Health, U.S. Food and Drug Administration (Apr. 20, 1996).

(56) References Cited

OTHER PUBLICATIONS

Al-Munajjed et al., Development of a collagen calcium-phosphate scaffold as a novel bone graft substitute. Stud Health Technol Inform. 2008;133:11-20.
Anseth et al., "Polymerizable degradable plyanhydrides with osteocompatibility," 17(2) Nature Biotechnol. 156-159 (Feb. 1999).
Arendt et al., "Knee injury patterns among men and women in collegiate basketball and soccer," 23(6) Am. J. Sports Med. 694-701 (1995).
Buck, "Regeneration of Tendon," 66(1) J. Pathol. Bacteriol. 1-18 (1953).
Chamberlain et al., "Early peripheral nerve healing in collagen and silicone tube implants: myofibroblasts and the cellular response," 19 Biomaterials 1393-1403 (1998).
Chamberlain, "Collagen-GAG Substrate Enhances the Quality of Nerve Regeneration through Collagen Tubes up to Level of Autograft," 154(2) Experimental Neurology 315-329 (Dec. 1998).
Chamberlain, "Long term functional and morphological evaluation of peripheral nerves regenerated through degradable collagen implants," (M.S. Thesis, Massachusetts Institute of Technology, 1998) Abstract.
Deie et al., "High intrinsic healing potential of human anterior cruciate ligament," 66(1) Acta. Orthop. Scand. 28-32 (1995).
Desrosiers et al., "Proliferative and matrix synthesis response of canine anterior cruciate ligament fibroblasts submitted to combined growth factors," 14(2) J. Orthop. Res. 200-208 (1996).
Dye, "The Future of Anterior Cruciate Ligament Restoration," 325 CLIN. Orthop. 130-139 (1996).
Faryniarz, et al., "Myofibroblasts in the healing lapine medial collateral ligament: possible mechanisms of contraction," 14(2) J. Orthop. Res. 228-237 (1996).
Ferber, "Lab Grown Organs Take Shape," 284(5413) Science 422-425 (Apr. 16, 1999).
Ferber, "Tissue Engineering: From the Lab to the Clinic," 284(5413) Science 422-425 (Apr. 16, 1999).
Ford et al., "Autologous Collagen Vocal Fold Injection: A Preliminary Clinical Study," 105 Laryngoscope 944-948 (Sep. 1995).
Frank et al., "Natural History of Healing in the Repaired Medical Collateral Ligament," 1(2) J. Orthop. Res. 179-188 (1983).
Geiger et al., "An in vitro assay of anterior cruciate ligament (ACL) and medial collateral ligament (MCL) cell migration," 30(3) Connect Tissue Res. 215-224 (1994).
Gerich et al., "Gene transfer to the patellar tendon," Knee Surg, Sports Traumatol, Arthroscopy (1997) 5:118-123.
Gwinn et al., "Relative general incidence of anterior cruciate ligament injury at a military service academy," 66th Annual Meeting of Amer. Acad. of Orthop. Surg., Anaheim, California (1999).
Hefti et al., "Healing of the Transected Anterior Cruciate Ligament in the Rabbit," 73A (3) J. Bone Joint Surg. 373-383 (Mar. 1991).
Jackson et al., "Biologic remodeling after anterior cruciate ligament reconstruction using a collagen matrix derived from demineralized bone: an experimental study in the goat model," 24(4) Am. J. Sports Med. 405-414 (Jul.-Aug. 1996).
Juncosa-Melvin et al., The effect of autologous mesenchymal stem cells on the biomechanics and histology of gel-collagen sponge constructs used for rabbit patellar tendon repair. Tissue Eng. Feb. 2006;12(2):369-79.
Kanungo et al., Density-property relationships in mineralized collagen-glycosaminoglycan scaffolds. Acta Biomater. May 2009;5(4):1006-18. doi: 10.1016/j.actbio.2008.11.029. Epub Dec. 11, 2008.
Kato et al., "Formation of continuous collagen fibres: evaluation of biocompatibility and mechanical properties," 11 Biomaterials 169-175 (Apr. 1990).
Kawamoto et al., "Selective migration of alpha-smooth muscle actin-positive myofibroblasts toward fibronectin in the Boyden's blindwell chamber," 93(4) Clin. Sci. 355-362 (1997).
Louie, "Effect of a porous collagen-glycosaminoglycan copolymer on early tendon healing in a novel animal model," (Ph.D. Thesis, Massachusetts Institute of Technology, 1997) Abstract.

Louie, L. K. et al., "Healing of tendon defects implanted with a porous collagen-GAG matrix: histological evaluation," 3(2) Tissue Eng'g 187-195 (1997).
Louie, L. K., et al., "Development of a collagen-GAG copolymer implant for the study of tendon regeneration," M331 Mat. Res. Soc. Symp. Proc. 19-24 (1994).
Marshall et al., "The Anterior Cruciate Ligament: A Technique of Repair and Reconstruction," 143 Clin. Orthop. 97-106 (Sep. 1979).
Masur et al., "Myofibroblasts differentiate from fibroblasts when plated at low density," 93(9) Proc. Nat'l Acad. Sci. USA 4219-4223 (Apr. 1996).
Murray et al., "Differences in the outgrowth of cells from explants from the proximal and distal human ACL and response to TGF-B1," Transactions of the 47th Annual Meeting of the Orthopaedic Research Society, Feb. 25-28, 2001; San Francisco, CA.
Murray et al., "Fibroblast distribution in the anteriomedial bundle of the human anterior cruciate ligament: The presence of alpha smooth muscle actin-positive cells," 17(1) J. Orthop. Res. 18-27 (1999).
Murray et al., "Histological changes in the human anterior cruciate ligament after rupture," 82A(10) J. Bone Joint Surg. 1387-1397 (2000).
Murray et al., "Migration of cells from human anterior cruciate ligament explants into collagen-glycosaminoglycan scaffolds," 18(4) J. Orthop. Res. 557-564 (2000).
Murray et al., "Migration of cells from ruptured human anterior cruciate ligament explants into collagen-GAG matrices," Proceedings of the Sixth World Biomaterials Congress, 2000; Kamuela, Hawaii.
Murray et al., "Migration of human anterior cruciate ligament fibroblasts into porous collagen-GAG matrices in vitro," 24th Annual Meeting of the Society for Biomaterials, Apr. 22-26, 1996, San Diego, CA p. 463.
Murray et al., "The effect of ruptured human anterior cruciate ligament histology on cell interactions with a CG scaffold," Davos Tissue Engineering Workshop, 2000; Davos, Switzerland.
Murray et al., "The effects of selected growth factors on human ACL cell interactions with 3-D collagen-GAG scaffolds," Transactions of the 47th Annual Meeting of the Orthopaedic Research Society, Feb. 25-28, 2001; San Francisco, CA.
Murray et al., "The migration of cells from the ruptured human anterior cruciate ligament into collagen-glycosaminoglycan regeneration templates in vitro," 22 Biomat. 2393-2402 (2001).
Murray et al., "The migration of human anterior cruciate ligament fibroblasts into porous collagen-GAG matrices in vitro," 45th Annual Meeting, Orthopedic Research Society, Anaheim, California (Feb. 1-4, 1999).
Murray, M.M., et al., Use of a collagen-platelet rich plasma scaffold to stimulate healing of a central defect in the canine ACL, J Orthop Res. Apr. 24, 2006 (4):820-30. Abstract.
Nakamura et al., "A comparison of in vivo gene delivery methods for antisense therapy in ligament healing," Gene Therapy (1998) 5: 1455-1461.
Nakamura et al., "Early biological effect of in vivo gene transfer of platelet-derived growth factor (PDGF)-S into healing patellar ligament," Gene Therapy (1998) 5: 1165- 1170.
Niklason et al., "Functional arteries grown in vitro," 284(5413) Science 489-493 (Apr. 16, 1999).
Noyes et al., 72A(8) J. Bone Joint Surg. 1125-1136 (Sep. 1990).
Parkhurst et al., Quantification of human neutrophil motility in three-dimensional collagen gels. Effect of collagen concentration. Biophys J. Feb. 1992;61(2):306-15.
Peter et al., "Synthesis of poly(propylene fumarate) by acylation of propylene glycol in the presence of a proton scavenger," 10(3) J. Biomater. Sci. Polym. Ed. 363-373 (1999).
Qiu et al., "Outgrowth of chondrocytes from human articular cartilage explants, and expression of alpha-smooth muscle actin," 18 Wound Repair and Regeneration 383-391 (Sep.-Oct. 2000).
Schmidt et al., "Effect of growth factors on the proliferation of fibroblasts from the medial collateral and anterior cruciate ligaments," 13(2) J. Orthop. Res. 184-190 (1995).
Spindler et al., "Comparison of collagen synthesis in the peripheral and central region of the canine meniscus," 303 Clinical Orthopaedics 256-263 (Jun. 1994).

(56) References Cited

OTHER PUBLICATIONS

Spindler et al., "Patellar tendon and anterior cruciate ligament have different mitogenic responses to platelet-derived growth factor and transforming growth factor Beta," 14(4) J. Orthop. Res. 542-546 (1996).

Spindler et al., "Regional mitogenic response of the meniscus to platelet-derived growth factor (PDGF-AB)," 13(2) J. Orthop. Res. 201-207 (1995).

Stevenson, "Gender differences in knee injury epidemiology among competitive alpine ski racers," 18 Iowa Orthop. J. 64-66 (1998).

Stone et al., "Future Directions: Collagen-Based Prostheses for Meniscal Regeneration," 252 Clinical Orthopaedics and Related Research 129-135 (Mar. 1990).

Stone et al., "Regeneration of Meniscal Cartilage with Use of a Collagen Scaffold," 79A(12) J. Bone and Joint Surg. 1770-1777 (Dec. 1997).

Suggs et al., "Platelet adhesion on a bioresorgable poly(propylene fumarate-co-ethylene glycol) copolymer," 20(7) Biomaterials 683-690 (1999).

Torres, "Effects of modulus of elasticity of collagen sponges on their cell-mediated contraction in vitro," M. S. Thesis, Massachusetts Institute of Technology (1998).

Troxel, "Delay of skin wound contraction by porous collagen-GAG matrices," (Ph. D. Thesis, Massachusetts Institute of Technology, 1994).

Weadock et al., "Physical crosslinking of collagen fibers: comparison of ultraviolet irradiation and dehydrothermal treatment," 29 J. Biomed. Mater. Res. 1373-1379 (1995).

Witkowski et al., " Migration and Healing of Ligament Cells under Inflammatory Conditions," 15(2) J. Orthop. Res. 269-277 (1997).

Yannas et al., "Synthesis and characterization of a model extracellular matrix that induces partial regeneration of adult mammalian skin," 86 Proc. Natl. Acad. Sci USA 933-937 (Feb. 1989).

Yannas, "Models of Organ Regeneration Processes Induces by Templates," Bioartificial Organs: Science, Medicine, and Technology, Prokop et al. Ed., pp. 280-293 (The New York Academy of Sciences, New York, NY 1997).

Yannas, Collagen vol. 3, Biotechnology, Nimni Ed., p. 87-115 (CRC Press, Boca Raton, Florida, 1989).

Yannas, et al., "Polymeric template facilitates regeneration of sciatic nerve across 15-millimeter gap," 8 Trans. Soc. Biomater. 146 (1985).

Crapo et al., An overview of tissue and whole organ decellularization processes. Biomaterials. Apr. 2011;32(12):3233-43. doi: 10.1016/j.biomaterials.2011.01.057 Epub Feb. 5, 2011.

* cited by examiner

METHODS AND PRODUCTS FOR TISSUE REPAIR

CROSS REFERENCE TO RELATED APPLICATIONS

This Application is a continuation application which claims the benefit under 35 U.S.C. §120 of U.S. application Ser. No. 13/862,554, entitled "METHODS AND PRODUCTS FOR TISSUE REPAIR" filed on Apr. 15, 2013, which is a continuation of U.S. application Ser. No. 12/412,692, entitled "METHODS AND COLLAGEN PRODUCTS FOR TISSUE REPAIR" filed on Mar. 27, 2009, now abandoned, which are herein incorporated by reference in their entirety. Application Ser. No. 12/412,692 is a continuation of International Patent Application Serial No. PCT/US2007/021009, entitled "METHODS AND COLLAGEN PRODUCTS FOR TISSUE REPAIR" filed Sep. 28, 2007, which is herein incorporated by reference in its entirety. Application PCT/US2007/021009 claims priority under 35 U.S.C. §119 (e) to U.S. Provisional Application Ser. No. 60/847,743, entitled "METHODS AND PRODUCTS FOR TISSUE REPAIR" filed on Sep. 28, 2006, which is herein incorporated by reference in its entirety.

FEDERALLY SPONSORED RESEARCH

This invention was made with Government support under NIH K02 AR049346. Accordingly, the Government may have certain rights in this invention.

FIELD OF THE INVENTION

The invention relates generally to methods and devices for the repair of articular tissue using collagen materials.

BACKGROUND OF THE INVENTION

Intra-articular tissues, such as the anterior cruciate ligament (ACL), do not heal after rupture. In addition, the meniscus and the articular cartilage in human joints also often fail to heal after an injury. Tissues found outside of joints heal by forming a fibrin clot, which connects the ruptured tissue ends and is subsequently remodeled to form scar, which heals the tissue. Inside a synovial joint, a fibrin clot either fails to form or is quickly lysed after injury to the knee, thus preventing joint arthrosis and stiffness after minor injury. Joints contain synovial fluid which, as part of normal joint activity, naturally prevent clot formation in joints. This fibrinolytic process results in premature loss of the fibrin clot scaffold and disruption of the healing process for tissues within the joint or within intra-articular tissues.

Enhancing healing of ligaments using growth factors has been an area of great interest and research. While the majority of studies have focused on the use of a single growth factor to stimulate healing, the natural wound healing process is an orchestration of multiple growth factors released by platelets and other cells over time. To try to reproduce this in the in vitro and in vivo environment, prior investigators have looked at sustained release carriers and viral vectors for release of these cytokines over days or weeks, as well as examining applications of multiple growth factors. These studies have shown some additive effects of applied combinations of growth factors on the wound healing of ligaments; however, even with advanced application techniques, the combinations of growth factors, timing of release and concentration of release make optimization of these systems difficult.

An alternative method recently used to stimulate healing of the anterior cruciate ligament is the application of activated platelet-rich plasma (PRP). PRP is a combination of the extracellular matrix proteins normally found in plasma (including fibrinogen and fibronectin) and platelets. When platelets are activated by the exposed collagen of a ligament injury, they begin to aggregate and release multiple growth factors including platelet-derived growth factor (PDGFαα, PDGF αβ, PDGF ββ), transforming growth factors-β (TGFβ1, TGFβ2), vascular endothelial growth factor, basic fibroblast growth factor (FGF2), IGF-1 and epithelial growth factor. Growth factor release typically occurs immediately upon platelet activation and is sustained at much lower levels for the life-span of the platelet—up to 5-7 days.

PRP can be used to increase local concentrations of active PDGF-αβ and TGF-β1 by over 300% when platelets are concentrated in the plasma to a similar degree. This degree of platelet concentration can be accomplished by several available systems. As seen in vivo, these levels of cytokines released locally by these platelet concentrates can result in increased fibroblast DNA synthesis and up-regulation of type I collagen production and changes in collagen organization, and indeed the use of far lower concentrations (10 ng/ml TGF-β1 and 20 ng/ml PDGF-αβ can influence fibroblast proliferation, fibroblast chemotaxis, collagen production and collagen organization. The use of PRP over purified growth factor concentrates provides the added benefit of additional ECM proteins which also stimulate cellular adhesion and collagen synthesis, particularly in the presence of collagen fibrils.

SUMMARY OF THE INVENTION

The invention relates in some aspects to methods and products that facilitate anterior cruciate ligament regeneration or healing.

In some aspects the invention is a composition of a sterile solution of solubilized collagen in a concentration of greater than 5 and less than or equal to 50 mg/ml and having a viscosity of 1,000-200,000 centipoise, hydroxyproline in a concentration of 0.1-5.0 µg/ml, a neutralizing agent wherein the solution has an osmolarity of 280-350 mOs/kg, wherein the composition is free of thrombin.

In other aspects the invention is a composition of a sterile solution of solubilized collagen in a concentration of greater than 1 and less than 5 mg/ml and having a viscosity of 1,000-200,000 centipoise, hydroxyproline in a concentration of 0.1-5.0 µg/ml, wherein the solution has an osmolarity of 280-350 mOs/kg, wherein the composition is free of thrombin.

A dried powder composition of sterile solubilized collagen, at least one of decorin and biglycan, and buffer salts, wherein the composition is free of thrombin may be provided according to other aspects of the invention.

In other aspects the invention is a quick set composition of a sterile solution of solubilized collagen in a concentration of greater than 5 and less than or equal to 50 mg/ml and having a viscosity of 1,000-200,000 centipoises and a pH of 6.8-8.0, wherein the solution has an osmolarity of 280-350 mOs/kg, wherein the solution sets into a scaffold within 10 minutes of exposure to temperatures of greater than 30° C. The solution in some embodiments may be a liquid or a gel.

In some embodiments the composition further comprises a buffer. The composition may have a pH of 6.8-8.0. In some embodiments the composition has a pH of 7.4. In some embodiments the solution is maintained at a temperature of 4° C.

In some embodiments the solubilized collagen is present in a concentration of greater than 15 mg/ml. The collagen may be Type I, II or III collagen in some embodiments. The collagen may be pepsin solubilized collagen, enzyme solubilized collagen or it may be atelocollagen in certain embodiments.

In some embodiments each of the compositions includes at least one of decorin and biglycan. In other embodiments each of the composition includes both decorin and biglycan.

The composition may include other components, such as, an antibiotic, an anti-plasmin agent, a plasminogen activator inhibitor, fibrinogen, a glycosaminoglycan, insoluble collagen, a non-toxic cross-linking agent, or an accelerator. The composition may also include platelets or white blood cells. In other embodiments, the composition may include a neutralizing agent.

In other aspects, the invention is a method for preparing a collagen scaffold, by preparing a sterile solution of solubilized collagen in a concentration of greater than 5 and less than or equal to 50 mg/ml and having a viscosity of 1,000-200,000 centipoises, and subjecting the sterile solution of solubilized collagen to a temperature of at least 30° C. wherein the sterile solution of solubilized collagen forms a collagen scaffold.

In some embodiments, the collagen scaffold includes any of the optional components or has any of the properties described above.

A method for preparing a collagen scaffold by preparing a sterile solution of solubilized collagen in a concentration of greater than 1 and less than 5 mg/ml and having a viscosity of 1,000-200,000 centipoises, and subjecting the sterile solution of solubilized collagen to a temperature of at least 30° C. wherein the sterile solution of solubilized collagen forms a collagen scaffold is provided according to other aspects of the invention.

In some embodiments, the collagen scaffold includes any of the optional components or has any of the properties described above. In other embodiments the collagen scaffold includes an accelerator.

In other aspects a kit, including a first container housing a solubilized collagen solution in a concentration of greater than 5 and less than or equal to 50 mg/ml and having a viscosity of 1,000-200,000 centipoise, buffer salts housed in the first container or in a second container, and instructions for preparing a solution from the solubilized collagen solution and the buffer salts is provided.

A kit, including a container housing a solubilized collagen solution in a concentration of greater than 5 and less than or equal to 50 mg/ml and having a viscosity of 1,000-200,000 centipoise, a device for housing blood, and instructions for preparing a gel from the solubilized collagen solution and blood components isolated from the blood housed in the device is provided according to other aspects of the invention.

In another aspect, the invention is a kit, including a container housing a powder comprising collagen, a device for housing blood, and instructions for preparing a gel from the solubilized collagen solution and blood components isolated from the blood housed in the device. In one embodiment the powder includes a neutralization agent.

In some embodiments, the collagen scaffold includes any of the optional components or has any of the properties described above. For instance, in some embodiments the solution is a liquid or a gel.

In certain embodiments the buffer salts are housed in the first container and are part of the solubilized collagen solution. In other embodiments the buffer salts are housed in the second container.

The kit may also include a container housing a neutralization solution.

The kit may also include a device for housing blood. In some embodiments the device for housing the blood is a syringe that is capable of being used for collecting blood. In other embodiments the device for housing the blood is a centrifuge tube. An anticoagulant may optionally be included in the device for housing the blood or in a separate container. In yet other embodiments the kit includes a vortex tube.

The invention according to other aspects is a method comprising contacting the ends of a ruptured articular tissue in a subject with a sterile solution of solubilized collagen in a concentration of greater than 5 and less than or equal to 50 mg/ml and having a viscosity of 1,000-200,000 centipoises and a pH of 6.8-8.0, and hydroxyproline in a concentration of 0.1-5.0 μg/ml, wherein the solution has an osmolarity of 280-350 mOs/kg, wherein the composition does not include thrombin, and allowing the solution to set to treat the ruptured articular tissue.

In some embodiments the articular tissue is intra-articular tissue. An intra-articular injury may be, for instance, a meniscal tear, ligament tear or a cartilage lesion.

In other embodiments the articular tissue is extra-articular tissue. An extra-articular injury may be, for instance, ligament, tendon or muscle injury.

The method may involve mechanically joining the ends of the ruptured tissue.

A method for replacing a ruptured articular tissue, by mechanically securing a prosthetic device to tissue proximal to a site of ruptured articular tissue, wherein the prosthetic device has an inductive core and an adhesive zone disposed on at least a portion of the inductive core and which is adapted to provide a microenvironment between the tissue proximal to a site of ruptured articular tissue and the inductive core to promote cell migration from the tissue proximal to a site of ruptured articular tissue into the inductive core; and allowing bonds to form between the tissue proximal to a site of ruptured articular tissue and the adhesive zone of the prosthetic device is provided according to other aspects of the invention. in one embodiment the tissue proximal to a site of ruptured articular tissue is bone. In another embodiment the inductive core is a collagen sponge.

In another aspect, the invention is a method comprising contacting the ends of a ruptured articular tissue in a subject with a sterile solution of solubilized collagen and white blood cells in a concentration of at least $4 \times 10^3$ wbc/ml, and allowing the solution to set to treat the ruptured articular tissue.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including", "comprising", or "having", "containing", "involving", and variations thereof herein, is meant to encompass the items listed thereafter and equivalents thereof as well as additional items.

BRIEF DESCRIPTION OF THE DRAWINGS

The figures are illustrative only and are not required for enablement of the invention disclosed herein.

FIG. 23A depicts fail load as a function of platelet count. FIG. 23B depicts stiffness as a function of platelet count.

DETAILED DESCRIPTION OF THE INVENTION

Figure 1:
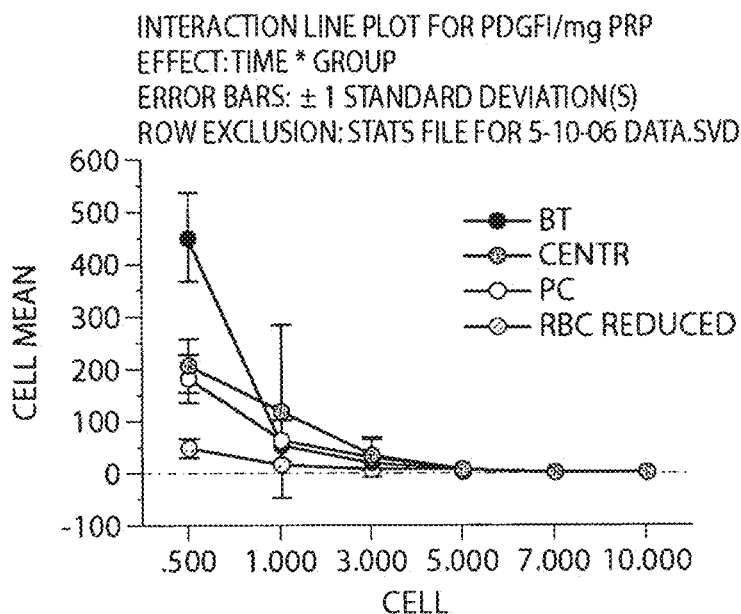
FIG. 1 is a graph depicting release of PDGF-αβ over time from bovine thrombin-activated (BT) and collagen-activated (CENTR (centrifuged PRP), PC (platelet concentrate) and RBC Reduced platelet concentrate) PRP hydrogels.

Aspects of the invention relate to compositions and methods for repairing damaged articular tissue. The invention involves novel collagen based compositions and formulations for repairing articular tissue, such as a ruptured or torn ligament for instance. The compositions may be used alone or in combination with three-dimensional (3-D) scaffolds or other traditional repair devices. The material provides a connection between the ruptured ends of the ligament and fibers, or provides a replacement, alone or in combination with other devices, for a torn ligament, after injury, and encourages the migration of appropriate healing cells to form scar and new tissue, thus facilitating healing and regeneration.

It is intended that the use of the compositions and methods of the present invention involve the repair, replacement, reconstruction or augmentation of specific tissue types. Articular injuries include both intra-articular and extra-articular injuries. Intra-articular injuries involve, for instance, injuries to meniscus, ligament and cartilage. Extra-articular injuries include, but are not limited to injuries to the ligament, tendon or muscle. Thus, the methods of the invention may be used to treat injuries to the Anterior cruciate ligament (ACL), Lateral collateral ligament (LCL), Posterior cruciate ligament (PCL), Medial collateral ligament (MCL), Volar radiocarpal ligament, Dorsal radiocarpal ligament, Ulnar collateral ligament, Radial collateral ligament, meniscus, labrum, for example glenoid labrum and acetabular labrum, cartilage, for example, and other tissues exposed to synovial fluid after injury.

The injury being treated may be, for instance, a torn or ruptured ligament. A ligament is a short band of tough fibrous connective tissue composed of collagen fibers. Ligaments connect bones to other bones to form a joint. A torn ligament is one where the ligament remains connected but has been damaged causing a tear in the ligament. The tear may be of any length or shape. A ruptured ligament is one where the ligament has been completely severed providing two separate ends of the ligament. A ruptured ligament may provide two ligament ends of similar or different lengths. The rupture may be such that a ligament stump is formed at one end.

An example of a ruptured anterior cruciate ligament is described for exemplary purposes only. The anterior cruciate ligament (ACL) is one of four strong ligaments that connects the bones of the knee joint. The function of the ACL is to provide stability to the knee and minimize stress across the knee joint. It restrains excessive forward movement of the lower leg bone, the tibia, in relation to the thigh bone, the femur, and limits the rotational movements of the knee. An anterior cruciate ligament is ruptured such that it no longer forms a connection between the femur bone and the tibia bone. The resulting ends of the ruptured ACL may be of any length. The ends may be of a similar length, or one end may be longer in length than the other.

The repair of the damaged tissue is achieved using collagen based repair material alone or in combination with a tissue healing device. A tissue healing device is a device other than the repair material that aids in the repair of the damaged tissue and includes, for instance, scaffolds, such as sponges and grafts and mechanical devices, such as sutures and anchors.

The damaged or injured tissue is treated with a novel composition which is a sterile solution of solubilized collagen. Solubilized collagen, as used herein, is enzyme solubilized collagen including one or more of Type I, II, III, IV, V, X collagen. Preferably the enzyme solubilized collagen is tropocollagen or Atelocollagen rather than fibrillar collagen in order to reduce the antigenicity of the material. The collagen is isolated from a source and mechanically minced and broken up in an enzyme based acid media rather than aqueous or salt solution. For instance, the collagen may be solubilized in pepsin. The step of mechanically mincing the collagen is important for homogenization to produce a material of uniform consistency that is free of aggregates and lumps.

The pH of the solution during the solubilization is very acidic, for instance, a pH=2.0 is normally obtained during solubilization with pepsin. A preferred pH for storage of the material is 2.0 to 6.5. Preferably the collagen is kept cold (4° C. or on ice) during storage and throughout the preparation.

In one embodiment the solubilized collagen is Type I collagen. As used herein the term, "Type I collagen" is characterized by two $\alpha 1(I)$ chains, and one $\alpha 2(I)$ chains (heterotrimeric collagen). The $\alpha 1$ (I) chains are approximately 300 nm long. Type I collagen is predominantly found in bone, skin (in sheet-like structures), and tendon (in rope-like structures). Type I collagen is further typified by its reaction with the protein core of another connective tissue component known as a proteoglycan. Type I collagen contains signaling regions that facilitate cell migration.

The collagen is synthetic or naturally derived. Natural sources of collagen may be obtained from animal or human sources. For instance, it may be derived from rat, pig, cow, or human tissue or tissue from any other species. Tendons, ligaments, muscle, fascia, skin, cartilage, tail, or any source of collagenous tissue are useful. The material is then implanted into a subject of the same or different species. The terms "xenogeneic" and "xenograft" refer to cells or tissue which originates with or is derived from a species other than that of the recipient. Alternatively the collagen may be obtained from autologous cells. For instance, the collagen may be derived from a patient's fibroblasts which have been cultured. The collagen may then be used in that patient or other patients. The terms "autologous" and "autograft" refer to tissue or cells which originate with or are derived from the recipient, whereas the terms "allogeneic" and "allograft" refer to cells and tissue which originate with or are derived from a donor of the same species as the recipient. The collagen may be isolated anytime before surgery.

The solubilized collagen may be in a concentration of 1-50 mg/ml in the solution. In some embodiments that concentration of solubilized collagen is greater than 5 mg/ml and less than or equal to 50 mg/ml. The concentration of collagen may be, for instance, 10, 15, 20, 25, 30, 35, or 40 mg/ml. Such high concentrations of collagen are useful for producing viscosity levels that are desirable for the methods of the invention. Most commercially available collagen solutions are of lower concentrations. Higher concentrations can be made, for instance, using the methods described herein. In other embodiments the solubilized collagen solution has a concentration of 1 mg/ml to less than 5 mg/ml. When such lower concentrations of collagen are used, additional components or steps are taken to increase the viscosity of the material in order to be useful according to the methods of the invention. Examples of viscosity inducing methods or components are described herein.

The solution should be prepared, by varying the collagen content and other components, to provide the desired flow properties of the finished composition. In some embodiments the solution has a collagen viscosity of 1,000 to 200,000 centipoise.

The collagen solution is sterile for in vivo use. The solution may be sterilized and/or components of the solution may be isolated under sterile conditions using sterile techniques to produce a sterile composition. The final desired properties of the composition may be determinative of how the solution is sterilized because some sterilization techniques may affect properties such as viscosity. If certain components of the solution are not to be sterilized, i.e., the collagen isolated from natural sources, the remaining components can be combined and sterilized before addition of the collagen, or each component can be sterilized separately. The solution can then be made by mixing each of the sterilized components with the collagen that has been isolated using sterile techniques under sterile conditions. Sterilization may be accomplished, for instance, by autoclaving at temperatures on the order of about 115° C. to 130° C., preferably about 120° C. to 125° C. for about 30 minutes to 1 hour. Gamma radiation is another method for sterilizing components. Filtration is also possible, as is sterilization with ethylene oxide.

The solubilized collagen solution may contain additional components, such as insoluble collagen, other extracellular matrix proteins (ECM), such as proteoglycans and glycosaminoglycans, fibronectin, laminin, entectin, decorin, lysyl oxidase, crosslinking precursors (reducible and non-reducible), elastin, elastin crosslink precursors, cell components such as, cell membrane proteins, mitochondrial proteins, nuclear proteins, cytosomal proteins, and cell surface receptors, growth Factors, such as, PDGF, TGF, EGF, and VEGF, and hydroxyproline. In some embodiments hydroxyproline may be present in the solution in a concentration of 1 to 3.0 m/ml, which may be 8 to 9% of the total protein in the collagen solution. In some embodiments, the hydroxyproline is present in a concentration of 0.5 to 4.0 µg/ml in the collagen solution prior to the addition of any buffer. In some embodiments the collagen solution is free of thrombin. "Free of thrombin" as used herein refers to a composition which has less than 1% thrombin. In some embodiments, free of thrombin refers to undetectable levels. In other embodiments it refers to 0% thrombin.

The collagen is mixed with one or more buffers to produce a solution having a desirable pH range for subsequent mixing with cells and application to the body. Ideally the buffer solution(s) has no toxic components or residue, confers physiologic osmolarity and has the capacity to keep the solution at physiologic pH. A preferred buffer used in accordance with the invention is a HEPES buffer. However, any buffer that is non-toxic and is capable of regulating the pH and/or osmolarity to the levels described herein is useful according to the invention. HEPES is N-2-Hydroxyethyl-piperazine-N'-2-ethanesulfonic acid, (molecular weight and structure=238.31, $C_8H_{18}N_2O_4S$). For instance, the inventors have found the following buffer solution achieves the appropriate pH and osmolartiy values:

0.1M HEPES
10× Ham's F-10 medium
100× antibiotic/antimycotic solution (10,000 I.U. Penicillin, 10,000 µg/mL Streptomycin, 25 µg/mL Amphotericin B from CellGro by Mediatech)
Ultra pure sterile water
7.5% sodium bicarbonate
$NaHCO_3$ The components of 10× Ham's F-10 include the following:
Formulation (as 10×):

| Component | mg/lt | Mol. Wt. | Mol. (mM) |
|---|---|---|---|
| Amino Acids | | | |
| L-Alanine | 89.10000 | 89.1 | 1.00 |
| L-Arginine HCl | 2107.00000 | 174.2 | 12.10 |
| L-Asparagine H₂O | 150.10000 | 150.1 | 1.00 |
| L-Aspartic Acid | 133.10000 | 133.1 | 1.00 |
| L-Cysteine HCl H₂O | 351.30000 | 175.6 | 2.00 |
| L-Glutamic Acid | 147.10000 | 147.1 | 1.00 |
| Glycine | 75.10000 | 75.07 | 1.00 |
| L-Histidine HCl H₂O | 209.60000 | 209.6 | 1.00 |
| L-Isoleucine | 26.20000 | 131.2 | 0.20 |
| L-Leucine | 131.20000 | 131.2 | 1.00 |
| L-Lysine HCl | 293.00000 | 182.6 | 1.60 |
| L-Methionine | 44.80000 | 149.2 | 0.30 |
| L-Phenylalanine | 49.60000 | 165.2 | 0.30 |
| L-Proline | 115.10000 | 115.1 | 1.00 |
| L-Serine | 105.10000 | 105.1 | 1.00 |
| L-Threonine | 35.70000 | 119.1 | 0.30 |
| L-Tryptophan | 6.10000 | 204.2 | 0.03 |
| L-Tyrosine | 18.10000 | 181.2 | 0.10 |
| L-Valine | 35.10000 | 117.1 | 0.30 |
| Vitamins | | | |
| Biotin | 0.24000 | 244.3 | 0.0010 |
| Choline Chloride | 6.98000 | 139.6 | 0.05 |
| D-Calcium Pantothenate | 7.15000 | 238.3 | 0.03 |
| Folic Acid | 13.20000 | 441.4 | 0.03 |
| myo-Inositol | 5.41000 | 180.2 | 0.03 |
| Nicotinamide | 6.11000 | 122.13 | 0.05 |
| Pyridoxine HCl | 2.06000 | 205.6 | 0.01 |
| Riboflavin | 3.76000 | 376.4 | 0.01 |
| Thiamine HCl | 10.12000 | 337.3 | 0.03 |
| Vitamin B12 | 13.60000 | 1355.4 | 0.01 |
| Inorganic Salts | | | |
| Calcium Chloride [CaCl₂ 2H₂O] Dihydrate | 441.00000 | 147 | 3.00 |
| Cupric Sulfate [CuSO₄] | 0.01600 | 159.68 | 0.0001 |
| Ferrous Sulfate [FeSO₄ 7H₂O] Heptahydrate | 8.34 | 278 | 0.03 |
| Magnesium Sulfate [MgSO₄] | 746.00000 | 120.4 | 6.20 |
| Potassium Chloride [KCl] | 2850.00000 | 74.55 | 38.23 |
| Potassium Phosphate Monobasic [KH₂PO₄] | 830.00000 | 136.09 | 6.10 |
| Sodium Chloride [NaCl] | 74000.00000 | 58.44 | 1266.26 |
| Sodium Phosphate Dibasic [Na₂HPO₄] | 1562.00000 | 141.96 | 11.00 |
| Zinc Sulfate [ZnSO₄ 7H₂O] Heptahydrate | 0.28800 | 287.5 | 0.0010 |
| Other | | | |
| Dextrose | 11000.00000 | 180.2 | 61.04 |
| Hypoxanthine | 40.80000 | 136.1 | 0.30 |
| Lipoic Acid | 2.06000 | 206.3 | 0.01 |
| Phenol Red Sodium Salt | 12.40000 | 376.4 | 0.03 |
| Sodium Pyruvate | 1100.00000 | 110 | 10.00 |
| Thymidine | 7.27000 | 242.2 | 0.03 |

The above-described buffer is exemplary. Many of the components are not essential For instance, it is not essential to use sterile water, as long as the appropriate osmolarity is maintained. The 10× F10 solution is also optional. The buffer may be prepared without 10× F10 or equivalent solution. Additionally glucose or other sugar may be used in place of the 10× F10.

The buffer may or may not include an antibiotic. For instance, the antibiotic may be penicillin/streptomycin as described above. Alternatively it may be a clinical antibiotic, which is used in human patients for the treatment or prevention of diseases, such as any of those described in Remington's Pharmaceutical Sciences (Mack Publishing Co., Easton Pa.), which is hereby incorporated by reference.

The buffer may be a single component or it may be multiple components added at the same time or different times. If the buffer is a single component it should have properties that enable it to produce a solution having a desirable pH range and osmolarity. In some instances it is desirable to have at least two buffer components, a collagen buffer solution and a neutralizing buffer. The collagen buffer solution may be used to prepare the collagen in a solution. In some instances the prepared collagen solution may be stored for extended periods of time.

A neutralizing buffer, also referred to as a neutralizing agent, may be added as a solution or in the form of dried salts to a collagen solution. Once the neutralizing buffer is added the solution should be kept cold. If the materials are being processed at room temperature for extended periods of time, it is preferred that the neutralizing buffer be added to the collagen solution after storage. Thus, a collagen solution without a neutralization agent may be prepared ahead of time and stored or it may be prepared during surgery and used immediately. The neutralization agent may be added at surgery or ahead of time, but a neutralized collagen solution preferably should be kept cold (4° C. or on ice).

After the neutralizing agent is added to the collagen solution an osmolarity of 250 to 350 mOsm/kg is preferably achieved. Osmolarity is a count of the total number of osmotically active particles in a solution and is equal to the sum of the molarities of all the solutes present in that solution. It is defined as a measure of the osmoles of solute per liter of solution. Osmolarity is a measure of the osmoles of solute per kilogram of solvent. One of skill in the art can determine the osmolarity of a solution by obtaining measurements using an osmometer. An equation used to determine the osmolarity of a solution is:

$$Osm = \varphi nC$$

wherein $\varphi$ is the osmotic coefficient and accounts for the degree of dissociation of the solute. $\varphi$ is between 0 and 1 where 1 indicates 100% dissociation.

n is the number of particles into which a molecule dissociates.

C is the molal concentration of the solution

Additionally, after the neutralizing agent is added, preferably a pH between 6.8 and 9.0 is achieved. In some embodiments a pH of 6.8-8.0 is preferred. In other embodiments a pH of 7.2-7.6 or even 7.4 is preferred.

Preferably the buffer is sterile prior to addition to the collagen solution. If it is unsterile then it should be sterilized prior to addition to the collagen solution or the whole collagen/buffer solution should be sterilized as described herein. The components of the buffer may be unsterile and then filtered at a point before it is mixed with the collagen.

In certain embodiments, the collagen solution is mixed with cells such as platelets or white blood cells. In some embodiments, the cells are derived from the subject to be treated. In other embodiments, the cells are derived from a donor that is allogeneic to the subject.

In certain embodiments, platelets may be obtained as platelet rich plasma (PRP). This component contains fibrin and platelets as well as other plasma proteins found in the blood. There may also be some white blood cells (WBC) and red blood cells (RBC) found in this preparation. Preferably the platelet concentration of PRP is at least 100K/ml, and preferably over 300K/ml. For instance, the platelet concentration may be at least 1× what it is in the blood of the patient, and preferably 1.5× or greater In order to maintain the stability of the cells a physiologic pH (i.e., 6.2 to 7.6) and a physiologic plasma osmolarity (i.e., 280-360 osms/kg) is used. In order to enhance the function of the PRP, preferably the PRP is used within 7 days of being drawn from the patient or donor. Often the PRP is isolated from the patient at time of surgery. Preferably it is stored at 20 to 24° C. (room temp). However, isolation and storage of the cells may be achieved by any methods and for any length of time known in the art for maintaining the activity of the active components.

In a non-limiting example, platelets may be isolated from a subject's blood using techniques known to those of ordinary skill in the art. As an example, a blood sample may be centrifuged at 700 rpm for 20 minutes and the platelet-rich plasma upper layer removed. Platelet density may be determined using a cell count as known to those of ordinary skill in the art. The platelet rich plasma may be mixed with collagen and applied to the patient.

In a non-limiting example, white blood cells may also be isolated from a subject's blood using techniques known to those of ordinary skill in the art. As an example, a blood sample may be centrifuged at 700 rpm for 20 minutes and the buffy coat containing white blood cells removed. WBC density may be determined using a cell count as known to those of ordinary skill in the art. The WBCs can be mixed with collagen and applied to the patient.

The collagen solution may also include any one or more of an anti-plasmin agent, an extracellular matrix (ECM) protein, other protein or enzyme inhibitors, antibodies to plasmin, antibodies to tissue plasminogen activator or urokinase plasminogen activator, non-toxic crosslinkers, calcium, dextrose or other sugars and cell nutrients in physiological concentrations. Anti-plasmin agents include but are not limited to antifibrinolytic enzymes such as plasminogen inactivator, plasminogen binding $\alpha_2$ antiplasmin, non-plasminogen binding $\alpha_2$ antiplasmin, $\alpha_2$ macroglobulin, $\alpha_2$ plasmin inhibitor, $\alpha_2$ antiplasmin, and thrombin activatable fibrinolysis inhibitor. Other protein or enzyme inhibitors include but are not limited to anti-enzymatic proteins including inhibitors of collagenase, trypsin, matrix metalloproteinases, elastase and hyaluronidase. The ECM is composed of fibrillar and non-fibrillar components. The major fibrillar proteins are collagen and elastin. The ECM includes for instance, diverse combinations of collagens, fibrinogen, proteoglycans, elastin, hyaluronic acid, and various glycoproteins including laminin, fibronectin, heparan sulfate proteoglycan, and entactin. Non-toxic crosslinkers include but are not limited to tissue transglutaminases, lysyl oxidase, fibrin, fibronectin, and reducible and non-reducible crosslink precursor molecules.

The collagen solution, with or without any of the above-described additional components, may be stored as a liquid or gel material or may be dried and stored as a powder. For instance, a collagen solution may be lyophilized to produce a powder. The powder may then be reconstituted in a buffer solution. Neutralizing agent may be present in the reconstitution buffer or may be added as a separate buffer or as salts.

The final collagen solution includes collagen, buffer and cells, such as PRP or WBCs. The components are mixed on a microscopic level, rather than layered. Preferably it has a pH of 7.4 and a minimum viscosity of approximately 1,000 centipoise. Preferably the viscosity is in the range of 1,000-200,000 centipoise.

While the degree of "solidness" may vary from application to application, generally speaking collagen solutions of the present invention will exhibit viscosities in the full range of from liquid to gel-like to solid-like. A collagen solution having optimal viscosity can be obtained directly from the source of collagen, depending on the concentration of the collagen. However, a collagen solution not having an optimal viscosity can be manipulated to create the correct viscosity. The viscosity of a collagen solution may be lowered by diluting the solution. The viscosity of a lower viscosity collagen solution may be increased to increase gelation. Gelation is the change in viscosity from a fluid-like composition to a solid or gel-like composition. Gelation or viscosity of a solution may be increased by adding one or more of the following: other ECM molecules, including but not limited to, insoluble collagen, fibrin, fibronectin, and cellulose; cell additions, including but not limited to, platelets and fibroblasts; non-toxic crosslinking agents, including but not limited to, tissue transglutaminases, lysyl oxidase, fibrin, and fibronectin; and other high viscosity materials with low osmolarity, including but not limited to, alginate and synthetic filler materials.

One example of a method for preparing and using the collagen solution of the invention is provided. The methods of the invention are not so limited and the description is provided for exemplary purposes only. Collagen is isolated from rat tails and processed 6 weeks to 6 months ahead of application time (surgery). A buffer solution is mixed ahead of time as well. The buffer is designed so collagen-buffer mixture will have pH of 7.4 and be iso-osmotic with plasma. The PRP is obtained from blood taken from the patient during anesthesia for surgery using a large bore needle and anticoagulant. The blood is centrifuged to get a PRP with platelet count of at least 1× normal. When the surgical site is ready, the collagen and buffer (containing neutralizing agent) are mixed first using vortex. The PRP is then added to the neutralized collagen-buffer mixture. The PRP and collagen are combined using a mixing process to produce a repair material. The resultant gel is injected arthroscopically into the joint wound site to promote the healing process.

The term "repair material" as used herein refers to the final formulation of collagen solution with cells to be delivered to the subject.

The collagen solution or repair material may include additional materials, such as growth factors, antibiotics, insoluble or soluble collagen, a cross-linking agent, thrombin, stem cells, a genetically altered fibroblast, platelets, water, plasma, extracellular proteins and a cell media supplement. Alternatively the collagen solution or repair material may exclude any of these components, and in particular thrombin. The additional materials may be added to affect cell proliferation, extracellular matrix production, consistency, inhibition of disease or infection, tonicity, cell nutrients until nutritional pathways are formed, and pH of the collagen solution or repair material. All or a portion of these additional materials may be mixed with the collagen solution or repair material before or during implantation, or alternatively, the additional materials may be implanted proximate to the defect area after the repair material is in place.

In general, the collagen solution is prepared in advance or at the time of surgery. At a temperature of preferably 4° C. to around room temperature PRP or WBCs are added. The PRP/WBC collagen mixture is kept on ice until use. Just prior to use the mixture may be warmed to a temperature of 24-30° C. (preferably 28° C.) and then immediately injected into the subject. In the subject the material is subjected to body temperatures in excess of 30 C to produce a gel.

The repair material of the invention, as discussed above, may be applied directly to the tissue alone or it may be used in combination with a tissue healing device such as a scaffold. Scaffolds may be synthetic or naturally occurring, such as in a graft. A device or scaffold may be any shape that is useful for implantation into a subject. The scaffold, for instance, can be tubular, semi-tubular, cylindrical, including either a solid cylinder or a cylinder having hollow cavities, a tube, a flat sheet rolled into a tube so as to define a hollow cavity, liquid, an amorphous shape which conforms to that of the repair space, a "Chinese finger trap" design, a trough shape, or square. Other shapes suitable for the scaffold of the device as known to those of ordinary skill in the art are also contemplated in the invention.

The scaffold may be pretreated with the repair material prior to implantation into a subject. For instance, the scaffold may be soaked in a repair material prior to or during implantation into a repair site. The repair material may be injected directly into the scaffold prior to or during implantation. The repair material may be injected within a scaffold at the time of repair.

A scaffold is capable of insertion into a repair site and either forming a connection between the ends of a ruptured tissue, or forming around a torn tissue such that, in either case, the integrity and structure of the tissue is maintained. A scaffold is preferably made of a compressible, resilient material which has some resistance to degradation by synovial fluid. Synovial fluid as part of normal joint activity, naturally prevents clot formation. This fibrinolytic process would result in the premature degradation of the scaffold and disrupt the healing process of the tissue. The material may be natural or synthetic and may be either permanent or biodegradable material, such as polymers and copolymers. The scaffold can be composed, for example, of collagen fibers, collagen gel, foamed rubber, natural material, synthetic materials such as rubber, silicone and plastic, ground and compacted material, perforated material, or a compressible solid material.

A scaffold that is capable of compression and expansion is particularly desirable. For example, a sponge scaffold may be compressed prior to or during implantation into a repair site. A compressed sponge scaffold allows for the sponge scaffold to expand within the repair site. Examples of scaffolds useful according to the invention are found in U.S. Pat. No. 6,964,685 and US Patent Application Nos. 2004/0059416 and 2005/0261736, the entire contents of each are herein incorporated by reference.

An important subset of natural matrices are those made predominantly from collagen, the main structural component in ligament. Collagen can be of the soluble or the insoluble type. Preferably, the collagen is soluble, e.g., acidic or basic. For example, the collagen can be type I, II, III, IV, V, IX or X. Preferably the collagen is type I. More preferably the collagen is soluble type I collagen. Type I collagen is the predominant component of the extracellular matrix for the human anterior cruciate ligament and provides an example of a choice for the basis of a bioengineered scaffold. Collagen occurs predominantly in a fibrous form, allowing design of materials with very different mechanical properties by altering the volume fraction, fiber orientation, and degree of cross-linking of the collagen. The biologic properties of cell infiltration rate and scaffold degradation may also be altered by varying the pore size, degree of cross-linking, and the use of additional proteins, such as glycosaminoglycans, growth factors, and cytokines. In addition, collagen-based biomaterials can be manufactured from a patient's own skin, thus minimizing the antigenicity of the implant (Ford et al., 105 Laryngoscope 944-948 (1995)).

Numerous matrices made of either natural or synthetic components have been investigated for use in tissue repair and reconstruction. Natural matrices are made from processed or reconstituted tissue components (such as collagens and GAGs). Because natural matrices mimic the structures ordinarily responsible for the reciprocal interaction between cells and their environment, they act as cell regulators with minimal modification, giving the cells the ability to remodel an implanted material, which is a prerequisite for regeneration.

Synthetic matrices are made predominantly of polymeric materials. Synthetic matrices offer the advantage of a range of carefully defined chemical compositions and structural arrangements. Some synthetic matrices are not degradable. While the non-degradable matrices may aid in repair, non-degradable matrices are not replaced by remodeling and therefore cannot be used to fully regenerate ligament. It is also undesirable to leave foreign materials permanently in a joint due to the problems associated with the generation of wear particles, thus degradable materials are preferred for work in regeneration. Degradable synthetic scaffolds can be engineered to control the rate of degradation.

A scaffold may be a solid material such that its shape is maintained, or a semi-solid material capable of altering its shape and or size. A scaffold may be made of expandable material allowing it to contract or expand as required. The material can be capable of absorbing plasma, blood, other body fluids, liquid, hydrogel, or other material the scaffold either comes into contact with or is added to the scaffold.

A scaffold material can be protein, lyophilized material, or any other suitable material. A protein can be synthetic, bioabsorbable or a naturally occurring protein. A protein includes, but is not limited to, fibrin, hyaluronic acid, or collagen. A scaffold material may incorporate therapeutic proteins including, but not limited to, hormones, cytokines, growth factors, clotting factors, anti-protease proteins (e.g., alpha1-antitrypsin), angiogenic proteins (e.g., vascular endothelial growth factor, fibroblast growth factors), anti-angiogenic proteins (e.g., endostatin, angiostatin), and other proteins that are present in the blood, bone morphogenic proteins (BMPs), osteoinductive factor (IFO), fibronectin (FN), endothelial cell growth factor (ECGF), cementum attachment extracts (CAE), ketanserin, human growth hormone (HGH), animal growth hormones, epidermal growth factor (EGF), interleukin-1 (IL-1), human alpha thrombin, transforming growth factor (TGF-beta), insulin-like growth factor (IGF-1), platelet derived growth factors (PDGF), fibroblast growth factors (FGF, bFGF, etc.), and periodontal ligament chemotactic factor (PDLGF), for therapeutic purposes. A lyophilized material is one that is capable of swelling when liquid, gel or other fluid is added or comes into contact with it.

The repair material may also be used in combination with a scaffold that is a graft, such as an ACL graft. Several types of ACL grafts are available for use by the surgeon in ACL reconstruction. The grafts may be autografts that are harvested from the patient, for example patellar bone-tendon-bone grafts, or hamstring grafts. Alternatively, the grafts can be xenografts, allografts, or synthetic polymer grafts. Allografts include ligamentous tissue harvested from cadavers and appropriately treated and disinfected, and preferably sterilized. Xenografts include harvested connective tissue from animal sources such as, for example, porcine tissue. Typically, the xenografts must be appropriately treated to eliminate or minimize an immune response. Synthetic grafts include grafts made from synthetic polymers such as polyurethane, polyethylene, polyester and other conventional biocompatible bioabsorbable or nonabsorbable polymers and composites, such as the scaffolds described herein.

Tissue healing devices also include mechanical devices such as sutures and anchors. An anchor is a device capable of insertion into a bone or tissue such that it forms a stable attachment to the bone or tissue. In some instances the anchor is capable of being removed from the bone if desired. An anchor may be conical shaped having a sharpened tip at one end and a body having a longitudinal axis. The body of an anchor may increase in diameter along its longitudinal axis. The body of an anchor may include grooves suitable for screwing the anchor into position. An anchor may include an eyelet at the base of the anchor body through which one or more sutures may be passed. The eyelet may be oval or round and may be of any size suitable to allow one or more sutures to pass through and be held within the eyelet.

An anchor may be attached to a bone or tissue by physical or mechanical methods as known to those of ordinary skill in the art. An anchor includes, but is not limited to, a screw, a barb, a helical anchor, a staple, a clip, a snap, a rivet, or a crimp-type anchor. The body of an anchor may be varied in length. Examples of anchors, include but are not limited to, IN-FAST™ Bone Screw System (Influence, Inc., San Francisco, Calif.), IN-TAC™ Bone Anchor System (Influence, Inc., San Francisco, Calif.), Model 3000 AXYALOOP™ Titanium Bone Anchor (Axya Medical Inc., Beverly, Mass.), OPUS MAGNUM® Anchor with Inserter (Opus Medical, Inc., San Juan Capistrano, Calif.), ANCHRON™, HEXALON™, TRINION™ (all available from Inion Inc., Oklahoma City, Okla.) and endobuttons and TwinFix AB absorbable suture anchor (Smith & Nephew, Inc., Andover, Mass.). Anchors are available commercially from manufacturers such as Influence, Inc., San Francisco, Calif., Axya Medical Inc., Beverly, Mass., Opus Medical, Inc., San Juan Capistrano, Calif., Inion Inc., Oklahoma City, Okla., and Smith & Nephew, Inc., Andover, Mass.

An anchor may be composed of a non-degradable material, such as metal, for example titanium 316 LVM stainless steel, CoCrMo alloy, or Nitinol alloy, or plastic. An anchor is preferably bioabsorbable such that the subject is capable of breaking down the anchor and absorbing it. Examples of bioabsorbable material include, but are not limited to, MONOCRYL (poliglecaprone 25), PDS II (polydioxanone), surgical gut suture (SGS), gut, coated VICRYL (polyglactin 910, polyglactin 910 braided), human autograft tendon material, collagen fiber, POLYSORB, poly-L-lactic acid (PLLA), polylactic acid (PLA), polysulfone, polylactides (Pla), racemic form of polylactide (D,L-Pla), poly(L-lactide-co-D,L-lactide), 70/30 poly(L-lactide-co-D,L-lactide), polyglycolides (PGa), polyglycolic acid (PGA), polycaprolactone (PCL), polydioxanone (PDS), polyhydroxyacids, and resorbable plate material (see e.g. Orthopedics, October 2002, Vol. 25, No. 10/Supp.). The anchor may be bioabsorbed over a period of time which includes, but is not limited to, days, weeks, months or years.

A suture is preferably bioabsorbable, such that the subject is capable of breaking down the suture and absorbing it, and synthetic such that the suture may not be from a natural source. Examples of sutures include, but are not limited to, VICRYL™ polyglactin 910, PANACRYL™ absorbable suture, ETHIBOND® EXCEL polyester suture, PDS® polydioxanone suture and PROLENE® polypropylene suture. Sutures are available commercially from manufacturers such as MITEK PRODUCTS division of ETHICON, INC. of Westwood, Mass.

A staple is a type of anchor having two arms that are capable of insertion into a bone or tissue. In some instances, the arms of the staple fold in on themselves when attached to a bone or in some instances when attached to other tissue. A staple may be composed of metal, for example titanium or stainless steel, plastic, or any biodegradable material. A staple includes but is not limited to linear staples, circular staples, curved staples or straight staples. Staples are available commercially from manufacturers such as Johnson & Johnson Health Care Systems, Inc. Piscataway, N.J., and Ethicon, Inc., Somerville, N.J. A staple may be attached using any staple device known to those of ordinary skill in the art, for example, a hammer and staple setter (staple holder).

The device may be inserted into a repair site of the ruptured or torn tissue. A repair site is the area around a ruptured or torn tissue into which the material of the invention may be inserted. A device may be placed into a repair site area during surgery using techniques known to those of ordinary skill in the art. If a scaffold is used in the methods, the scaffold can either fill the repair site or partially fill the repair site. A scaffold can partially fill the repair site when inserted and expand to fill the repair site in the presence of blood, plasma or other fluids either present within the repair site or added into the repair site, such as the repair material.

The scaffold may be positioned in combination with a surgical technique. For instance, a hole may be drilled into a bone at or near a repair site of a ruptured or torn tissue and the scaffold attached by a suture through the hole to the bone. A bone at or near a repair site is one that is within close proximity to the repair site and can be utilized using the methods and devices of the invention. For example, a bone at or near a repair site of a torn anterior cruciate ligament is a femur bone and/or a tibia bone. A hole can be drilled into a bone using a device such as a Kirschner wire (for example a small Kirschner wire) and drill, or microfracture pics or awls.

A hole may be drilled into a bone on the opposite side to the repair site. A suture may be passed through the hole in the bone and attached to the bone. A scaffold is attached to the suture to secure the scaffold between the bone and an end of a ruptured tissue. A ruptured tissue provides two ends of the tissue that were previously connected. A scaffold may be attached to one or both ends of a ruptured tissue by one or more sutures. A suture may be attached to a second bone site at or near the repair site. The suture may be attached to the second bone using a second anchor.

In a typical arthroscopic procedure, for instance of the ACL, the surgeon prepares the patient for surgery by insufflating the patient's knee with sterile saline solution. Several cannulas are inserted into the knee and used as entry portals into the interior of the knee. A conventional arthroscope is inserted through one of the cannulas so that the knee may be viewed by the surgeon remotely.

In surgical reconstruction of a tissue such as ACL the surgeon may drill a tibial tunnel and a femoral tunnel in accordance with conventional surgical techniques using conventional surgical drills and drill guides. A replacement anterior cruciate ligament graft is then prepared and mounted in the tibial and femoral tunnels, and secured using conventional techniques and known devices in order to complete the knee reconstruction.

The repair material is applied to a subject. The application to the subject involves surgical procedures. The following is an example of a surgical procedure which may be performed using the methods of the invention. The affected extremity is prepared and draped in the standard sterile fashion. A tourniquet may be used if indicated. The intra-articular lesion is identified and defined, the tissue ends are pre-treated, either mechanically or chemically, and if a scaffold is being used, the scaffold is introduced into the tissue defect. If the scaffold has not been pre-soaked in the repair material or if more repair material is desired, then the repair material is added to the scaffold. The scaffold may be reinforced by placement of sutures or clips. If no scaffold is used the tissue defect is coated directly with repair material. The post-operative rehabilitation is dependent on the joint affected, the type and size of lesion treated, and the tissue involved.

The temperature of the repair material may be regulated to optimize rapid gelatin in vivo. For instance, it is shown in the examples that different temperatures at the time of injection of the repair material into the body can influence the time required for gelatin to occur. In some embodiments of the invention the injection temperature is ideally between 24° C. and 30° C. 28° C. may be an optimal temperature in some settings to cause the quickest gelatin time. The injection temperature can be achieved by warming the solution to the optimal temperature immediately prior to injection.

The methods of the invention may be achieved using arthroscopic procedures. Standard arthroscopy equipment may be used. Initially, diagnostic arthroscopy may be performed to identify the appropriate repair site. If a scaffold is used it should be compressible to allow introduction through arthroscopic portals, incisions and equipment. The repair material can be placed in the repair site by direct injection. After the procedure the arthroscopic portals can be closed and a sterile dressing placed.

A subject includes, but is not limited to, any mammal, such as human, non-human primate, mouse, rat, dog, cat, horse or cow. In certain embodiments, a subject is a human.

The materials used in the invention are preferably biocompatible, pharmaceutically acceptable and sterile. As used herein, the term "biocompatible" refers to compositions (e.g. cells, tissues, matrices, etc.) that do not substantially disrupt the normal biological functions of other compositions to which they contact. In selected embodiments, the present invention also contemplates biocompatible materials that are both biodegradable and non-biodegradable.

As described above, each of the components of the repair material may be prepared sterilely. If however, one or more components is not retrieved or processed in a sterile manner then it can be sterilized prior to application to the subject. For instance the material (preferably without the cells) may be sterilized after production using gamma irradiation, ethanol, autoclave sterilization or other known sterilization methods.

As used herein, the term "pharmaceutically acceptable" means a non-toxic material that does not interfere with the effectiveness of the biological activity of the scaffold material or repair material. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art. The term "carrier" denotes an organic or inorganic ingredient, natural or synthetic, with which the scaffold material is combined to facilitate the application. The components of the pharmaceutical compositions also are capable of being co-mingled with the device of the present invention, and with each other, in a manner such that there is no interaction which would substantially impair the desired pharmaceutical efficacy.

In some embodiments the repair material composition is injectable. Injectable compositions may contain formulatory agents such as suspending, stabilizing and/or dispersing agents. Pharmaceutical formulations for injection may contain substances which increase the viscosity of the suspension, such as sodium carboxymethyl cellulose, sorbitol, or dextran. Optionally, the materials may also contain suitable stabilizers.

The collagen solution may be in the form of a liquid, gel or solid, prior to addition of the cells. Once the cells are added, the repair material will begin to increase in gelation for application to the body. If the collagen solution is a liquid or gel the cells may be directly added to the solution.

Alternatively, the collagen solution may be in powder form for constitution with a suitable vehicle, e.g., sterile pyrogen-free water, before use. Neutralization agent may be added before or after reconsistution. After the powder is reconsituted it is mixed with cells to form the repair material.

As used herein, the term "gel" refers to the state of matter between liquid and solid. As such, a "gel" has some of the properties of a liquid (i.e., the shape is resilient and deformable) and some of the properties of a solid (i.e., the shape is discrete enough to maintain three dimensions on a two dimensional surface.). A gel may be provided in pharmaceutical acceptable carriers known to those skilled in the art, such as saline or phosphate buffered saline. Such carriers may routinely contain pharmaceutically acceptable concentrations of salt, buffering agents, preservatives, compatible carriers and optionally other therapeutic agents.

An example of a gel is a hydrogel. A hydrogel is a substance that is formed when an organic polymer (natural or synthetic) is crosslinked via covalent, ionic, or hydrogen bonds to create a three-dimensional open-lattice structure which entraps water molecules to form a gel. A polymer may be crosslinked to form a hydrogel either before or after implantation into a subject. For instance, a hydrogel may be formed in situ, for example, at the repair site. In certain embodiments, the repair material forms a hydrogel within the repair site upon exposure to body temperatures.

The repair material, including the collagen solution and the cells will begin to set once it is created. The setting process can be delayed by maintaining cold temperatures or it may be accelerated by warming the mixture. In certain embodiments, a quick set composition of the repair material is provided. The quick set composition is capable of forming a set scaffold within 10 minutes of mixture when the material is exposed to temperatures of greater than 30° C. In some embodiments formation of the scaffold takes approximately 5 minutes at such temperatures. As discussed above, setting times can be further accelerated by optimizing injection temperatures. The quick set composition is achieved by preparing the collagen solution at concentrations and viscosities as described herein. The quick set nature can be further enhanced by the addition of non-toxic cross linking agents. Such compositions should be applied quickly to the tissue defect to sufficiently set before closure of the defect and surgery area.

The invention also includes in some aspects kits for repair of ruptured or torn articular tissue. A kit may include one or more containers housing the components of the invention and/or for collecting or storing blood or cells and instructions for use. The kit may be designed to facilitate use of the methods described herein by surgeons and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for human administration.

The kit may contain any one or more of the components described herein in one or more containers. As an example, in one embodiment, the kit may include instructions for mixing one or more components of the kit and/or isolating and mixing a sample (e.g., blood taken from a subject) and applying to a subject. The kit may include a container housing collagen. The collagen may be in the form of a liquid, gel or solid (powder). The collagen may be prepared sterilely, packaged in syringe and shipped refrigerated. Alternatively it may be housed in a vial or other container for storage. A second container may have buffer solution premixed prepared sterilely or in the form of salts. Alternatively the kit may include collagen and some buffer premixed and shipped in a syringe, vial, tube, or other container. The mixture may or may not include neutralization agent. The neutralization agent may be included in a separate container or may not be included in the kit.

The kit may have one or more or all of the components required to draw blood from a patient, process the sample into platelet concentrate or WBCs, and deliver the repair material to a surgical site. For instance, a kit for withdrawing blood from a patient may include one or more of the items required for such a procedure. For example, typically when an injection is to be made, the patient's skin is cleansed with a disinfecting agent, such as an alcohol wipe; then a second disinfecting agent, such as iodine or Betadine may be applied to the skin; an area is usually isolated with a tourniquet to restrict the blood flow within the artery or vein making the vessel more visible before the needle is inserted, a needle attached to a collection device, such as a vacutainer tube is injected through the patient's skin to withdraw the blood; the needle is then removed and wiped clean; and the puncture site is covered with an absorbent pad until after hemostasis.

The accessories included may be specifically designed to allow the practitioner to withdraw blood from the patient. For instance, the accessories may include one or more of the following a tourniquet, a skin penetration instrument, a device for housing blood, a collection tube, disinfecting agents or post-injection bleeding patches.

The skin penetrating instrument for initiation of blood flow may be a conventional device such as a needle. The needle may be single or double ended and may be of any gauge, preferably 21 or 23 gauge. It optionally has a safety sleeve, may be attached to a needle hub, and preferably is used with a conventional tube holder. The needle may also be part of a conventional syringe assembly including barrel and plunger. The needle may be part of a conventional blood collection set in which a penetrating needle having a grasping means, such as wings, is connected via a hub and tubing to a delivery needle for puncture of a septum of an evacuated tube.

The device for housing the blood may be any type of container for receiving the blood sample, such as, for example, a syringe barrel or it may be a device to which the blood sample is transferred following collection, for example a tube. Preferred devices for housing the blood are conventional tubes or vials having a closed end and an open end. Such tubes may have an internal volume of 100 µl to 100 ml. Devices to house the blood after it has been collected include for instance, vials, centrifuge tubes, vortex tubes or any other type of container. The device for receiving the blood may be an evacuated tube in which the open end is covered by a puncturable septum or stopper, such as a vacutainer tube. Evacuated tubes are generally used with a conventional tube holder and blood collection set for collection of multiple larger blood samples, and may contain any of a variety of conventional blood analysis additives, such as anticoagulants. Preferred anticoagulants are citrate and ethylenediaminetetra acetic acid (EDTA).

The plasma, which contains the platelets, may be separated from the whole blood. Any separation technique can be utilized, for example, sedimentation, centrifugation or filtration. Centrifugation can be carried out at about 500 g for about 20 minutes to obtain platelets. The supernatant, which contains the plasma, can be removed by standard techniques. Filtration can be carried out by passing the whole blood through a suitable filter that separates blood cells from plasma.

Optionally the kits may include disinfecting agents and post-injection bleeding patches. A means for sterilizing the patient's skin in the area of intended puncture, such as a disinfecting agent may be provided. A typical and conventional disinfecting agent is a piece of fabric commonly referred to as a gauze combined with a disinfectant. Some typical disinfecting agents include rubbing alcohol, antibacterial agents, iodine, and Betadine, which may or may not be provided with application pads in individually sealed packets. The post-injection bleeding patch can also vary from a relatively simple gauze pad plus adhesive strips, to a bandage.

When a blood draw is to be made, the practitioner may open the sealed kit; isolate a selected region of the patient's body, such as the lower arm, with the tourniquet to restrict the blood flow within the region and make the blood vessels more visible; clean the injection site with one or more of the sterilizing agents; attach the needle to the collection tube; inject the needle into the patient's blood vessel and collect the blood sample in the tube; withdraws the needle from the skin; and covering the puncture site with an absorbent pad. The blood may then be processed to produce a concentrate of platelets or white blood cells.

The kit may have a variety of forms, such as a blister pouch, a shrink wrapped pouch, a vacuum sealable pouch, a sealable thermoformed tray, or a similar pouch or tray form, with the accessories loosely packed within the pouch, one or more tubes, containers, a box or a bag.

The kit may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art.

The kit may also contain any other component needed for the intended purpose of the kit. Thus, other components may be a fabric, such as gauze, for removing the disinfecting agent after the sterilizing step or for covering the puncture wound after the sample is drawn. Other optional components of the kit are disposable gloves, a support for the device for holding blood after the sample is taken, adhesive or other device to maintain the fabric in place over the puncture wound.

The kit may include disposable components supplied sterile in disposable packaging. The kit may also include other components, depending on the specific application, for example, containers, cell media, salts, buffers, reagents, syringes, needles, etc.

The following examples are intended to illustrate certain aspects of certain embodiments of the present invention, but do not exemplify the full scope of the invention.

EXAMPLES

Example 1

Preparation of Collagen Solution and Testing of Properties

A. Minimal Gelation Achieved with Some Formulations

1. Innocoll: Aliquots of Innocoll Collagen (Starting pH=4.1) were Made.

Weights of aliquots were 0.380 mg collagen, pH=4.1. One half of the samples had 5 microliters $NaHCO_3$ added to bring pH to between 7.0 and 8.0 and one half were not neutralized. 300 microliters fetal bovine serum was added to each aliquot. All solutions were monitored for gelation at 37° C. for 30 minutes. The solutions remained liquid, with viscosities similar to that of water (approximately 1 centipoise). No increase in viscosity with time was noted over the hour long period.

Identical experiments with Innocoll aliquots at starting pH=2.5 were also performed. Additionally, experiments were performed using ratios of collagen:FBS of 1:1, 2:1 and 3:1. None of these materials produced a gelled product at 37° C. The solutions remained liquid, with viscosities similar to that of water (approximately 1 centipoise). No increase in viscosity with time was noted over the hour long period.

2. EPC: Collagen Slurry was Obtained from Elastin Products Company (Owensville, Mo.), Product Number C857, Lot Number 698, Lyophilized Type I Acid Soluble Collagen from Calf Skin.

Prepared according to the method of Gallop and Seifter Meth. Enzymol., 6, 635, (1963). In the method, fresh calf skin is extracted with 0.5 M NaOAc to remove non-collagen proteins. The soluble collagen is extracted with 0.075 M sodium citrate pH 3.7 and precipitated as fibrils by dialysis against 0.02 M $Na_2HPO_4$. The product was soluble in 0.01 M to 0.5 M acetic acid of maximum of 10 mg/ml and soluble in 0.075 M sodium citrate pH 3.7 and in dilute acetic acid 0.01 M to 0.5 M.

Before combining with the platelet component of the hydrogel, the collagen slurry was mixed with 0.1M HEPES Buffer 1M solution (Cellgro, Mediatech, Inc, Herndon, Va.), 10× Ham's F-10 medium (MP Biomedicals, LCC, Aurora, Ohio), Antibiotic-Antimycotic solution (Cellgro, Mediatech, Inc., Herndon, Va.) and sterile water. The collagen slurry was neutralized to a pH of 7.4 using 7.5% sodium bicarbonate (Cambrex BioScience Walkersville, Inc., Walkersville, Md.). Mixtures of collagen-PRP were tested using ratios of collagen:FBS of 3:1. None of these materials produced a gelled product at 37° C. The solutions remained liquid, with viscosities similar to that of water (approximately 1 centipoise). No increase in viscosity with time was noted over 1 hour or overnight.

3. SERVA: Collagen Slurry was Obtained from Serva, Product Number 47256, Lot Number 14902 Type I Rat Tail Collagen Solution at 4 mg/ml in 0.1% Acetic Acid (Heidelberg Germany.

The collagen slurry was mixed with 0.1M HEPES Buffer 1M solution (Cellgro, Mediatech, Inc, Herndon, Va.), 10× Ham's F-10 medium (MP Biomedicals, LCC, Aurora, Ohio), Antibiotic-Antimycotic solution (Cellgro, Mediatech, Inc., Herndon, Va.) and sterile water. The collagen slurry was neutralized to a pH of 7.4 using 7.5% sodium bicarbonate (Cambrex BioScience Walkersville, Inc., Walkersville, Md.).

Mixtures of collagen-PRP were tested using ratios of collagen:FBS of 3:1. This material did not produce a gelled product at 37° C. The solutions remained liquid, with viscosities similar to that of water (approximately 1 centipoise). No increase in viscosity with time was noted over 1 hour or overnight.

4. VITROGEN: Collagen Slurry was Obtained from Cohesion Technologies (Palo Alto, Calif.). Vitrogen 100 Slurry, Lot Number C101636 with a Collagen Concentration of 3.1 Mg/Ml was Also Tested.

Vitrogen Collagen In Solution is 99.9% pure collagen as judged by SDS polyacrylamide gel electrophoresis in conjunction with bacterial collagenase sensitivity and silver staining techniques. The solution is 95-98% Type I collagen with the remainder being comprised of Type III collagen. Vitrogen Collagen In Solution is a native collagen as judged by polarimetry and trypsin sensitivity, although it does contain a low percentage of nicked or shortened helices.

The collagen slurry was mixed with 0.1M HEPES Buffer 1M solution (Cellgro, Mediatech, Inc, Herndon, Va.), 10× Ham's F-10 medium (MP Biomedicals, LCC, Aurora, Ohio), Antibiotic-Antimycotic solution (Cellgro, Mediatech, Inc., Herndon, Va.) and sterile water. The collagen slurry was neutralized to a pH of 7.4 using 7.5% sodium bicarbonate (Cambrex BioScience Walkersville, Inc., Walkersville, Md.). Mixtures of collagen-PRP were tested using ratios of collagen:FBS of 3:1. This material did not produce a gelled product at 37° C. For the first thirty minutes, the solutions remained liquid, with viscosities similar to that of water (approximately 1 centipoise). No significant increase in viscosity with time was noted until one hour had passed.

5. Wake Forest Collagen Testing: Collagen Solutions were Made from Pig Skin. The Skin was Washed with Water and the Hair and Subcutaneous Fat Removed. The Skin was Minced and Further De-Fatted with Acetone and Washed with Deionized Water.

The minced pieces were soaked in 10% NaCl at 4° C. for 24 hours then soaked in a citrate buffer (pH 4.3) for 48 hr and homogenized in 0.5 M acetic acid at 4° C. The homogenate was then digested with pepsin at 4° C. for 24 hr and centrifuged. NaCl equivalent to 5% w/v added to salt-out atelo-collagen and the collagen washed with phosphate buffer and dissolved in 0.5 M acetic acid and dialyzed.

The aliquots of collagen were held on ice until they were mixed with FBS and Ham's F12. All solutions had a pH between 7.0 and 7.5. 150 microliters of FBS and 50 microliters Hams F12 were added to each tube, mixed with vortexer, and placed in water bath at 37° C. One of five aliquots gelled at 7 minutes. None of the other four gelled over the 30 minute time period of the test. The tests were repeated for the 4 collagen samples that did not gel. None of the repeated samples gelled during the 30 minute time frame.

In order to confirm the accuracy of the gelation of the single sample that produced a gelled product, a second trial was conducted to repeat the study on the collagen type that did set in first trial. In the second trial no gelation was observed, even after 3 hours at 37° C. The experiment was attempted again with collagen and FBS only. The following was observed: ratio of 2:1 collagen:FBS produced no gelation and ratio of 3:1 collagen:FBS did gel when placed in water bath at 37° C. (gel softened over the remaining hour). Repeat testing of this collagen type showed inconsistent gelation which softened over time rather than continuing to hold shape.

B. Rapid Gelation Observed with Formulations of the Invention.

Pig Patellar Tendons were minced, placed into 10% NaCl solution to obtain salt-solubilized collagen. The collagen was homogenized and centrifuged. The supernatant was aspirated and PRP was added. 5 of the 6 samples tested resulted in rapid gelation when exposed to temperatures of 37° C. In one sample no gelation was obtained.

Rat tail tendons were harvested. All steps were carried out using sterile technique and solutions. Salt solubilized tendon fascicles were centrifuged, the supernatant removed and replaced with acetic acid and enzyme to solubilized the collagen further. The resultant collagen slurry had a pH=3.0. Aliquots were made and neutralized with $NaHCO_3$ to pH=7.0. 500 microliters of PRP were added to aliquots of 1 cc collagen slurry and vortexed (all on ice prior to mixing). The mixture was placed in a water bath at 37° C. Each of the samples formed a soft set gel within 5 minutes (partial gelation).

Additional aliquots with collagen slurry, and buffer containing F10 culture media and antibiotics were tested. 150 microliters serum was added after neutralization with $NaHCO_3$ and NaOH. The collagen gel set in 5 minutes at 37° C. on initial four tests. The fifth sample did not gel. Repeat testing showed most slurries made with this protocol would set, but not all (approx 60%).

The collagen solution was then prepared using different buffer components. With the addition of HEPES buffer to help maintain pH between 7.0 and 8.0 and adjusting other components of buffer (antibiotics, F10 and sterile water) to bring osmolarity to within 280 to 350 mOsm/kg, we were able to get reliable gelation within 10 minutes for over 90% of aliquots tested in trials.

C. Cell Viability in Collagen/Buffer Mixture:

Drop testing: One million pig primary outgrowth ACL cells were trypsinized and added to a neutralized collagen slurry to produce a density of cells of $1\times10^5$ cells/cc. FBS was added to produce a ratio of 3:1 and 4:1 collagen:FBS. Drops were placed onto individual wells of a tissue culture plate. The next day, some cell spreading was seen from 2 of 3 gels. At day 4, cells were growing in 1 of 3 gels.

D. Evaluation of Whether the Proliferation of Pig ACL Cells Seeded in Collagen Gels is Affected by the Final Collagen Concentration of the Gels.

The following methods were performed:

Targeted cells were seeded at $5 \times 10^5$ cells/ml. The final collagen concentrations in the gels was 3.4, 1.7 and 0.8 mg/ml. These final concentrations were calculated based on slurry #50's collagen concentration (10.5 mg/ml), the fact that the slurry will be used at full, ½ and ¼ strengths and how much the slurry is diluted when making the gels. Time points were taken at 1, 5 and 10 days, resulting in a total of 9 data points (time/collagen concentration). Each data point was run in quadruplicate with 2 cell-free controls at each data point.

The total amount of cell-seeded gels was 36 ml. Enough gel for each data point was made using 1.5 ml slurry and 1.5 ml PRP. The PRP needed for data points was 13.5 ml (1.5×9) and PRP needed for cell-free gels was 2.2 ml. Total PRP needed was 15.7 ml.

The number of cells needed was $13.5 \times 5 \times 10^{5 \times 3}$ (since PRP is diluted ~3 times when making the gel) which results in $202.5 \times 10^5$ (or $20.3 \times 10^6$) cells.

Day 1—Make Cell-Seeded Gels:

The cells were trypsinized, centrifuged, resuspended in complete media and counted to make sure there are enough cells for the assay. The cell solution was centrifuged and the cells were resuspended in PRP such that the cell concentration in (at least) 13.5 ml PRP was $15 \times 10^5$ cells/ml (PRP was diluted ~3 times when making gels).

The gels were made using PRP with or without cells depending on the case. 1 ml of gel was aliquoted on 42 wells of 12-well plates and placed in an incubator. After 1 hour the complete media was added on top of gels and the cells were equilibrated in gels for ~24 hours.

Days 2, 6 and 11—MTT Assay at Days 1, 5 and 10:

The plates were removed from the incubator and the media was aspirated. With a sterile spatula all gels were transferred into new 12-well plates. 1 ml of MTT (3-(4,5-dimethylthiazol-2-yl)-2,5-diphenyltetrazolium bromide) dye was added to each well of time point 1-day. The gels were incubated for 3 hours. The MTT solution was aspirated off and discarded. 1 ml of sterile 1×DPBS was added to each well. Plates were placed on a rotating platform and allowed gentle rinsing for 30 minutes. 200 µl aliquot was removed from each well and the absorbance was read for persistence of color removal. The remainder of DPBS was removed and the DPBS steps were repeated twice. If absorbance levels from DPBS after $3^{rd}$ rinse are still above 0.1 a $4^{th}$ rinse may be performed. Using a sterile spatula, the gels were detached from sides/bottom of wells and transferred to new 3 ml tubes. 1 ml of detergent (20% SDS/Formamide) was added. The mixture was incubated for 5 hours. The tubes were removed from the incubator, briefly vortexed on high for ~5 seconds and samples were spun down at 1500 rpm for 5 minutes. 200 µl of supernatant was transferred to 96-well plate and the absorbance was read.

Results

Figure 10:
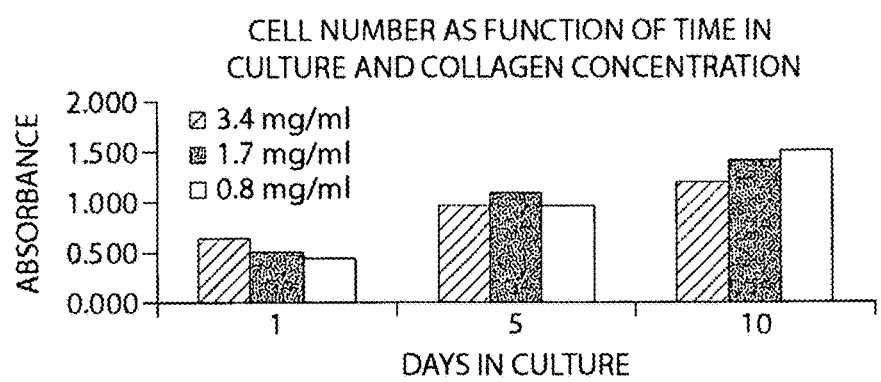
FIG. 10 is a graph depicting cell number as a function of time in culture and collagen concentration.

Cell proliferation in vitro was seen in final collagen concentrations of 0.8 to 3.4 mg/ml (starting collagen concentrations were 10.5, 5.3 and 2.6 mg/ml). Cell number increased with time in culture for all groups between 1 and 10 days. The results are shown in FIG. 10.

E. Viscosity of Collagen/Buffer Mixture:

At cold temperature viscosity was 70 cp and after heating to 37° C., the viscosity was assessed at 3200 cp at shear rate of 1/sec. At slower shear rate (0.3/sec), viscosity at 37° C. was determined to be 6,000-11,000 cp.

F. Ability of Collagen/Buffer Solution to Stimulate Platelets to Release Growth Factors:

The collagen/buffer mixture (described in (B) above) was added to a platelet mixture and the subsequent release of growth factors from the platelets measured using an ELISA assay. The thrombin-free preparations were compared to a preparation using bovine thrombin to stimulate platelet release of growth factors. Similar growth factor release was seen using the collagen slurry as a platelet activator as with the bovine thrombin as an activator. The results are described in Example 2.

G. Sterility

Multiple in vitro assays have been performed using the Collagen/Buffer solution described above in (B) with no evidence of bacterial or fungal contamination or infection in any of the samples tested out to 10 days in vitro and up to 9 weeks in vivo.

H. In Vivo Testing of Collagen/Buffer Solution

Figure 9:
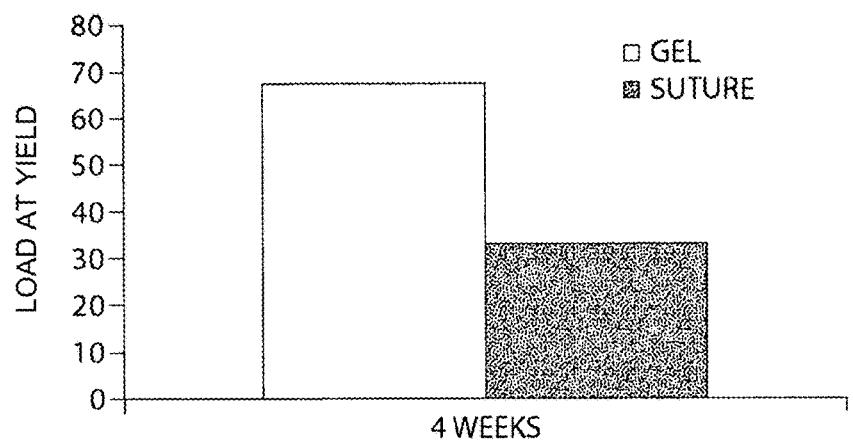
FIG. 9 is a graph depicting results of in vivo pig total ACL transection treated with collagen slurry/buffer mixed with animal's own PRP in the operating room, wherein the mixture is injected into the gap between the cut ligament ends.

Model: Pig total ACL transection was treated with collagen slurry/buffer mixed with animal's own PRP in the operating room. The mixture was injected into the gap between the cut ligament ends. Adding the Collagen/Buffer solution to the autologous PRP resulted in more than doubling of the yield strength of the healing ligament after four weeks in vivo compared with the use of sutures alone for the repair. FIG. 9 is a graph depicting results of the in vivo pig total ACL transection treated with collagen slurry/buffer.

Example 2

In this Example, type I collagen was used to stimulate activation of the fibrin clotting mechanism and platelet activation. Initially, we tested collagen to determine if it would result in more sustained release of two growth factors used as markers of platelet function, namely TGF-β1 and PDGF-αβ, when compared with the use of exogenous thrombin. Secondly, we tested whether the amount of this release would be dependent on the platelet concentration in the PRP. The release profiles of these growth factors from three types of collagen-PRP gels were compared with the release profile from a PRP clot created with exogenous bovine thrombin over 10 days. Additionally, we determined whether the growth factor release from collagen-activated PRP hydrogels would cause a physiologic changes in ACL cells in terms of 1) cellular metabolism of growth factors, 2) cellular proliferation within the gels and 3) cell-mediated gel contraction.

Materials and Methods

Preparation of Platelet-rich Plasma: Centrifugation Method

Three hundred milliliters of whole blood was drawn from each of five hematologically normal volunteers meeting all criterion of the American Association of Blood Banks (Food and Drug Administration, Center for Biologics Evaluation and Research). Blood was collected in a bag to contain 10% acid-citrate dextrose at the Center for Blood Research (Boston, Mass.). Forty five ml of whole blood from each patient was centrifuged for 6 minutes at 200 g (Beckman GS-6 Centrifuge, Fullerton, Calif.). The supernatant was aspirated and collected as PRP. Two additional groups of PRP samples were made using the Harvest Smart PreP2 System (Harvest Technologies, Plymouth, Mass.) as noted below.

PRP Preparation Using the Smart PreP2 System: Platelet Concentrate Method

PRP was also produced using the Harvest Smart PreP2 System (Harvest Technologies, Plymouth, Mass.). PRP was produced by the method recommended by the manufacturer. Fifty four cc of whole blood was anticoagulated using 10% acid-citrate dextrose and transferred to the blood chamber of the device, and 2 ml ACD was placed in the plasma chamber of the disposable blood processor (DP). The blood is centrifuged in a container with a floating shelf designed to rise to just below the buffy coat/red blood cell interface. Following the separation of plasma from the red blood cells, the centrifuge slows, and the platelets, plasma and white blood cells are decanted into the plasma chamber. When the plasma decant is complete, a second centrifugation step is used to form a pellet of platelet concentrate in the bottom of the plasma chamber. The plasma chamber contains the platelet concentrate (a button-like precipitate) and platelet poor plasma (supernatant). The complete process is entirely automatic and completed in approximately 14 minutes. Approximately ⅔ of the platelet poor plasma (PPP) is removed. The platelet concentrate (PC) is then resuspended in the remaining PPP.

PRP Preparation Using the Smart PreP2 System: RBC-Reduced Method

PRP in this group was prepared using the platelet concentrate as above with an additional step to remove the majority of erythrocytes in the PRP. To accomplish this, 30 ml of platelet concentrate from each patient was centrifuged in the Smart PreP2 system for an additional 2 minutes. The supernatant is then aspirated and kept as the RBC-reduced (RBC-red) PRP.

Samples of whole blood and platelet rich plasma preparations were analyzed for complete blood count with differential to determine initial and final platelet and white blood cell concentrations (Table 1 and Table 2)

TABLE 1

Platelet counts for each PRP preparations.

| Patient # | Baseline Plt Count | Centrifuged (% of baseline) | PC (% of baseline) | RBC Reduced (% of baseline) |
|---|---|---|---|---|
| 1 | 316 | 434 (137%) | 919 (291%) | 1287 (407%) |
| 2 | 204 | 286 (140%) | 860 (422%) | 1000 (490%) |
| 3 | 194 | 249 (128%) | 715 (368%) | 794 (409%) |
| 4 | 318 | 573 (180%) | 1215 (382%) | 1385 (436%) |
| 5 | 246 | 479 (195%) | 1057 (430%) | 1131 (460%) |
| Avg | 256 | 404 (158%) | 953 (373%) | 1119 (438%) |

TABLE 2

Differential in total cells/microliter.

| Patient # | Baseline | | Centrifuged | | PC | | RBC Reduced | |
|---|---|---|---|---|---|---|---|---|
| | WBC | GRN | WBC | GRN | WBC | GRN | WBC | GRN |
| 1 | 3,500 | 2,000 | 1,400 | 100 | 7,700 | 700 | 7,600 | 300 |
| 2 | 3,900 | 2,600 | 1,000 | 0 | 7,600 | 1,000 | 5,400 | 200 |
| 3 | 6,700 | 4,800 | 500 | 0 | 13,600 | 5,600 | 4,900 | 600 |
| 4 | 5,500 | 3,300 | 1,100 | 100 | 16,000 | 4,300 | 8,000 | 1,300 |
| 5 | 5,000 | 3,300 | 500 | 0 | 11,000 | 3,300 | 6,100 | 700 |
| Avg | 4,920 | 3,200 | 900 | 40 | 11,180 | 2,980 | 6,400 | 620 |

Manufacture of Acid-Soluble Collagen Used in the Hydrogels

Rat tails were obtained from control breeder rats undergoing euthanasia for other Institutional Animal Care and Use Committee approved studies. The rat-tail tendons were sterilely harvested, minced, and solubilized in an acidified pepsin solution to obtain the acid soluble collagen. Collagen content within the slurry was adjusted to greater than 5 mg/ml using 0.01N hydrochloric acid. Before combining with the platelet component of the hydrogel, the collagen slurry was mixed with 0.1M HEPES Buffer 1M solution (Cellgro, Mediatech, Inc, Herndon, Va.), 10× Ham's F-10 medium (MP Biomedicals, LCC, Aurora, Ohio), Antibiotic-Antimycotic solution (Cellgro, Mediatech, Inc., Herndon, Va.) and sterile water. The collagen slurry was neutralized to a pH of 7.4 using 7.5% sodium bicarbonate (Cambrex BioScience Walkersville, Inc., Walkersville, Md.).

Platelet Activation: Exogenous Thrombin Group

Five milliliters of calcium chloride (100 mg/ml) were added to 5,000 IU bovine thrombin (Bovine Thrombin—JMI, Jones Pharma Inc, Bristol, Va.) to produce a 1,000 IU/ml solution. 80 ml of the thrombin solution was then added to 720 ml of the Platelet Concentrate group for each patient. Duplicate samples of the mixture were injected into 2 ml centrifuge tubes and allowed to form a clot. Clots were weighed and placed in a 37° C. incubator for 20 minutes prior to transfer to sterile 12-well plates. One milliliter of Dulbecco's Modified Eagle's Medium (DMEM, Cat#10013CV, Cellgro, Mediatech, Inc., Herndon, Va.) with 2% antibiotics (Cellgro, Mediatech, Inc., Herndon, Va.) was added to each clot. Samples were cultured in a 37° C. humidified incubator.

Platelet Activation: Collagen Groups

For each sample, an equal volume of PRP and collagen hydrogel were mixed and heated to 30° C. over 1 minute. Duplicate samples of each collagen-PRP mixture were injected into two 2 ml centrifuge tubes. This was repeated for all test groups. Gels were weighed and placed in a 37° C. incubator for 20 minutes prior to transfer to sterile 12-well plates. One mL of DMEM with 2% antibiotics (Cellgro, Mediatech, Inc., Herndon, Va.) was added to each gel. Samples were cultured in a 37° C. humidified incubator.

Additionally, a collagen hydrogel-only (no PRP) was also made and the release evaluated at 12 hours, 1 day, 3 days and 5 days.

Measurement of Growth Factor Levels:

At each time point (12 hours, 1, 3, 5, 7 and 10 days) media was aspirated from around each sample and replaced with 1 mL of fresh media (serum-free DMEM with 2% antibiotics added). Media samples were stored in cryovials in a −80° C. freezer until all samples were collected. Concentrations of human PDGF αβ, TGF $β_1$ and VEGF were determined using the commercially available Quantikine colorimetric sandwich ELISA kits (R&D Systems, Minneapolis, Minn.). Assays were performed in duplicate on media samples as described in the instructions of the manufacturer. Dilutions of 1:20 (12 hour samples) and 1:10 (day 1, day 3, day 5, day 7 and day 10 samples) were used for samples in the PDGFαβ assay; a dilution of 1:10 was used for all samples in the TGF $β_1$ assay; and no dilution was used for the VEGF assay. These dilutions were accounted for in analysis.

The media concentration of each growth factor was determined using the ELISA kit after performing the dilutions described above. The plasma total TGF $β_1$ was assayed after acid activation of the plasma by adding 20 microliters of 1N HCl to 40 microliters of media sample. The reaction solution was mixed and incubated at room temperature for 10 minutes before it was neutralized by with microliters of 1.2N of NaOH/0.5 M HEPES. It was further diluted to 1:10 in calibrator diluent before it was added to the ELISA plate.

For each growth factor, the standard curve was produced by a 2-fold serial dilution of a known concentration of growth factor provided in the kit to make final concentrations of 0, 31.2, 62.5, 125, 250, 500, 1000 and 2000 pg/ml. The color change of the final reaction was measured at a wavelength of 450 nm for the optical density and the standard curve concentrations vs absorbances was linear using a four parameter logistic fit curve. The reported minimal detection limit of TGF-β1 was 4.61 pg/ml, 9.0 pg/ml for VEGF and 1.7 pg/ml for PDGF-αβ.

Due to the media sampling technique described above, growth factor concentrations reported in the results section reflect the growth factor release in the time period since the prior media change. For 12 hours and day 1, this is a 12 hour release and for day 3, day 5 and day 7, it is a 48 hour release.

Analysis: The cumulative TGFb release was measured after 1, 5 and 10 days of culture of gels seeded with $3 \times 10^5$ ACL cells. The effect of the seeded cells on TGFb release was calculated by subtracting the cumulative TGFb release from cell-free gels at each time point from the cumulative TGFb release from the cell seeded gels at the same time point (both values calculated per ml gel to account for possible differences in gel sizes during gel manufacture).

The cumulative PDGF release was measured after 1, 5 and 10 days of culture of gels seeded with $3 \times 10^5$ ACL cells. The effect of the seeded cells on PDGF release was calculated by subtracting the cumulative PDGF release from cell-free gels at each time point from the cumulative PDGF release from the cell seeded gels at the same time point (both values calculated per ml gel to account for possible differences in gel sizes during gel manufacture).

The cumulative VEGF release was measured after 1, 5 and 10 days of culture of gels seeded with $3 \times 10^5$ ACL cells. The effect of the seeded cells on VEGF release was calculated by subtracting the cumulative VEGF release from cell-free gels at each time point from the cumulative PDGF release from the cell seeded gels at the same time point (both values calculated per ml gel to account for possible differences in gel sizes during gel manufacture).

Effect on Cell Proliferation: MTT Assay

Collagen-PRP hydrogels and thrombin-PRP clots containing $3 \times 10^5$ cells/ml were prepared as follows. Primary outgrowth human ACL cells were cultured from explants obtained from 2 women (ages 15 and 22) undergoing ACL reconstruction. Explants were cultured in media containing 10% FBS (HyClone Inc., Cat. #16777-006, South Logan, Utah), 1% AB/AM (Media Tech, Inc., Cat. #30004067, Herndon, Va.) and media changed 2 times per week until confluent cultures established. The cells were trypsinized and replated once onto T-75 flasks until use. First passage ACL cells were trypsinized, resuspended in complete media, counted and four pellets containing $6 \times 10^6$ cells were prepared in 15 cc centrifuge tubes. Each pellet was resuspended in 6.5 cc of one of four solutions: PRP prepared by centrifugation, PC PRP, RBC-reduced PRP or normal phosphate buffered saline (EMD Chemicals, Cat. #: B10241-34, Gibbstown, N.J.).

Cell proliferation was measured using the MTT (3-(4,5-dimethylthiazol-2-yl)-2,5-diphenyltetrazolium bromide) assay; this assay measures the ability of a cell's mitochondrial dehydrogenase enzymes to convert yellow, soluble MTT salt into purple formazan salt. The MTT was prepared at a concentration of 1 mg/ml in serum-free DMEM from the sterile stock MTT solution (5 mg/ml PBS). After the media was removed from each well, a sterile spatula was used to transfer each gel to a sterile 12-well plate; this allowed only those cells proliferating in the gel to be labeled by the MTT. 1.2 ml of MTT solution (1 mg/ml) was added to each well. Each gel was fully immersed in the MTT solution. After the MTT was added, the plates were incubated for 3 hours (37 C, 5% CO2). Subsequently, the excess MTT solution was removed and 1 ml of sterile 1×PBS was added to each well, placed on a vertical agitator (Fisher Scientific Clinical Rotator, 100 rpm) and left to rinse at room temperature for 30 minutes. Afterwards, 150 microliters of PBS was removed from each well, transferred to a sterile 96-well plate and the absorbancies read at 562 nm. This rinse was repeated until all PBS aliquots read absorbencies under 0.100 nm. All PBS was then removed and each gel transferred with a sterile spatula into a sterile 3.0 ml centrifuge tube. The gels and ? formazan crystals were then dissolved by adding 1 ml of a detergent containing 20% aqueous SDS/formamide (1:1 volume ratio) to each tube and incubating for 5 hours in a 37 C water bath. Finally, the tubes were centrifuged for 5 minutes at 1500 rpm, and aliquots of the supernatant from each tube (200 microliters) were then transferred onto a sterile 96-well plate. The absorbencies were measured at 562 nm, and the cell concentrations determined.

We were unable to assess the effect of the PC on cell proliferation as the control readings for the cell free gels were higher than the absorbance reader tolerance, likely due to the high number of red blood cells in this PRP preparation.

MTT controls were prepared identically to the method above differing solely in their absence of cells. MTT protocol was again performed at 1, 5, and 10 days allowing the controls to be determined and when applied to the MTT results from the cell seeded hydrogels, the effect of each gels' cells isolated and compared.

Collagen Gel Contraction Assay

Both fibroblast and PRP-mediated collagen gel contraction was assessed. The degree of contraction of collagen gels was determined by measuring the area of each gel over time in culture. Every two days (day 1, day 3, day 5 and day 7), the length and width at the gel midpoint was measured using a millimeter ruler and recorded. Comparisons between fibroblast-seeded gels with and without PRP and cell-free gels with and without PRP were made.

Statistical Analysis

Two-factor ANOVA for group and time was used to compare the growth factor release of the collagen-PRP hydrogels with those of the thrombin-PRP clots, with values of $p<0.05$ considered statistically significant. Bonferroni-Dunn post hoc testing was used to determine the significance of observed differences between groups in a pairwise analysis.

Results

Figure 2:
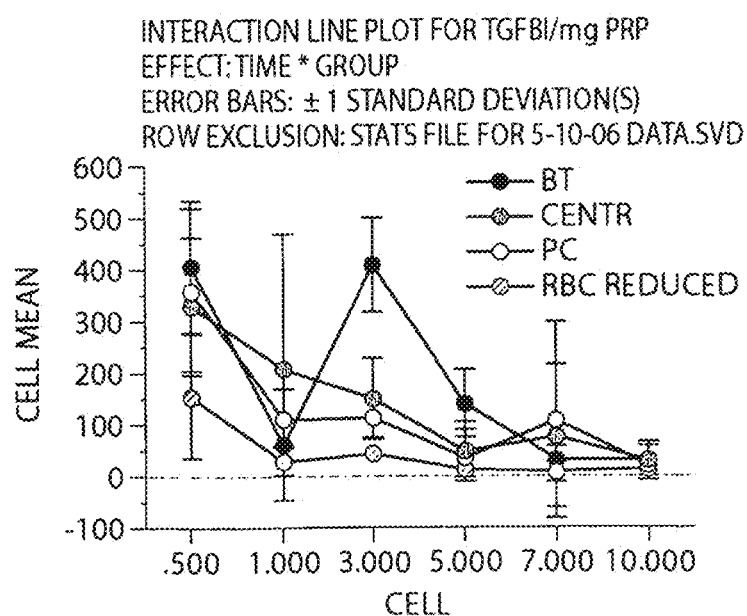
FIG. 2 is a graph depicting release of TGF-β1 over time from bovine thrombin-activated (BT) and collagen-activated (CENTR, PC and RBC Reduced platelet concentrate) PRP hydrogels.

Hypothesis One: That the Use of Collagen as a Platelet Activator would Result in a More Sustained Release of Growth Factors from a PRP Gel In both the bovine thrombin-activated and collagen-activated PRP gels, the highest release of PDGF-αβ and TGF-β1 occurred in the first twelve hours (FIGS. 1 and 2). For time points greater than 3 days (delayed release), there was no difference in release of PDGF-αβ or TGF-β1 between the bovine thrombin-activated and collagen-activated groups. In both groups, the release of PDGF-αβ at 10 days, was higher than 1.9 ng/ml and for TGF-β1, the release at 10 days was higher than 15 ng/ml for both bovine-activated and collagen-activated PRP gels.

The results are shown in FIGS. 1 and 2. FIG. 1 is a graph depicting the release of PDGF-αβ over time from bovine thrombin-activated (BT) and collagen-activated (Centr, PC and RBC Reduced) PRP hydrogels. The release of TGF-β1 over time from bovine thrombin-activated (BT) and collagen-activated (Centr, PC and RBC Reduced) PRP hydrogels is shown in FIG. 2.

Hypothesis Two: That Platelet Number in the PRP would Affect the Release of Growth Factors from the PRP Gels.

There was a strong positive correlation between platelet count in the PRP preparation and TGF-β1 and PDGF-αβ release. For TGF-b, this was strongest at the 12 hour time point (r2=0.608) and remained positive at the 10 and 12 day time points (r2>0.35 for both correlations). A positive correlation was also found between platelet concentration in the gel and PDGF release, particularly at the 12 hour time point (r2>0.35). The results are shown in FIGS. 3 and 4.

Figure 3:
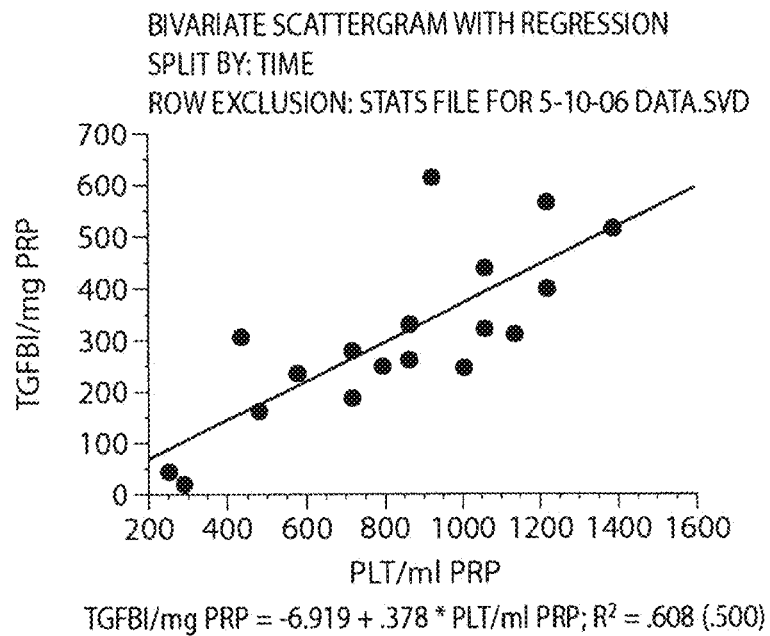
FIG. 3 is a graph depicting TGF-β1 release as a function of platelet concentration in the PRP at 12 hours after platelet activation.
Figure 4:
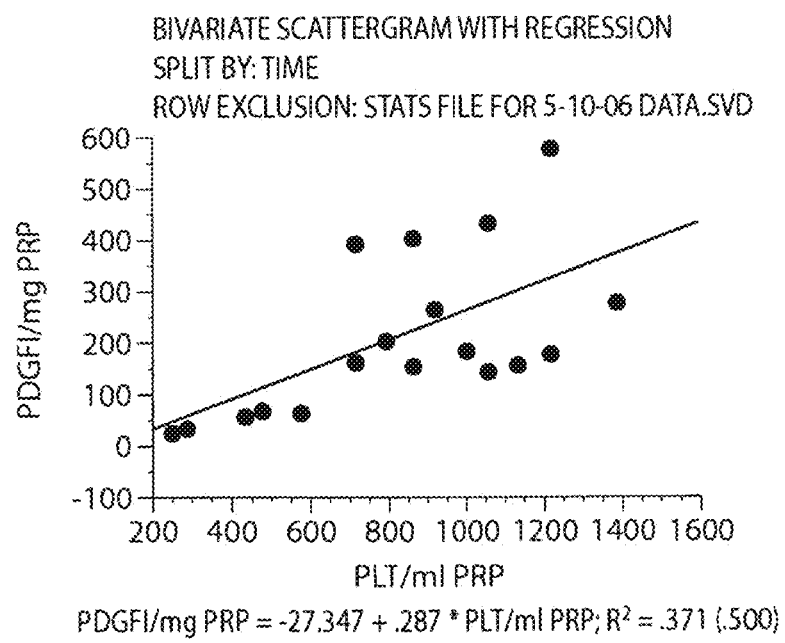
FIG. 4 is a graph depicting PDGF-αβ release from the PRP gels as a function of platelet concentration in the PRP at 12 hours after platelet activation.

TGF-β1 release as a function of platelet concentration in the PRP at 12 hours after platelet activation is depicted in FIG. 3. FIG. 4 shows the PDGF-αβ release from the PRP gels as a function of platelet concentration in the PRP at 12 hours after platelet activation.

There was a strong positive correlation between platelet concentration in the gels and gel contraction at all time points (r2>0.64 at all time points), suggesting the contraction of the gels was platelet-mediated. Much lower correlations were found between granulocyte counts and gel contraction (r2<0.30 for all correlations) and was more likely due to the correspondence between platelet and granulocyte content in the PRP (r2=0.35).

Hypothesis Three: That the Growth Factor Release from Collagen-Activated PRP Hydrogels would Cause a Physiologic Changes in ACL Cells in Terms of 1) Cellular Metabolism of Growth Factors, 2) Cellular Proliferation within the Gels and 3) Cell-Mediated Gel Contraction.

1) Cellular Metabolism of Growth Factors in Collagen-PRP Gels

Less TGF-β1 and PDGF-αβ eluted from the cell-seeded gels than from the cell-free gels, suggesting the cells were metabolizing the TGF-G1and PDGF-αβ. There was no significant difference among groups (two-factor ANOVA with p>0.2 for group and p>0.4 for time). In contrast, more VEGF eluted from the cell-seeded gels, suggesting the cells were producing additional VEGF. There was no significant difference between the groups, however VEGF release did increase over time in culture (two factor ANOVA with p>0.15 for group and p<0.02 for time, BFD post-hoc testing p<0.012 for comparison between 1 and 10 day values). On average, more than 4 times as much VEGF was eluted from the cell-seeded gels than from the cell-free gels.

Figure 5:
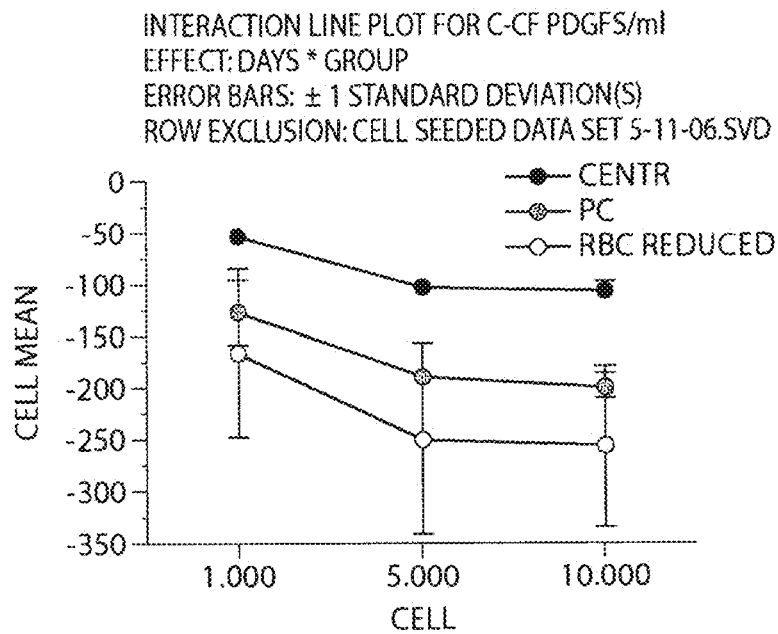
FIG. 5 is a graph depicting PDGF-αβ elution over time from the cell-seeded PRP hydrogels. The negative values over time suggest cell-based consumption of the PDGF-αβ.
Figure 6:
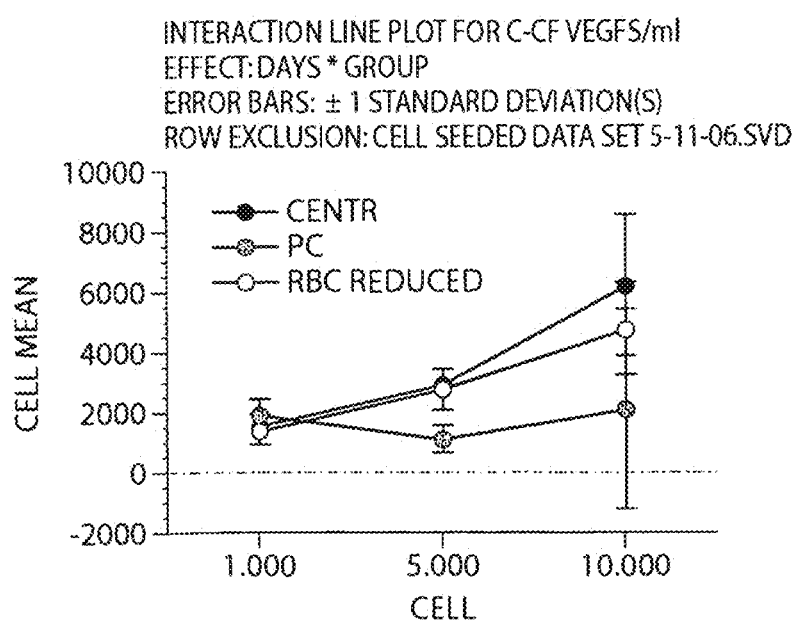
FIG. 6 is a graph depicting VEGF elution over time from the cell-seeded PRP hydrogels. The positive trend over time suggests continuing greater production than consumption of the VEGF by the ACL cells.

The PDGF-αβ elution over time from the cell-seeded PRP hydrogels is shown in FIG. 5. The negative values over time suggest cell-based consumption of the PDGF-αβ. VEGF elution over time from the cell-seeded PRP hydrogels is shown in FIG. 6. The positive trend over time suggests continuing greater production than consumption of the VEGF by the ACL cells.

2) Cellular Proliferation within the Gels

Figure 7:
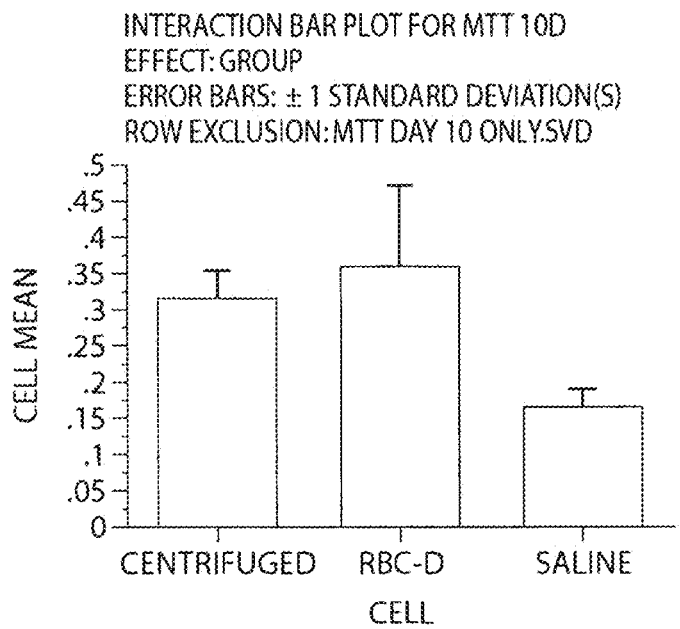
FIG. 7 is a graph depicting cellular proliferation within the gels.

The incorporation of centrifuged or RBC-depleted platelet rich plasma in the collagen hydrogel resulted in a significant increase in cell number within the gels over 10 days of culture in vitro (one factor ANOVA, p<0.009) with an almost two-fold increase in cell number between saline (0.165+/−0.03 mean+/−sd) and centrifuged (0.316+/−0.04) groups and a more than 2-fold difference between the saline and RBC-depleted (−0.359+/−0.11) groups. No significant difference was seen between the centrifuged and RBC-D groups (BFD, p>0.40). The results are shown in FIG. 7.

3) ACL Cell-Mediated Gel Contraction

Figure 8:
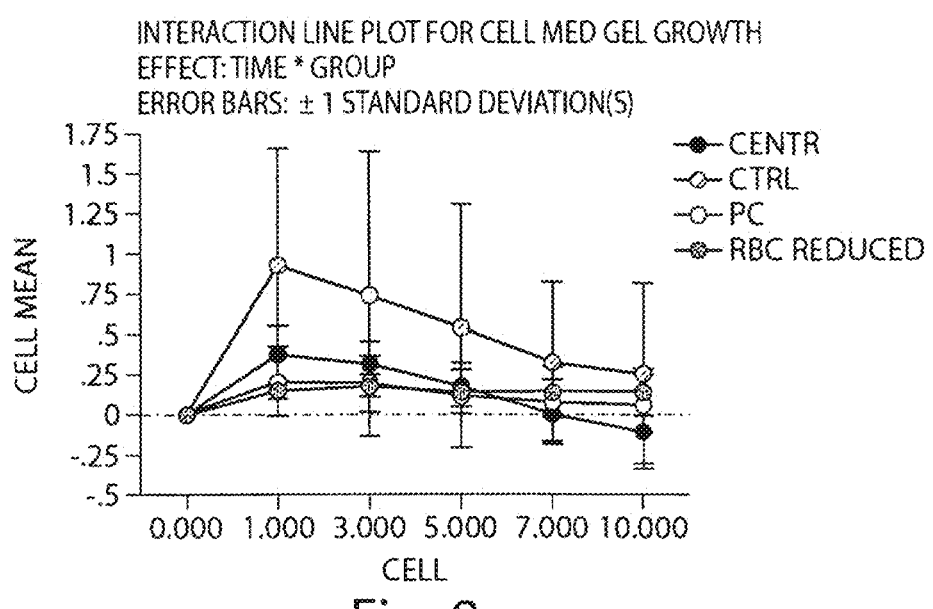
FIG. 8 is a graph depicting results of ACL cell-mediated gel contraction.

The addition of ACL cells to the gels resulted in a stabilization of gel size during the 10 days of culture (two factor ANOVA, p<0.006 for time and p<0.001 for group, BFD p>0.003 for all comparisons between time points except between days 0 and 1 where p<0.001). The results are shown in FIG. 8.

Effect of Growth Factor Consumption on Gel Contraction

There was a positive correlation between gel contraction and TGF-β1 consumption, that is, the more TGF-β1 consumed by the cells, the greater the cell-mediated contraction of the gels. This was most significant in the RBC reduced group (r2=0.38) and less so in the PC (r2=0.24) and Centrifuged (r2=0.11) groups. There was also a positive correlation between gel contraction and PDGF consumption, that is, the more PDGF consumed by the cells, the greater the cell-mediated contraction of the gels. This was most significant in the Centrifuged (r2=0.46) and PC groups (r2=0.42) than in the RBC red group (r2=0.27). In contrast, the more VEGF produced by the cells, the greater the cell-mediated contraction of the gels (r2=0.38). This was only significant in the Centrifuged group (r2=0.38) and was not seen in the PC (r2=0.11) or the RBC reduced group (r2=0.004).

Example 3

The components of a preferred collagen solution of the invention was tested to identify components.

Methods

Figure 11:
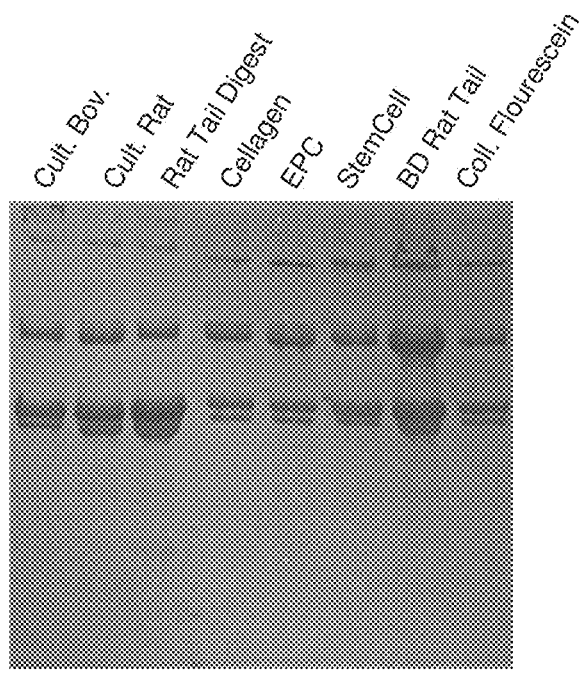
FIG. 11 is a scan of an SDS-PAGE gel depicting the components of a collagen solution of the invention.

Collagen from various sources (Cellagen, MP Biomedicals, Solon, Ohio (shown as lane 4 in FIG. 11); Elastin Products Company, Inc., Owensville, Mo. (shown as lane 5 in FIG. 11); StemCell Technologies (shown as lane 6 in FIG. 11), Becton Dickinson, Franklin Lakes, N.J. (shown as lane 7 in FIG. 11); fluorescein-labeled collagen (shown as lane 8 in FIG. 11)) were prepared into aliquot samples. Total protein content of each collagen sample was determined using a colorimetric assay (BCA Protein Assay Kit, Rockford, Ill.) in order to aliquot samples containing equal protein content. The aliquots were treated with SDS and (3-mercaptoethanol and placed at 100° C. for five minutes for denaturation and then loaded onto a 4-12% SDS-PAGE gel. The gels were stained with Coomassie Blue (Bio-Rad, Hercules, Calif.) and washed with a 7.5% acetic acid and 5% methanol destaining solution.

Results

The results of the staining of the SDS-PAGE gel are shown in FIG. 11. The results demonstrated that the commercially available products contained relatively pure Type I collagen (Lanes 4-8). Lanes 1-2 serve as negative controls. The material shown in Lane 3 of the gel in FIG. 11 was prepared according to the methods described herein, i.e. Example 1, "manufacture of acid soluble collagen used in the hydrogels". The collagen preparation of the invention produced additional bands migrating at about 39KD, signifying additional proteins present in this preparation. Two additional bands were seen at approximately 39KD, consistent with decorin and biglycan, as well as several other bands. These bands were only observed in the collagen preparations prepared according to the methods of the invention, and not in any of the commercially available collagen products tested.

Example 4

A challenge for stimulation of ACL healing has been to create an activated delivery system that provides for the release of growth factors found during the successful wound healing process in other soft connective tissues The addition of white blood cells (WBCs) to collagen solutions was tested. Surprisingly it was discovered that detectable concentrations of WBCs in the platelet rich plasma-collagen solutions described herein had a significant effect on the immediate release of VEGF from the hydrogels.

Methods

Methods for Preparation of Platelet-rich Plasma, PRP preparation using the Smart PreP2 system, Platelet and RBC-Reduced Method, Manufacture of acid-soluble collagen used in the hydrogels, and Platelet Activation: Collagen Groups were performed as described in Example 2.

Samples of whole blood and platelet rich plasma preparations were analyzed for complete blood count with differential to determine initial and final platelet and white blood cell concentrations. The data is shown in Table 2 above.

Measurement of Growth Factor Levels:

VEGF release from each gel was measured at 12 hours. Media was aspirated from around each sample and replaced with 1 ml of fresh media (serum-free DMEM with 2% antibiotics). Media samples were stored in 1.3 ml cryovials in a −80° C. freezer until all samples were collected. Concentrations of human VEGF were determined using the commercially available Quantikine colorimetric sandwich ELISA kits (R&D Systems, Minneapolis, Minn.). Assays were performed in duplicate on media samples as described in the instructions of the manufacturer. No dilution was used for the VEGF assay.

For each growth factor, the standard curve was produced by a 2-fold serial dilution of a known concentration of growth factor provided in the kit to make final concentrations of 0, 31.2, 62.5, 125, 250, 500, 1000 and 2000 pg/ml. The color change of the final reaction was measured at a wavelength of 450 nm for the optical density and the standard curve concentrations vs absorbances was linear using a four parameter logistic fit curve. The reported minimal detection limit of TGF-β1 was 4.61 pg/ml, 9.0 pg/ml for VEGF and 1.7 pg/ml for PDGF-αβ.

Results

Figure 12:
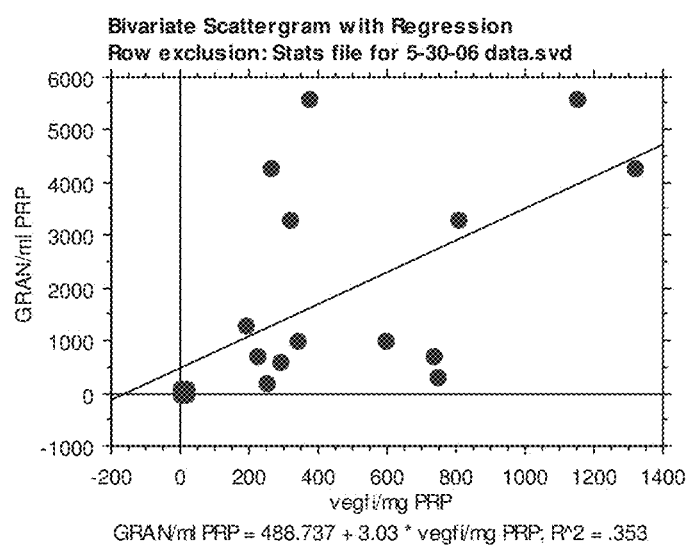
FIG. 12 is a graph depicting VEGF release as a function of granulocyte concentration in the PRP at 12 hours after platelet activation.

The results of the study are shown in FIG. 12. Linear regression analysis demonstrated a positive correlation between WBC, and in particular granulocyte, count and VEGF release at the 12 hour time point, with $r^2=0.35$. The results demonstrate that the inclusion of WBCs in the collagen-PRP materials of the invention can result in improved conditions for healing and tissue repair.

Example 5

Injection Temperature Significantly Effects In Vitro and In Vivo Performance of Collagen-PRP Hydrogels We have demonstrated the efficacy of the use of collagen-PRP hydrogels to stimulate healing of the anterior cruciate ligament (ACL) after partial and complete transection in animal models. These hydrogels are thought to serve as a substitute provisional scaffold in the ACL wound site. Important rheologic properties of the provisional scaffold include its gelation characteristics (including final modulus and time to gelation). As described above, the modulus of the provisional scaffold must be sufficient to maintain the provisional scaffold analog in the wound site and to allow it to deform in a similar fashion to the surrounding wound edges. A hydrogel with a modulus that is too low is more likely to flow out of the wound site before wound healing can be stimulated. The time to gelation is also important, as in a surgical procedure, a provisional scaffold substitute that can achieve gelation in five minutes is far more practical than a hydrogel that requires 60 or more minutes to become firm enough to allow for closure of the operative site.

In this experiment, we tested the mechanical perturbation during the accumulation of collagen crosslinks as well as the temperature at which this final perturbation occurred and demonstrated that they had a significant effect on the mechanical properties of the provisional scaffolds in vitro, and also in turn significantly effected the function of these materials in an in vivo model of ACL repair.

Materials and Methods

In Vitro Study: Experimental Design

Acid soluble collagen was neutralized and combined with platelet rich plasma to form aliquots of provisional scaffold matrix. Each aliquot was then mixed under specific heating and mixing parameters using an automated device which could accurately control the heating voltage, mixing speed and mixing time while simultaneously recording temperature within the gel. After processing, aliquots were injected onto the plate of a small oscillation rheometer and modulus and time to gelation recorded.

Preparation of Platelet-Rich Plasma (PRP)

A total of one thousand two milliliters of whole blood was drawn from two hematologically normal pigs undergoing other Institutional Animal Care and Use Committee approved studies. Blood was collected in a bag containing 10% by volume acid-citrate dextrose. The blood was transferred into fifteen milliliter centrifuge tubes, ten milliliters per tube. The tubes were centrifuged for six minutes at 150 g's (GH 3.8 rotor, Beckman GS-6 Centrifuge, Fullerton Calif.). The supernatant was collected as PRP, and complete blood counts (CBC's) were taken.

Manufacturing of Acid-Soluble Collagen Used in Hydrogels

The collagen used in this study was derived from rat tails which were obtained from control breeder rats undergoing euthanasia for other Institutional Animal Care and Use Committee approved studies. The rat-tail tendons were sterilely harvested, minced, and solubilized. The collagen content in the resulting slurry was found to be >5 mg/ml. The same collagen slurry was used in all experiments.

The collagen slurry was neutralized using HEPES Buffer (Cellgro, Mediatech, Inc, Herndon, Va.), Ham's F-10 medium (MP Biomedicals, LCC, Aurora, Ohio), Antibiotic-Antimycotic solution (Cellgro, Mediatech, Inc., Herndon, Va.) and sterile water. 7.5% sodium bicarbonate (Cambrex BioScience Walkersville, Inc., Walkersville, Md.) was used to neutralize the acidic slurry to a pH of 7.4. Aliquots of provisional scaffold analogs were created by combining equal amounts of PRP and the neutralized collagen and kept on ice until mixing as outlined below.

Apparatus for Mixing and Heating the Gels

Mixing speed, mixing time, and heating rate were controlled using a cradle designed and built by TNCO Inc. (Whitman, Mass.). An auger was designed to fit inside the 6 cc syringe held in the cradle. This allowed for mixing of the collagen hydrogel components. This device had a motor which was coupled to the auger to allow for control of mixing speed and time, and a heating pad under the syringe that allowed for control of heating rate. The cradle was connected to a notebook computer running a custom LabView (Austin, Tex.) application which allowed for control of the variables, and logging of feedback data.

The experiments performed tested three different mixing speeds (50 RPM, 100 RPM, and 150 RPM), three different mixing times (30 seconds, 60 seconds, and 120 seconds), and three different heating rates (9 mV, 11 mV, and 13 mV). All combinations of those parameters were tested as seen in Table 3. The final temperature of the gels were recorded for these mixing conditions. Additional triplicate gels having an injection temperature of 24° C.-26° C., 26° C.-28° C., 28° C.-30° C., and 30° C.-32° C. were also tested. The additional gels were prepared by mixing at 100 RPM and heating at 11 mV for the time necessary for the gel to reach the required final temperature.

TABLE 3

Gel Preparation Parameters

| Mixing Speed RPMs | Mixing Time (sec) | Heating Rate (mV) |
|---|---|---|
| 50 | 60 | 11 |
| 100 | 60 | 11 |
| 200 | 60 | 11 |
| 50 | 30 | 11 |
| 50 | 120 | 11 |
| 50 | 60 | 9 |
| 50 | 60 | 13 |

Preparation of Gels

One milliliter aliquots of the acid soluble collagen were measured into 5 ml cryotubes. An appropriate quantity of buffer was added to the tube and vortexed for five seconds. The auger was then placed into the syringe, and used to aspirate the neutralized collagen. An equal amount of PRP as acid soluble collagen was then aspirated into the same syringe. The syringe was affixed in the cradle and mixed accordingly.

Mechanical Testing

Mechanical properties of the gels were determined using Cone on Plate Small Amplitude Oscillatory Shear Rheometry using a TA Instruments AR 1000 Rheometer (New Castle, Del.). The rheometer was fitted with a 60 mm 1° acrylic cone, and the base plate was heated to 25° C. A gel was prepared as described above, and one milliliter of the collagen-PRP gel was dispensed onto the rheometer plate. The cone was lowered so that the gel was situated in a 38 µm layer between the cone and plate, and subjected to a 1% oscillatory strain. The viscoelastic complex modulus of the gel was recorded as the gelation progressed. Elastic modulus (G'), inelastic modulus (G"), and phase angle were measured for all of the gels.

In Vivo Studies: Experimental Design

Five 30 kg female Yorkshire pigs were used in the study. Four animals had bilateral ACL transactions and for each of these, one side was treated with a suture repair augmented with a collagen-PRP hydrogel, while on the contralateral side, the transection was treated with suture repair without hydrogel. In the remaining animal, unilateral surgery was performed with the augmented repair and the contralateral side left as a contemporary intact control. One of the animals developed a post-operative seroma which was treated with antibiotics on the collagen-PRP side. This knee was excluded from the study. Therefore, there were a total of four knees in the augmented repair group and four knees in the non-augmented group. All animals were survived to 14 weeks and then underwent MRI evaluation and euthanasia. Knees were immediately harvested and frozen until biomechanical testing. Load to yield, load to failure, maximum stiffness and displacement to failure were measured.

Surgical Procedure

Institutional Animal Care and Use Committee approvals were obtained for this study prior to any surgical procedures. Five 30 kg female Yorkshire pigs were used in this study. The pigs were pre-medicated with telazol 4.4-6.6 mg/kg IM, xylazine 1.1-2.2 mg/kg IM, and atropine 0.04 mg/kg. They were intubated and placed on isoflurane 1-3% for anesthesia maintenance. After anesthesia had been obtained, the pigs were weighed and placed in the supine position on the operating room table. Both hind limbs were shaved, prepared with chlorhexidine followed by betadyne paint and sterilely draped. No tourniquet was used. To expose the ACL, a four-centimeter incision was made over the medial border of the patellar tendon. The incision was carried down sharply through the synovium using electrocautery. The fat pad was released from its proximal attachment and partially resected to expose the intermeniscal ligament. The intermeniscal ligament was released to expose the tibial insertion of the ACL. A Lachman maneuver was performed prior to releasing the ACL to verify knee stability. Two #1 Vicryl sutures were secured in the distal ACL stump using a modified Kessler stitch. The ACL was transected completely at the junction of the middle and proximal thirds using a No 12 blade. Complete transection was verified visually and with a repeat Lachman maneuver that became positive in all knees with no significant endpoint detected after complete transection. All knees were irrigated with sterile saline to remove synovial fluid before suture anchor placement. An absorbable suture anchor (TwinFix AB 5.0 Suture Anchor with DuraBraid Suture (USP#2); Smith and Nephew, Inc, Andover Mass.) was placed at the back of the femoral notch. The knee was irrigated with 500 cc of sterile normal saline to remove all synovial fluid. Once hemostasis had been achieved, a collagen sponge was soaked in cold collagen-PRP hydrogel and threaded onto sutures and up into the region of the proximal ACL stump in the notch. The sutures were tied using maximum manual tension with the knees in resting flexion (approximately 70°-40° short of full extension in these animals). A second batch of collagen-PRP hydrogel was mixed by sequentially drawing up equal aliquots of neutralized collagen solution and autologous PRP into the mixing and heating device and mixing for 1 minute at 50 rpm and 13 mV which resulted in injection temperatures between 28.9 and 32.4° C. This mixture was then placed over the ACL repair to fill the intercondylar notch. The knee was left in resting extension while the identical technique of suture anchor repair was performed with an identical collagen sponge, but without the addition of the collagen-PRP hydrogel. The incisions were closed in multiple layers with absorbable sutures.

The animals were not restrained post-operatively, and were allowed ad lib activity. Once the animals recovered from anesthesia, they were permitted to resume normal cage activity and nutrition ad lib. Buprenex 0.01 mg/kg IM once and a Fentanyl patch 1-4 ug/kg transdermal were provided for post-operative analgesia. All animals were weight bearing on their hind limbs by 24 hours after surgery. After fourteen weeks in vivo, the animals were again anesthetized and underwent in vivo MR imaging using the protocol detailed below.

After the magnetic resonance images had been obtained, the animals were euthanized using Fatal Plus at 1 cc/10 lbs. No animals had any surgical complications of difficulty walking normally, redness, warmth and swelling of the knee, fever or other signs of infection that would have necessitated early euthanasia.

The six intact control knees were obtained from age- gender- and weight-matched animals after euthanasia following surgical procedures to the chest. The hind limbs were frozen at −20° C. for three months and thawed overnight at 4° C. before mechanical testing. All other testing conditions for these knees were identical to those in the experimental groups.

Magnetic Resonance Imaging

In vivo magnetic resonance imaging was performed at 1.5 Tesla (GE Medical Systems, Milwaukee, Wis.) with an eight-channel phased array coil at the specified time points. Scanning was performed with the knees placed maximum extension (between 30 and 45 degrees of flexion). Conventional MR included multiplane T1, FSE PD and T2 weighted images. Field of view (FOV): 16-18 cm, matrix: 256×256, (repetition time/echo time) TR/TE: 400/16, 2500/32, 3000/66 msec, echo train length (ETL): 8, bandwidth (BW): 15 kHz, slice thickness: 3, interslice gap: 1 mm). Perfusion was evaluated by using spoiled gradient echo sequence (TR/TE=200/2 ms, flip angle=60, 3 mm slice thickness, and 0.625 mm in plane resolution) with an intravenous contrast agent (Magnevist; Berlex, Wayne, N.J.) 0.2 ml/kg injected 10 s after the start of scan. Five images were obtained per slice, 78 s apart. Post contrast T1-weighted images were obtained (FOV:16 cm, matrix: 256×256, TR/TE: 400/9 msec, slice thickness: 3 mm, interslice gap: 1 mm) in the coronal and sagittal planes.

Biomechanical Testing

The bone-ligament-bone ACL complex from both knees for each pig was tested in uniaxial tension. In brief, testing was performed with the knee flexed at 30 degrees of flexion and at room temperature. Immediately after preconditioning, each specimen was tested to failure in uniaxial tension at 20 mm/min. Close-range digital images were acquired at 3 Hz using a high resolution digital camera with a macro lens (PixeLINK PLA662 Megapixel Firewire camera, PixeLINK, Ottawa ON, Canada) to determine failure mode. The yield load, displacement at yield, tangent modulus (maximum slope of force-displacement curve), maximum load at failure, displacement at failure and total work to failure (area under force-displacement curve) were determined from the force-displacement curve measured for each bone-ligament-bone ACL complex. The yield load represented the point along the normalized force-displacement curve where the mechanical behavior of the ACL complex departed from "linear" behavior and for the purposes of this analysis was defined as the point where the tangent modulus declines by at least 2% from its maximum value. The displacement at yield was the displacement recorded at this same point. The maximum load is the maximal normalized load sustained by the ACL complex prior to failure and the displacement at failure the displacement recorded at the maximum load. The energy to failure was derived by integrating the total area under the force-displacement curve.

Statistical Analysis

Mechanical testing measurements were compared at 4 weeks in vivo between intact ACL and ACLs treated by suture anchor repair alone and to those treated by suture anchor repair plus collagen sponge using F-tests from multivariate analysis of variance (MANOVA) with 95% confidence intervals (CI). A F-test exceeding the critical value of 3.84 would be regarded as evidence for statistical significance. Each of the six variables (load at yield, maximum load, displacement at yield, displacement at failure, tangent modulus, and energy to failure) followed a normal (Gaussian-shaped) distribution and therefore data are presented in terms of the mean and standard deviation (SD). Paired t-tests were used to evaluate differences in ACLs treated with suture anchor repair alone compared to the bilateral side receiving suture anchors with PRP. Statistical analysis was performed using SPSS version 14.0 (SPSS Inc., Chicago, Ill.). All values of $p<0.05$ were considered statistically significant.

Results

Hematology

A one milliliter sample of whole blood from each pig, and a one milliliter sample of each of the PRPs were taken to the CBR Institute for Biomedical Research (Boston, Mass.) and a complete blood count was performed. The results are summarized in Table 4.

TABLE 4

Summary of Blood Results

| | Whole Blood | Platelet Rich Plasma |
|---|---|---|
| PRP #1 | | |
| Platelet Count (Platelets/µl) | $3.71 \times 10^5$ | $6.52 \times 10^5$ |
| Red Blood Cell Count (RBC/µl) | $4.46 \times 10^6$ | $3 \times 10^4$ |
| White Blood Cell Count (WBC/µl) | $6.6 \times 10^3$ | $2.2 \times 10^3$ |
| Hematocrit (%) | 28.4 | 0.2 |
| PRP #2 | | |
| Platelet Count (Platelets/µl) | $3.30 \times 10^5$ | $7.76 \times 10^5$ |
| Red Blood Cell Count (RBC/µl) | $5.78 \times 10^6$ | $4 \times 10^4$ |
| White Blood Cell Count (WBC/µl) | $9.6 \times 10^3$ | $2.7 \times 10^3$ |
| Hematocrit (%) | 39.3 | 0.3 |

Mechanical Testing

1.) the Effect of Mixing Time

Figure 13A:
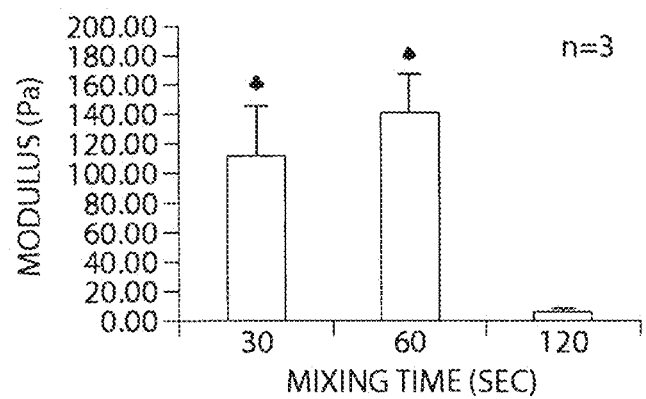
FIG. 13A: Mean elastic modulus for the collagen-PRP hydrogels as a function of mixing time. ♣ represents a statistically significant difference between 30 seconds and 120 seconds. ♠ represents a statistically significant difference between 60 seconds and 120 seconds. Error bars represent ±one standard deviation.
Figure 13B:
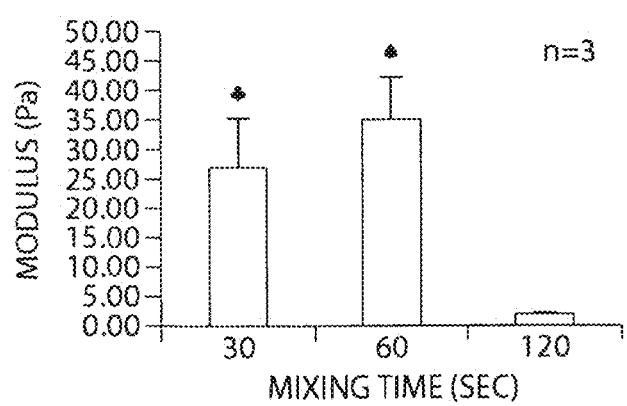
FIG. 13B: Mean inelastic modulus for the collagen-PRP hydrogels as a function of mixing time. ♣ represents a statistically significant difference between 30 seconds and 120 seconds. ♠ represents a statistically significant difference between 60 seconds and 120 seconds. Error bars represent ±one standard deviation.

There was no statistical difference between mixing the components of the gels for 30 seconds or 60 seconds as measured by the maximum elastic modulus (112±34 Pa vs 142±25 Pa). The results are shown in FIG. 13A. However, mixing for 120 seconds significantly decreased the maximum elastic modulus to only 5±2 Pa (single variable ANOVA $p<0.01$). Similar findings were noted for the inelastic modulus (shown in FIG. 13B). The inelastic modulus for the samples mixed for 30 seconds was 27±8 Pa, and the inelastic modulus for the samples mixed for 60 seconds was 35±7 Pa. This did not represent a statistically significant difference. However, the inelastic modulus was significantly lower for the 120 second mixing samples (2±0.4 Pa) when compared to the 30 second and 60 second mixing time samples (single variable ANOVA $p<0.001$).

There was no statistically significant difference in the rate of gelation as measured by time to 45°, the time to G'max, and the time to G"max for the samples mixed for 30 or 60 seconds. For the samples mixed for 30 seconds, the time to 45° was 3.1±0.0 mins, the time to G'max was 16±2.6 mins, and the time to G"max was 16±2.8 mins. For the samples mixed for 60 seconds, the time to 45° was 2.7±0.4 mins, the time G'max was 14.2±4.2 mins, and the time to G"max was 14.2±4.3 mins. However, the samples mixed for 120 seconds had a time to 45° of 0.3±0.03 mins, which represents a statistically significant decrease (single variable ANOVA $p<0.001$) when compared to both the 30 second and 60 second mixing samples. Time to G'max (9.5±5.2 mins) and G"max (8±6.8 mins) were not statistically significant when comparing the 30 second and 60 seconds samples to the 120 second samples.

2.) the Effect of Mixing Speed

Figure 14A:
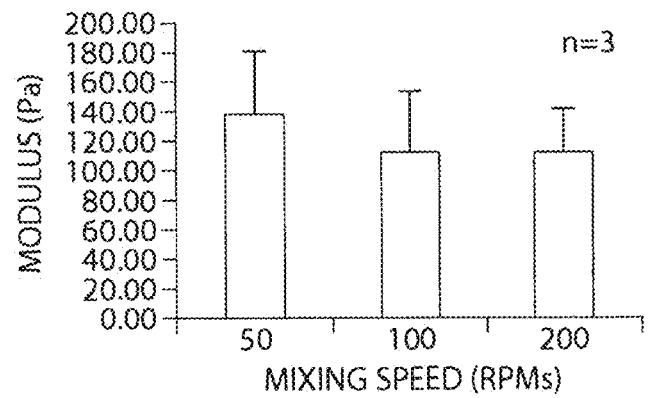
FIG. 14A: Mean elastic modulus for the collagen-PRP hydrogels as a function of mixing speed. The differences between the three groups were not statistically significant. Error bars represent ±one standard deviation.
Figure 14B:
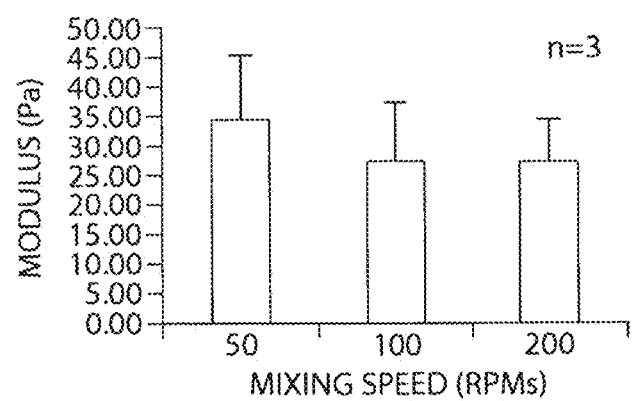
FIG. 14B: Mean inelastic modulus for the collagen-PRP hydrogels as a function of mixing speed. The differences between the three groups were not statistically significant. Error bars represent ±one standard deviation.

Examining the affect that mixing speed had on the rheological properties of the collagen-PRP hydrogels, there was no statistically significant difference between the three mixing speeds for both the elastic (FIG. 14A) and the inelastic modulus (FIG. 14B) (single variable ANOVA). Mixing at 50 RPMs resulted in an elastic modulus of 140±42 Pa, and an inelastic modulus of 35±11 Pa. Mixing at 100 RPMs resulted in an elastic modulus of 112±41 Pa, and an inelastic modulus of 27±10 Pa. Mixing at 200 RPMs resulted in an elastic modulus of 112±30 Pa, and an inelastic modulus of 27±7 Pa.

Furthermore, the various mixing speeds did not have a statistical affect on the speed at which gelation occurred as measured by time to 45°, time to G'max, and time to G"max. For the gels mixed at 50 RPMs, the time to 45° was 2.3±0.0 mins, the time to G'max 16±2.4 mins, and the time to G"max was 16±2.5 mins. For the gels mixed at 100 RPMs, the time to 45° was 2.8±0.5 mins, the time to G'max 16±1.6 mins, and the time to G"max was 16±1.7 mins. For the gels mixed at 200 RPMs, the time to 45° was 2.7±0.6 mins, the time to G'max 17±4.1 mins, and the time to G"max was 16.7±3.6 mins.

3.) the Effect of Heating Rate

Figure 15A:
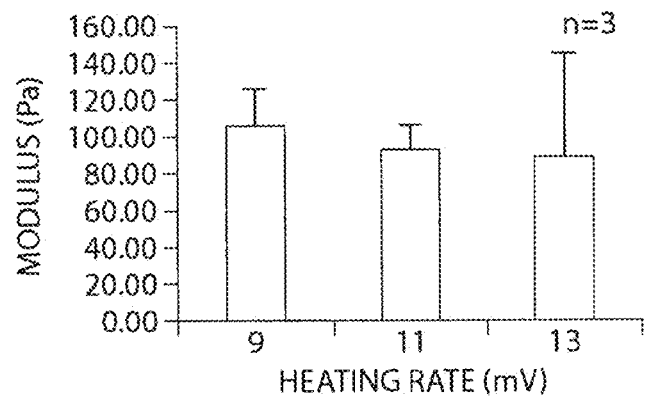
FIG. 15A: Mean elastic modulus for the collagen-PRP hydrogels as a function of heating rate. The differences between the groups were not statistically significant. Error bars represent ±one standard deviation.
Figure 15B:
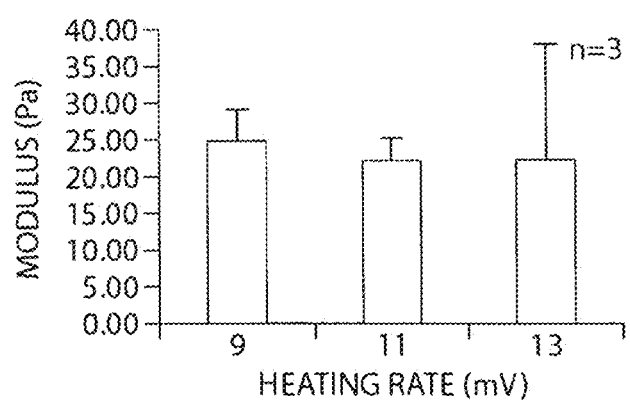
FIG. 15B: Mean inelastic modulus for the collagen-PRP hydrogels as a function of mixing speed. The differences between the groups were not statistically significant. Error bars represent ±one standard deviation.

Increasing the heating rate of the collagen-PRP hydrogels did not have a statistical effect on the viscoelastic modulus of the gels. The gels heated at 9 mV recorded an elastic modulus of 106±20 Pa (FIG. 15A), and an inelastic modulus of 25±4 Pa (FIG. 15B). The gels heated at 11 mV had an elastic modulus of 93±13 Pa, and an inelastic modulus of 22±3.1 Pa. The gels heated at 13 mV had an elastic modulus of 89±56 Pa, and an inelastic modulus of 22±16 Pa. None of these represent statistically significant differences.

For the gels heated at 9 mV, the time to 45° was 3.6±0.4 mins, the time to G'max 17.4±1.0 mins, and the time to G"max was 16.4±2.0 mins. The gels heated at 11 mV had a time to 45° of 2.4±0.6 mins, a time to G'max of 16±0.5 mins, and a time to G"max of 15±0.8 mins. Finally, the gels heated at 13 mV had a the time to 45° of 2.0±0.5 mins, a time to G'max of 17±1.2 mins, and a time to G"max of 16±1.5 mins. Comparing these values, the only statistically significant comparison was between the 9 mV and the 13 mV heating rates for time to 45° (single variable ANOVA p<0.01).

4.) the Effect of Injection Temperature

Figure 16A:
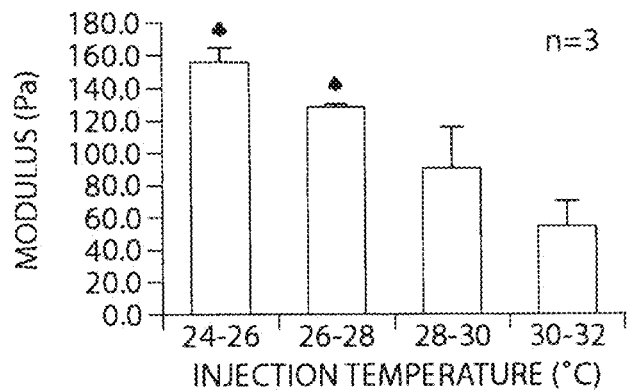
FIG. 16A: Mean elastic modulus for the collagen-PRP hydrogels as a function of injection temperature. ♣ represents a statistically significant difference between 24° C.-26° C. and all other groups. ♠ represents a statistically significant difference between 26° C.-28° C. and all other groups. Error bars represent ±one standard deviation.
Figure 16B:
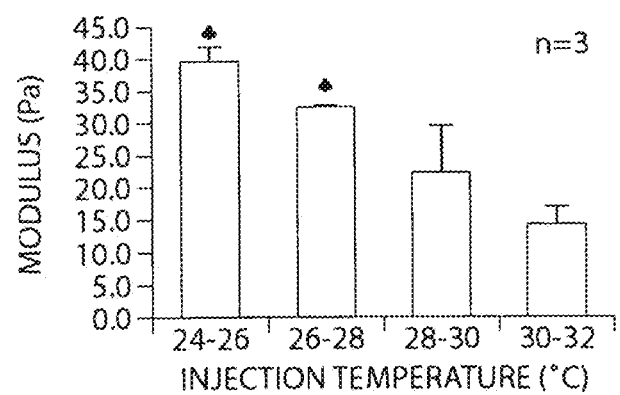
FIG. 16B: Mean inelastic modulus for the collagen-PRP hydrogels as a function of injection temperature. ♣ represents a statistically significant difference between 24° C.-26° C. and all other groups. ♠ represents a statistically significant difference between 26° C.-28° C. and all other groups. Error bars represent ±one standard deviation.

An increase in injection temperature resulted in a decrease in the mechanical properties of the Collagen-PRP hydrogels. The gels injected onto the rheometer plate between 24° C. and 26° C. had an elastic modulus of 156±26 Pa (FIG. 16A), and an inelastic modulus of 39.4±7.2 Pa (FIG. 16B). The gels injected onto the rheometer plate between 26° C. and 28° C. had an elastic modulus of 128.7±15.7 Pa, and an inelastic modulus of 32.3±2.7 Pa. The gels injected onto the rheometer plate between 28° C. and 30° C. had an elastic modulus of 90.3±11.4 Pa, and an inelastic modulus of 22.3±3.6 Pa. Finally, the gels injected onto the rheometer plate between 30° C. and 32° C. had an elastic modulus of 54.6±30.4 Pa, and an inelastic modulus of 14.2±6.5 Pa. For the elastic modulus, there was a statistically significant difference between the gels injected between 24° C. and 26° C., and all other groups (single variable ANOVA p<0.01), and a statistically significant difference between the gels injected between 26° C. and 28° C., and the gels injected between 30° C. and 32° C. For the inelastic modulus, there was a statistically significant difference between the gels injected at 24° C.-26° C., and the gels injected at 28° C.-30° C., and the gels injected at 30° C.-32° C. (single variable ANOVA p<0.005). There was also a statistically significant difference in inelastic modulus between the gels injected at 26° C.-28° C. and the gels injected at 30° C.-32° C. (single variable ANOVA p<0.005).

Figure 17:
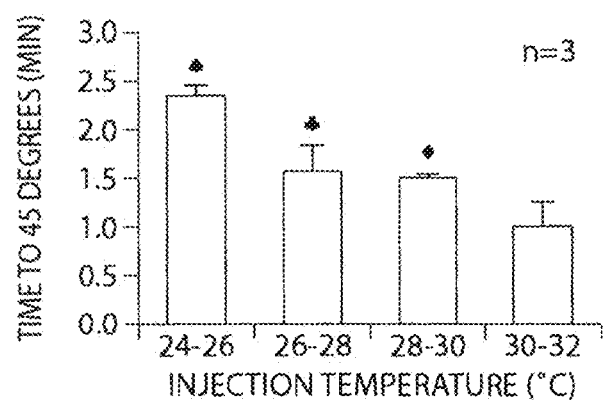
FIG. 17: Mean time to 45° for the collagen-PRP hydrogels as a function of injection temperature. ♣ represents a statistically significant difference between 24° C.-26° C. and all other groups. ♠ represents a statistically significant difference between 26° C.-28° C. and all other groups. ♦ represents a statistically significant difference between 28° C.-30° C. and all other groups. Error bars represent ±one standard deviation.

The rate of gelation, as measured by time to 45°, the time to G'max, and the time to G"max was affected by increasing temperature of injection. For the gels injected between 24° C. and 26° C., the time to 45° was found to be 2.3±0.1 mins, the time to G'max was 14.6±4.5 mins, and the time to G"max was 14.5±4.7 mins. For the gels injected between 26° C. and 28° C., the time to 45° was 1.6±0.3 mins, the time to G'max was 10.5±3.1 mins, and the time to G"max was 9.4±2.1 mins. For the gels injected between 28° C. and 30° C., the time to 45° was found to be 1.5±0.0 mins, the time to G'max was 10.6±3.3 mins, and the time to G"max was 9.0±2.1 mins. Finally, for the gels injected between 30° C. and 32° C., the time to 45° was found to be 1.0±0.2 mins, the time to G'max was 8.6±0.8 mins, and the time to G"max was 8.5±0.9 mins. Statistically, there were no significant differences between the groups for time to G'max and time to G"max; however, there were statistically significant differences between the groups for time to 45°. There was a significant decrease in time to 45° when comparing the gels injected between 24° C. and 26° C. to all the other injection temperature groups (single variable ANOVA p<0.003) (FIG. 17). There was also a significant difference for the time to 45° between the 26° C.-28° C. group and the 30° C.-32° C. group, and between the 28° C.-30° C. group and the 30° C.-32° C. group (single variable ANOVA p>0.005).

Figure 18:
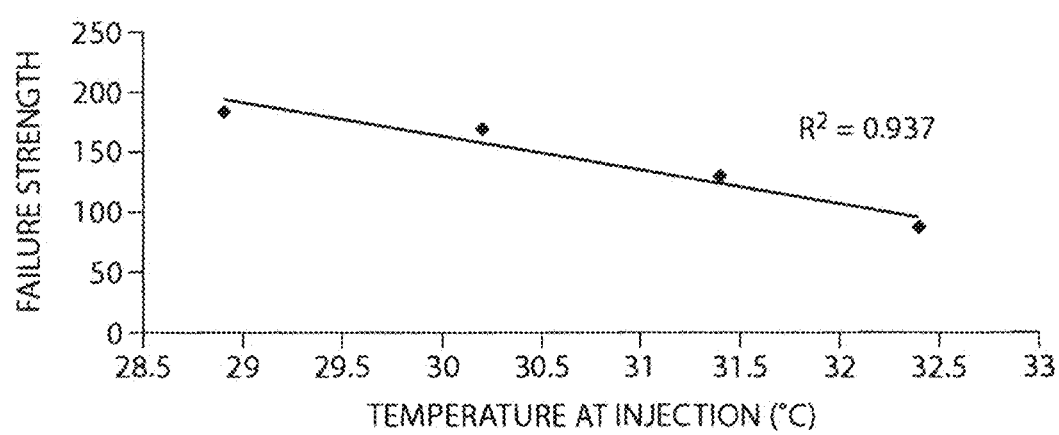
FIG. 18 is a graph depicting in vivo results of failure strength versus temperature at injection.

In vivo results: Effect of injection temperature on repair strength at 14 weeks is shown in FIG. 18. Average strength in the sponge alone control group was 206N. The temperature of the gel at injection significantly affects both the in vitro mechanical properties of the hydrogel, as well as the in vivo properties of tissue healing induced by the hydrogel. Temperatures of less than 26° C. yielded the strongest gels in vitro and temperatures of 28° C. yielded the strongest in vivo healing ligaments.

Example 6

Platelets Enhance ACL Graft Strength and Post Operative Knee Laxity in a Caprine Model ACL injuries affect over 200,000 patients each year in the US. While ACL reconstruction is a reliable procedure for grossly restoring stability of the knee, normal biomechanics of the knee are not restored and a clinically relevant percentage of patients have excessive laxity post-operatively. The early healing of the ACL reconstruction graft with decreased structural properties could explain in part previous work in humans showing the majority of the increase in knee laxity post-operatively occurs in the first several months after surgery. Thus, strategies which could improve the early structural properties (strength and stiffness) of the ACL graft are desirable as a potential solution to reduce the risk of abnormal knee laxity after ACL reconstructive surgery.

We have demonstrated by histological evaluation of healing of a biomechanically stable partial ACL injury model the growth factor profile. In normal extraarticular healing of medial collateral ligament (MCL) and patellar tendon (PT) the expression of and timing was qualitatively similar to placement of a collagen-platelet hydrogel in the partial ACL. This is in contrast to the lack of healing and severely limited growth factor expression in the partial ACL injury without (control) collagen-platelet hydrogel. Specific individual growth factors (PDGF vs TGF and EGF vs VEGF) have been applied to ACL reconstruction models in either sheep or canines. Both growth factors that are abundant in platelets (PDGF and TGF) demonstrated improved load and stiffness at 12 weeks postoperatively. However the application of a growth factor to stimulate revascularization (VEGF) weakened the graft at 12 weeks. The earlier time points (6 weeks), optimal dosage, combination or application method to improve early structural properties when the ACL reconstruction graft is near the weakest is unknown. Thus, the strategy to apply the body's own growth factors to promote the return of structural properties of the ACL reconstruction graft requires further research.

This study was performed to show that placement of a platelet gel around an ACL graft at the time of surgery would improve the early mechanical properties of the graft (maximum load and stiffness). It was also shown that the platelet concentration around the graft would have a direct correlation with the early load to failure of the ACL graft.

Materials and Methods:

Animal Model

Twelve 4-year old castrated male Nubian cross goats underwent unilateral anterior cruciate reconstruction using a bone-patellar tendon-bone autograft. In the experimental group six goats had the graft augmented with a collagen-platelet hydrogel, while the six control goats had augmentation with the collagen-hydrogel only. The surgeries were alternatively performed between the right and left knees within each treatment group. The animals were allowed unrestricted cage activity while ACL reconstruction grafts were healing. At six weeks postoperatively they were euthanized with an overdose of pentabarbitol solution (Euthasol; 1 cc/10 lbs). At the time of euthanasia, both the reconstructed and contralateral control knees were harvested and stored at −20° C. prior to mechanical testing.

Surgical Procedure

The animals were tranquilized preoperatively using acepromizine (10 mg IM). Anesthesia was then induced with sodium pentothal (5-8 mg/Kg IV) and maintained during surgery using isofluorane.

A 15 blade was used to make an incision from top of patella to below the tibial tubercle just medial of midline. The prepatellar bursa was cut in line with the skin incision to expose the paratenon. A longitudinal cut was made centrally in the paratenon to expose the patellar tendon. The medial and lateral borders of the patellar tendon were palpated and a 6 mm wide graft marked with the electrocautery. The patellar block was 15×6 mm, leaving 10 mm of patella intact superiorly. The tibial bone block was 10×6 mm. The harvested graft was shaped to fit 6 mm diameter bone blocks and 1.5 mm drill holes were placed in the bone block on each side. Because the length of the patellar tendon is greater than the ACL, the tibial bone block was folded over onto the patellar tendon and sutured in place to make an 8 mm bone-tendon block on this side to shorten it. Two #2 Ethibond sutures were placed in each bone block. The intracondylar notch was exposed through the central defect in the patellar tendon by sectioning the fat pad. The intermeniscal ligament was not cut. A Lachman test was checked for baseline stability of the knee. A #11 blade was used to release the ACL from the back of the notch, and the ACL was removed by releasing the ligament from its tibial insertion. A manual Lachman was performed to verify complete functional loss of the ACL. The tibial tunnel was drilled using the tibial aiming guide set at 65°. The pin was over-drilled with an 8 mm drill and all soft tissue removed. A notchplasty was performed using a curette. The knee was hyperflexed and a 6 mm offset femoral drill guide (Arthrex Inc, Naples Fla.) was placed into the back of the notch at the 10:30 position. The passing pin was drilled through the femur and then over-drilled with a 7 mm drill to 20 to 25 mm. Integrity of the back wall of the femoral tunnel was verified in all cases. The graft was placed into the femoral tunnel first using the Ethibond sutures, and then secured in the femur using a 5×20 mm interference screw (Arthex, Inc.). The graft was then pulled retrograde into the tibial tunnel. With the knee at 60 degrees of flexion, the graft was firmly tensioned and secured in the tibial tunnel using a 6×20 mm interference screw (Arthex, Inc.). Tibial fixation was augmented with sutures to the periosteum if the tibial fixation was not deemed stable enough.

For the experimental group the graft was augmented with a collagen sponge placed between the ACL and LFC using a freer elevator, with part of the sponge lying anteriorly to the graft. Two cubic centimeters of a collagen-platelet hydrogel (n=6) was placed over the sponge. The control group was identical except no platelets were added to the collagen-hydrogel. After ten minutes, the knee was closed in layers. The animals were kept under anesthesia for 1 hour after gel placement to maintain the knees in the resting position and allow complete gelation.

Post-operative analgesia was control using Buprenorphine (0.01 mg/Kg IM, twice daily) and Ketoprofen (1 mg/Kg IM, once daily) for five days. Ampicillin (10 mg/Kg SC, twice daily) was administered for 10 days to reduce the risk of infection.

Collagen Gel and Collagen-Platelet Gel Manufacture

Rat tail collagen was acid-solubilized as described herein. For the collagen group, the collagen was neutralized to a pH of 7.4 and added to the surgical site just after neutralization. To add platelets to the gel, initially the production of platelet-rich plasma was attempted; however, due to the similarity in size and weight of the caprine platelet and red blood cell, centrifugation protocols using 150 to 250 g between 20 and 30 minutes all resulted in effective decrease of red blood cells in the PRP, but platelet counts in the PRP fraction were less than 100% that of the whole blood with all protocols. Using the most effective protocol determined ex vivo, 250 g for 30 minutes, the platelet yield in the caprine PRP averaged 102%+/−68% (mean+/−standard deviation) for the 12 goats in this study when the measured MPV was used to calculate platelet number. In addition, there were large variations in enrichment seen within the group. Therefore, we elected to use whole caprine autologous blood for the collagen-platelet group. This resulted in the peripheral blood platelet concentration determining the concentration of platelets delivered in the collagen-platelet hydrogel. In addition, we measured the platelet concentration in the peripheral blood for all animals, both experimental and control groups. Fifty-four cc of blood was drawn from each animal into a syringe containing 6 cc of acid-citrate-dextrose as an anticoagulant. At the time of gel placement, the collagen was neutralized and mixed with the blood in a 4:1 collagen:blood ratio and the collagen-platelet gel added to the graft.

Mechanical Testing

After all specimens were collected, the knees were thawed and prepared for laxity and failure testing. The soft tissues surrounding the tibia and femur were dissected free leaving the joint capsule intact. The distal tibia and proximal femur were then potted in PVC pipes using a potting material (SmoothCast 200; Smooth-On, Easton Pa.) so that they could be mounted for mechanical testing.

Figure 19:
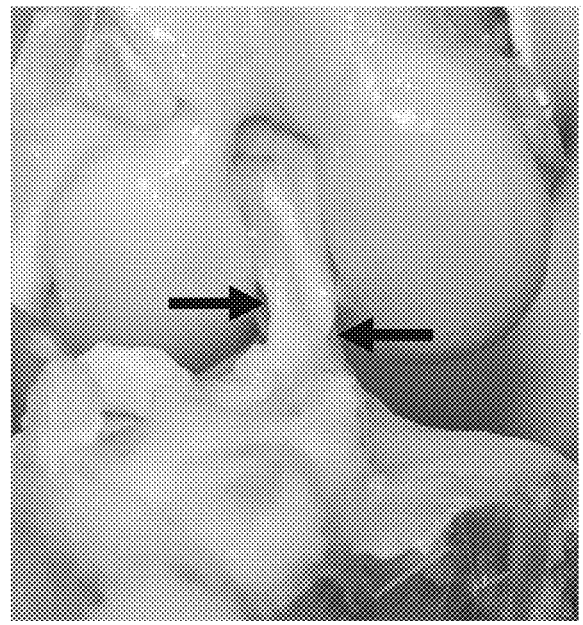
FIG. 19: Coronal (A) view of a caprine knee with an intact ACL. The black arrows designate the ACL itself.

The anteroposterior load-displacement responses of the intact joints were measured using a custom designed fixture with the knee locked at 30° and 60° of flexion (FIG. 19) (Fleming et al JOR 19: 841, 2001). Anterior and posterior directed shear loads of ±60 Newtons were applied to the femur with respect to the tibia using a MTS 810 Materials Testing System (MTS, Prairie Eden, Minn.) while the AP displacement was measured. Axial rotation of the tibia was locked in the neutral position, and all other motions were left unconstrained.

After completing the AP laxity tests, the tibia and femur were positioned on the so that the mechanical axis of the ACL was collinear with the load axis of the material test system (Woo et al; AJSM 19: 217, 1991; Tohyama et al; AJSM 24: 608, 1996). The knee flexion angle was set at 30°. The tibia was mounted to the base of the MTS via a sliding X-Y platform. The femur was unconstrained to rotation. This enabled the specimen to seek its own position so that the load was distributed over the cross section of the healing graft when the tensile load was applied.

The joint capsule, menisci, collateral ligaments and the PCL were dissected from the joint leaving the ACL graft and scar mass intact. The femur-graft-tibia complexes were then loaded in tension to failure at 20 mm/min while the failure load-displacement data were recorded. Identical protocols were performed on the contralateral ACL-intact knees. From the MTS load-displacement tracing, the failure load, failure displacement, and the linear stiffness were determined.

Exclusion

The first animal operated on was assigned to the collagen-platelet group. There were technical difficulties with the graft harvest in this animal and at the conclusion of surgery, it was decided to exclude this animal from the analysis. In addition, one of the animals in the collagen alone group had a graft with a failure strength more than three times higher than any other animal in either group, thus was excluded from the remaining analysis due to the 3 sigma rule. Therefore, neither animal is represented in any group statistic nor are they graphically depicted in any figure.

Statistical Analyses

Comparisons of AP laxity values, failure strength, and stiffness values between the collagen (carrier only) and platelet collagen groups were made. The differences for each of these parameters between the treated knee and the contralateral control knee were calculated. Unpaired t-tests were performed to determine if the differences were significant ($p<0.05$). Correlation analyses were performed to determine the association between systemic platelet count and the strength of the graft after 6 weeks of healing.

Results

Surgical Outcome

Eleven out of the 12 animals recovered well from surgery. However, one goat from the collagen only group died within one day of surgery. Autopsy revealed extensive atherosclerosis and the cause of death was thought to be cardiac-related. At the time of euthanasia, all animals appeared to be walking normally.

Gross Appearance

Observers were blinded to group when harvesting and grading the specimens. There was no difference between the collagen and collagen-platelet groups on gross appearance in terms of rate of reformation of the ligamentum mucosum, rate of scar or adhesion formation from the notch scar mass to the harvest defect of the patellar tendon or amount of joint adhesions observed. There was no difference between the groups in whether the scar mass infiltrated only the most cranial section of the graft or whether it bridged from femur to tibia—both findings were seen in ligaments of both groups.

Biomechanics

At a knee flexion angle of 60 degrees of flexion, the AP laxity of the knees was 34% lower in the collagen-platelet group than in the collagen group, a difference which was statistically significant (17.2+/−3.3 mm vs 23.1+/−4.0 mm; mean+/−SD; $p<0.05$). At 30 degrees of flexion, there was also a 40% decrease in AP laxity of the knees in the collagen-platelet group; however, the difference approached, but did not reach, statistical significance, due in part due to the large standard deviations seen within each group (collagen-platelet group 14.3+/−4.0 mm vs collagen group 20+/−4.5 mm; $p<0.09$).

The collagen-platelet group strength was 30% higher than the collagen group (139+/−41N vs 108+/−47N; both mean+/−SD), a difference that was not statistically significant ($p>0.30$). The values in both groups were approximately 10% of the intact ACL strength. Femoral tunnel size, collagen sponge size and collagen gel amount were not found to be significant predictors of failure strength.

There was no significant difference between the groups in terms of failure displacement. The collagen group failed at 9.3+/−5.1 mm (mean+/−SD) and the collagen-platelet group failed at 8.4+/−4.4 mm ($p>0.80$). Interestingly, both values were far lower than the failure displacement in the contralateral intact ligaments, which averaged 20.8+/−1.8 mm. There was also no significant difference in linear stiffness between groups, with the collagen group having a stiffness of 22+/−15 N/mm and the collagen-platelet group having a stiffness of 26+/−14 N/mm (mean+/−SD; $p>0.60$). Both groups were less than one third of the intact ligament average stiffness (90+/−34 N/mm; mean+/−SD).

Figure 20:
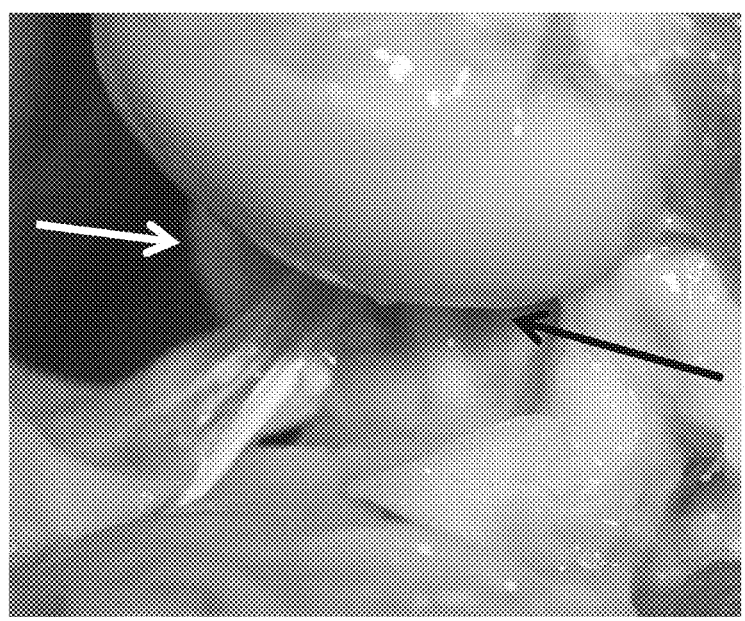
FIG. 20: Graft healing in the collagen group (sagittal view). The graft appears similar to the appearance at implantation (white arrow); however, there is scar mass present behind the graft (black arrow).
Figure 21A:
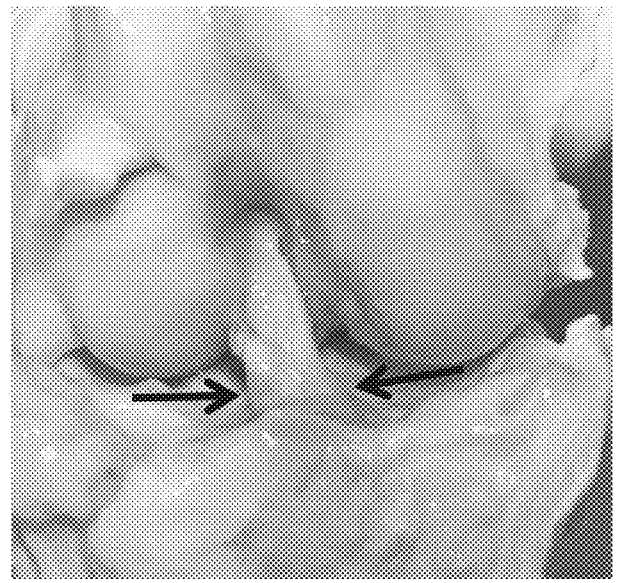
FIG. 21A and FIG. 21B: Graft healing in the collagen-platelet group. The graft is larger than at implantation and appears grossly to be synovialized and infiltrated with fibrovascular tissue. Good integration was observed at the insertion sites. (21A=coronal view, 21B=sagittal view).
Figure 21B:
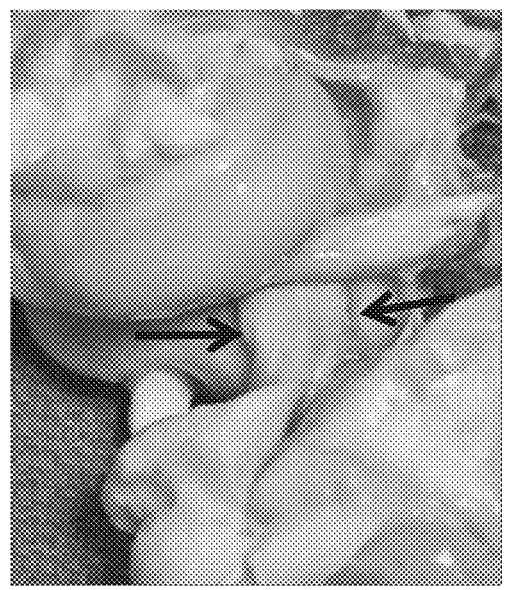
Figure 22:
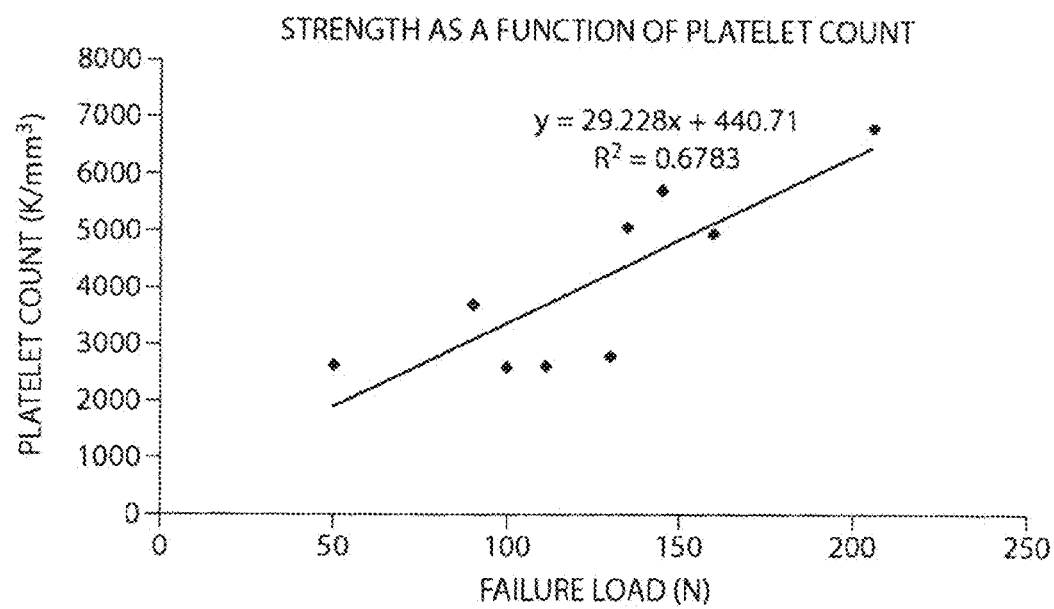
FIG. 22 is a graph depicting strength of the joint as a function of platelet count.
Figure 23A:
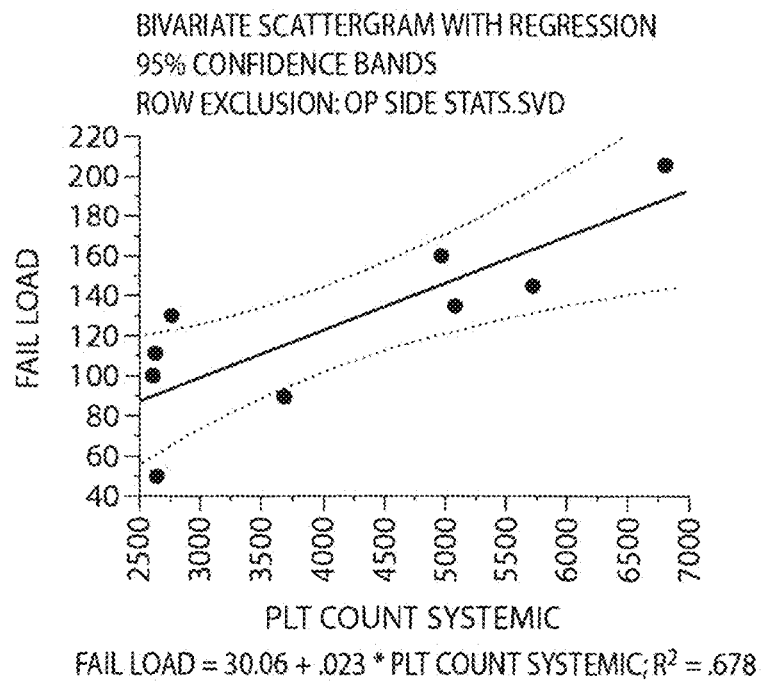
FIGS. 23A and 23B are bivariate scattergrams wit regression 95% confidence bands.
Figure 23B:
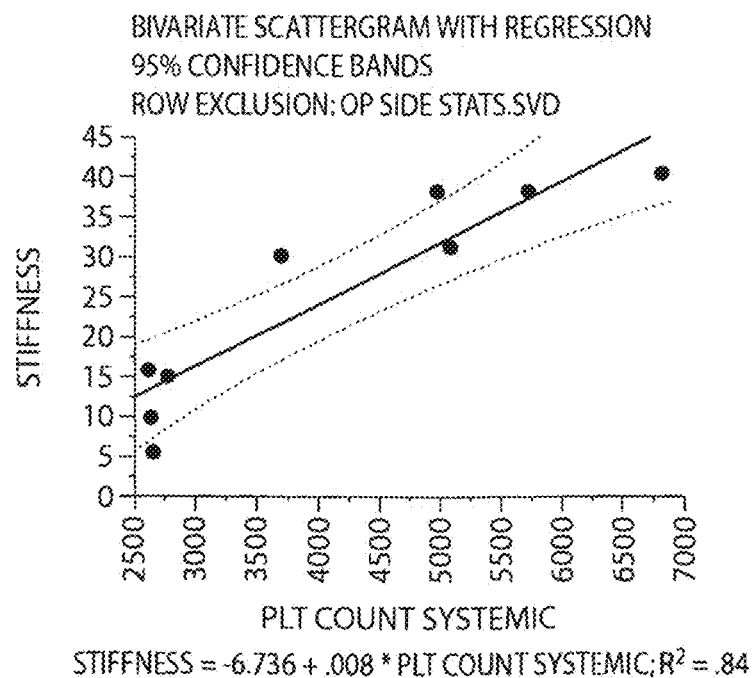

Higher systemic platelet counts correlated significantly with both higher failure load (FIG. 20: $R^2>0.67$) and higher ligament linear stiffness (FIG. 21A and FIG. 21B: $R^2>0.80$) using a linear regression model. There was no significant correlation between platelet concentration and failure displacement ($R^2=0.40$) or AP laxity at 60 degrees ($R^2=0.44$) with the number of animals tested. The data is depicted graphically in FIG. 22 and FIG. 23A and FIG. 23B. FIG. 22 is a graph depicting strength of the joint as a function of platelet count. FIGS. 23A and 23B are bivariate scattergrams wit regression 95% confidence bands. FIG. 23A depicts fail load as a function of platelet count. FIG. 23B depicts stiffness as a function of platelet count.

Thus, AP laxity measured at 30 degrees of knee flexion was significantly improved in the experimental platelet group when compared to that treated with the carrier alone (154%+/−44% vs 355%+/−55%; $p=0.03$). There was no significant difference between the maximum load of the ACL graft in the two groups; however, the maximum load of the graft correlated directly with the systemic platelet count in both the experimental (R2=0.95) and control (R2=0.85) groups. The addition of platelet to the collagen-hydrogel improved AP laxity when compared to previous reports of ACL reconstructed knees at six weeks.

The addition of blood platelets to the collagen hydrogel (experimental group) resulted in clinically significant reduction in knee laxity at six weeks after autograft patellar tendon ACL reconstruction. In addition, the systemic platelet count of the animals correlated directly with the maximum load for both the experimental group (collagen-platelet hydrogel) and the control group (collagen hydrogel). Both of these findings highlight the role blood platelets play in ACL reconstruction graft healing with presumably clinically relevant reduction in early undesired postoperative AP laxity.

The improvement in AP laxity was evident when the knees were tested in 30 degrees of flexion (full extension in the caprine knee). At this position, the knees treated with collagen-platelet hydrogel had only 54% more AP laxity than the contralateral knees with intact ACLs, while the knees treated with collagen hydrogel alone were over 200% more lax than the intact knees. At 60 degrees of flexion, the difference between groups was smaller and insignificant. This finding suggests a potential role for reducing early undesired clinical laxity. Whether the platelets' effect was on the graft healing or capsular structures is unknown. Further optimization of platelet concentration as well as timing of administration is needed. The large increases in AP laxity seen in the collagen hydrogel alone group are consistent with those of previous studies of ACL reconstruction with autogenous patellar tendon grafts using the goat model (Abramowitch JOR 21:707, 2003; Cummings JOR 20:1003, 2002; Papageorgiou AJSM 29:620, 2001; Jackson AJSM 21:176, 1993). Papageorgiou et al reported 238% and 285% increases in AP laxity with the knee at 30 degrees and 60 degrees of flexion, respectively, after 6 weeks of healing. The improvement seen in the collagen-platelet group is also a marked improvement from results published previously on ACLR in sheep where the AP laxity of the knee increased from 2.0+/−0.7 mm in the intact knee, to 8.3+/−2.3 mm at six weeks in a model using femoral and tibial interference screw fixation as we did in this study (HUNT et al *Knee Surg Sports Traumatol Arthrosc*. 2006 December; 14(12):1245-51.).

The six week time point is well recognized as a nadir of strength in ACL reconstruction for animal models. The strength values in both groups were approximately 10% of the intact ACL, which is slightly higher than previous reports of 3% in the sheep model (Hunt et al *Knee Surg Sports Traumatol Arthrosc*. 2006 December; 14(12):1245-51.), and typical for the goat model after 6-weeks of healing (Papgeorgiou AJSM 29:620, 2001; Abramowitch 21:708, 2003). By applying platelets in a stabilized collagen-hydrogel we have simulated the "natural" environment found with platelets being deposited in a fibrin clot for extraarticular healing. Further, platelets contain a multitude of growth factors in addition to TGF-β and PDGF in the appropriate concentration for extraarticular healing. Additionally, the cost of recombinant TGF or PDGF or EGF far exceeds the cost to apply autograft platelets from blood.

Limitations of the study include the inability to control rehabilitation in the animals and the inability in the caprine model to provide two- to four-fold increased platelet concentrates in the collagen hydrogel. Ruminants must be upright standing in the very early post-operative period, thus it is difficult in this model to protect the ACL graft from weight bearing loads. Bandaging and immobilization are not practical or effective in this animal model. The inability to concentrate the blood platelets limits the ability to discover whether increasing platelet count above that of whole blood would continue to enhance ACL graft healing and reduce postoperative laxity further. However, regardless of the limitations of the model, the data clearly demonstrates that the addition of platelets enhances graft healing and improves AP stability of the knee after ACL reconstruction at an early time point in the caprine model.

Example 7

Suture Techniques that Restore Normal AP Laxity of the Knee after ACL Transection The data described herein demonstrate suture techniques that go from femur to tibia can restore the normal AP laxity of the knee at time zero, particularly if they are tied in a small amount of flexion and the tibial attachment point is within the normal ACL footprint. As shown below, repair to the tibial stump of the ACL (Marshall technique) resulted in knees with over 5 mm greater AP laxity than knees with an intact ACL. Suture repair to bone using fixation points within the normal ACL footprint resulted in knee laxity within 0.5 mm of the knees with an intact ACL when the sutures were tied with the knee flexed at 60 degrees. Laxity increases of 1 to 3 mm were seen if the sutures were tied with the knee in 30 degrees of flexion or in more posterior tunnels.

Primary repair of the ACL was pioneered by John Marshall in the 1960's (Marshall J L, Warren R F, Wickiewicz T L, *Clin Orthop*. 1979; 143:97-106, Marshall J L, Warren R F, Wickiewicz T L. *Am J Sports Med*. 1982; 10:103-107.). Favor for this technique was lost due to the high re-rupture rate (Feagin J A, Jr., Curl W W. *Am J Sports Med*. 1976; 4(3):95-100.) and the limited improvement over nonsurgical treatment seen in patients undergoing primary repair (Engebretsen L, Benum P, Fasting O, Molster A, Strand T. *American Journal of Sports Medicine*. 1990; 18(6):585-590, Grontvedt T, Engebretsen L, Benum P, Fasting O, Molster A, Strand T. *Journal of Bone & Joint Surgery—American Volume*. 1996; 78(2):159-168.). However, recent discoveries by the inventor have suggested that amplifying the repair response of the torn ACL using a bioengineered scaffold to deliver growth factors into the wound site may result in functional healing of the severed ACL (Murray M M, Spindler K P, Devin C, et al. *J Orthop Res*. April 2006; 24(4):820-830, Murray M M, Spindler K P, Ballard P, Welch T P, Zurakowski D, Nanney L B. *J Orthop Res. Apr*. 5, 2007).

Since Marshall's work outlining his technique of primary repair, there has not been much interest or published work on comparison of suture techniques for primary repair of the ACL. This is in stark contrast to the numbers of papers published each year on ACL reconstruction technique, including papers on fixation types, tunnel placement and number of bundles to reconstruct. With the recent renewed interest in primary repair, additional work is needed to define the AP laxity of the knee after suture repair of the ACL using various techniques. Defining these surgical variables will allow for more accurate testing of new tissue engineered constructs in animal models, and also begin to define the most appropriate techniques for eventual human use.

In this study two hypotheses were tested. A first hypothesis was that suture repair could restore the normal AP laxity of the knee at time zero, and a second hypothesis was that the angle of flexion at which the sutures were tied would have a significant effect on the resultant AP laxity of the knee.

Materials and Methods

Six hindlimbs were retrieved from 30 kg female Yorkshire pigs at the time of euthanasia for other IACUC approved studies. The limbs were frozen until the time of testing (approximately 3 weeks). The limbs were thawed in warm water on the morning of testing. The knees were isolated by sectioning the femur just below the lesser trochanter and sectioning the tibia 2 cm above the ankle joint. The muscular attachments to tibia and femur were removed with care taken not to violate the knee joint capsule. All extra-capsular muscle was also removed. The femur and tibia had drywall screws placed at intervals along the bone (four screws in each bone) to assist with purchase in the potting material, then the bones were sequentially potted in 2" diameter polyvinyl chloride piping using Smooth-On casting material. Knees were wrapped in towels moistened with normal saline until testing.

Figure 24:
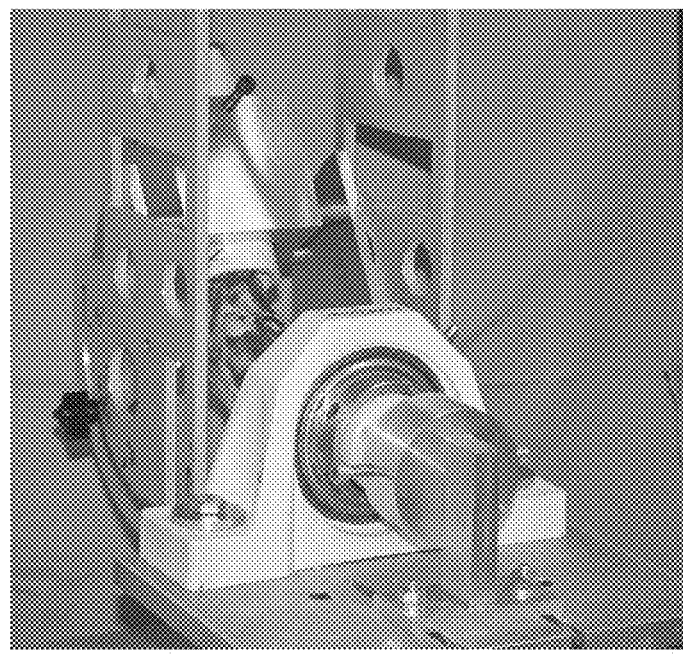
FIG. 24: AP laxity jig assembled in Instron Machine. The femoral shaft is secured in the upper fixture which can be rotated to place the knee between 0 and 90 degrees of flexion for testing. All testing in this experiment was performed with the knee at 60 degrees of flexion.
Figure 25:
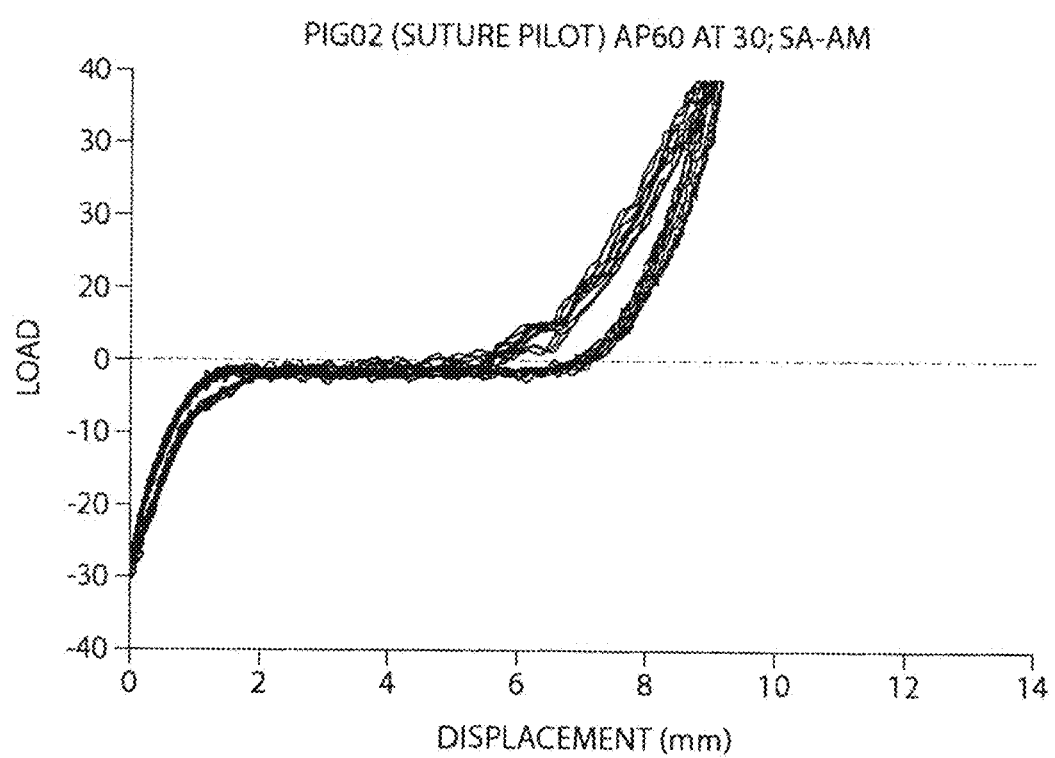
FIG. 25: Sample graph of the AP laxity testing load versus displacement data. This test was for the sutures tied through both the anterior and middle tunnels with the knee flexed 30 degrees. The resulting AP laxity is 8.7 mm, measured as the distance on the x axis between the two vertical regions of the curve.

The AP laxity testing was performed using a customized jig mounted on an Instron testing machine (FIG. 24). The femur was mounted in a movable fixture, which allowed for positioning the knee in 60 degrees of flexion. The pig knee extends only to 30 degrees short of full extension, thus the 60 degree position was thought to correspond to the 30 degree position in humans. A pilot study demonstrated that the 30 degree position was less sensitive to changes in AP laxity in the knee and therefore, only the 60 degree position was used in this study. Once the knee was positioned in the fixture, a cyclic load of 30N was applied to the femur. This resulted in an anterior femoral displacement at 30N followed by a posterior femoral displacement relative to the tibia to 30N. The magnitude of the displacements as load was applied was measured for each cycle at 100 Hz and plotted using Excel to give a load-displacement curve (FIG. 25).

Each of the six knees was tested in the intact state (INTACT). After that testing, dissection was performed to remove the patella and patellar tendon and expose the notch and the testing repeated (PAT DEFICIENT). The specimen was brought back to the dissection table and the ACL completely transected and testing repeated (ACL DEFICIENT).

Figure 26:
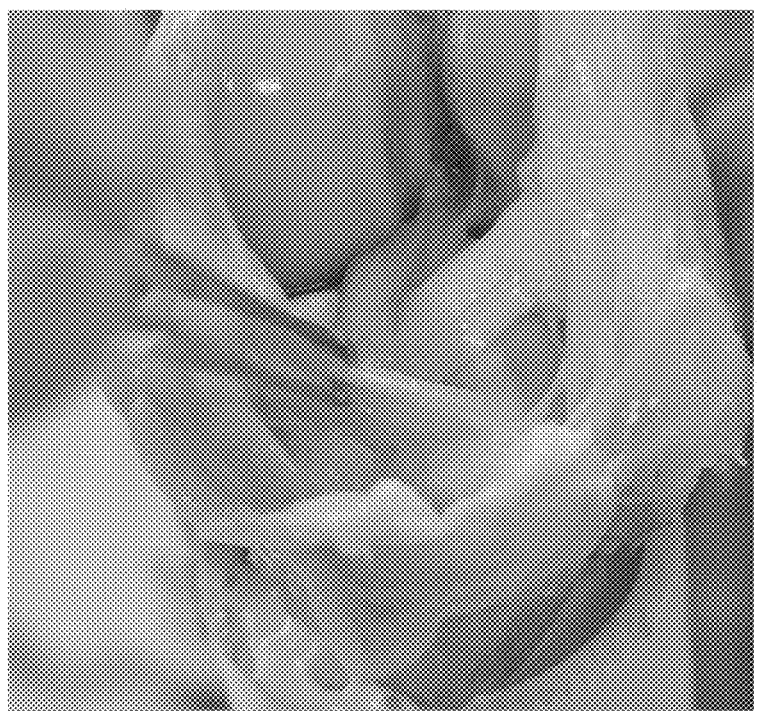
FIG. 26: Anatomy of the ACL insertion in the porcine knee. In the pig, there are two discrete tibial insertion sites of the ACL—one is posterolateral, behind the anterior horn attachment of the medial meniscus, and the second is anteromedial, located between the anterior horn attachment of the medial meniscus and the anterior horn attachment of the lateral meniscus (forceps are retracting the anterior horn attachment of the lateral meniscus).

The knees were then prepared for various primary repair techniques. First, a TwinFix 3.5 mm titanium anchor (Smith-Nephew, etc) was placed in the posterolateral notch of the femur, at the 11:00 position for the right knees and the 1:00 position for the left knees. This anchor had two Durabraid sutures passed through the anchor eyelet, resulting in four strands available for repair. These sutures were used for all tests. A four-stranded Marshall repair technique was performed by passing two looped #1 Vicryl sutures through the tibial stump at various depths and securing these four ends to the four ends of the Durabraid for a four-stranded Marshall repair. The sutures were first tied with the knee first in 30 degrees of flexion (MARSHALL 30) and then in 60 degrees of flexion (MARSHALL 60). The sutures were unknotted and the tibial stump of the ACL resected to reveal the tibial insertion sites. In the pig, there are two discrete tibial insertion sites of the ACL—one is posterolateral, behind the anterior horn attachment of the medial meniscus, and the second is anteromedial, located between the anterior horn attachment of the medial meniscus and the anterior horn attachment of the lateral meniscus (FIG. 26). A tibial aimer (ACUFEX) was used to place a 2.4 mm guide pin from the anteromedial border of the tibia up to each of these insertion sites. Care was taken to maintain a minimum of 5 mm between each of the drill sites on the anteromedial tibia. A third drill hole was made just medial to the apex of the lateral tibial spine. These tibial drill sites were labeled ANTERIOR for the insertion of the AM bundle, MIDDLE for the insertion of the PL bundle and POSTERIOR for the lateral tibial spine site. In four of the knees, drilling actually went through the potting material to get to the appropriate site.

AP laxity testing was then performed with sutures passed through the anterior, middle or posterior bone holes and tied over an endobutton. Sutures through each tunnel were tied in first 30 degrees of flexion and then 60 degrees of flexion and then underwent AP laxity testing at the 60 degree position. For example, each knee had all four sutures placed through the anterior tunnel and tied together over an endobutton with the knee at 30 degrees of flexion. This test was labeled (ANTERIOR 30). The sutures were then untied and re-tied with the knee in 60 degrees of flexion and the AP laxity of the knee measured (ANTERIOR 60). Sutures were then untied, passed through the middle tunnel, tied at 30 degrees and tested (MIDDLE 30), and so on. In addition to all four sutures going through the anterior, middle and posterior tunnels, a final position with two sutures going through the anterior tunnel and two sutures going through the middle tunnel was also tested (ANT-MID 30 and ANT-MID 60).

After each test, the knee was inspected to make sure the suture anchor was still secure and this was verified. There was no evidence of suture anchor pullout for any of the tests.

Statistical Analysis

Mixed model ANOVA with suture location and knee flexion angle as repeated measures terms and subject factors included to track individual specimens was used to determine the significance of differences between groups. A compound symmetry covariance structure (which demonstrated good fit based on Akaike's Information Criterion (AIC)) was selected.

Results

The intact knees had an AP laxity of 4.9 mm+/−0.4 mm (mean+/−SEM). Removal of the patella, patellar tendon, ligamentum mucosum and fat pad had a negligible effect on the AP laxity of the knee, with values for that group of 5.2+/−0.3 mm and t-testing p>0.79 for comparison between the two groups). When the ACL was sectioned, the laxity of the knee exceeded the maximum level set by the testing device (32 mm), and even at those displacements, no load was placed on the load cell. Therefore, this group was assigned a displacement of 32 mm.

Primary repair using the Marshall technique resulted in improved laxity in comparison with the ACL deficient knee, but increased AP laxity when compared to the intact and patellar deficient knee when the repair was done at both 30 degrees of flexion and at 60 degrees of flexion (Table 5). These differences between intact and Marshall technique ligament knee laxity were statistically significant at both 30 and 60 degrees (p<0.002 for both comparisons).

The AP laxity of the knee after suture repair was dependent on the location of the tibial suture (F=35; p<0.001). Sutures placed in the middle bone tunnel, located within the ACL tibial insertion site, restored AP laxity of the knee to values similar to that in the intact ACL knees with the patella removed (5.2+/−0.6 mm vs 5.2+/−0.4 mm, p>0.99; mean+/−SEM). Sutures placed in the anterior bone tunnel resulted in repairs with an average of 1.2 mm greater laxity than sutures placed in the middle location (6.4+/−0.4 mm), a difference which approached, but did not reach statistical significance in this multiple comparison model (p>0.05). Placement of the suture in a more posterior location on the tibial spine or in the ACL tibial remnant resulted in knees with significantly greater laxity than the knees with an intact ACL or knees repaired to anterior or middle tunnels (p<0.05 for all comparisons).

Figure 27A:
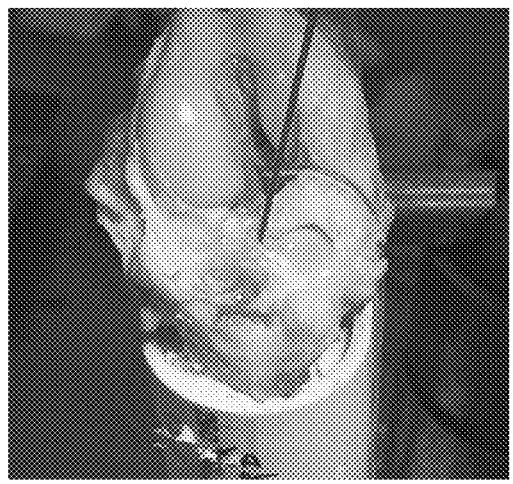
FIG. 27A, FIG. 27B and FIG. 27C: Photographs of the Anterior, Middle and Posterior tibial tunnel positions. The exit site of a Hewson suture passes through the three sites respectively.
Figure 27B:
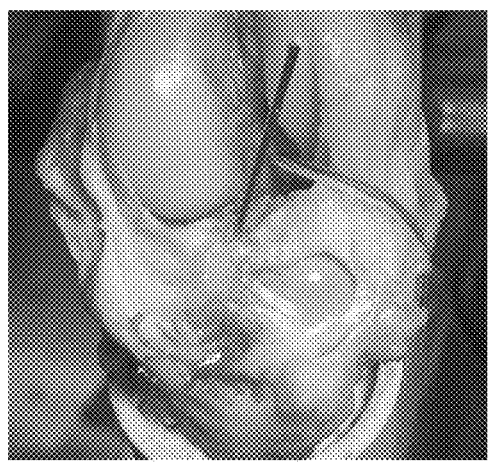
Figure 27C:
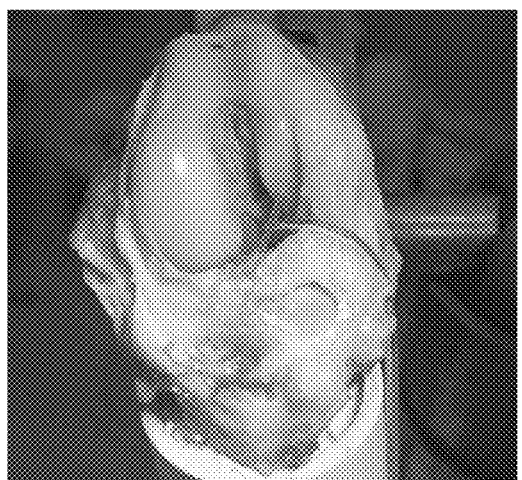
Figure 28:
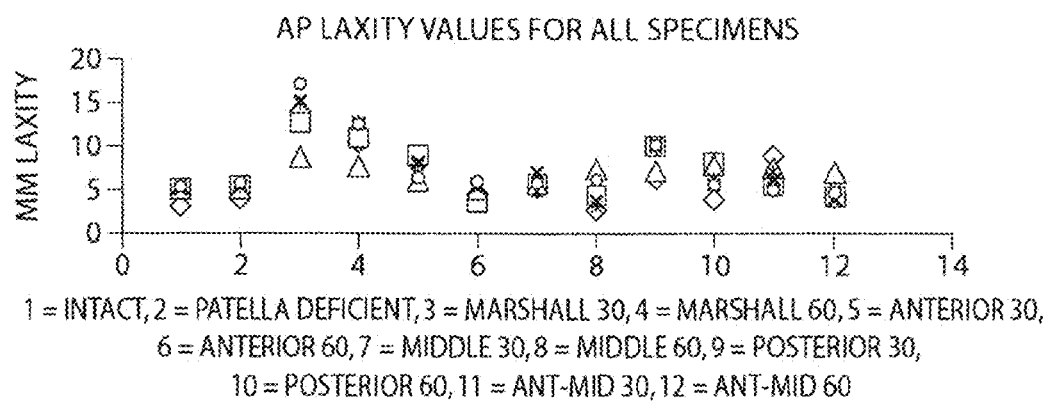
FIG. 28: Individual values for each of the six knees for the various testing positions. The intact knee laxity (column 1) is best restored in the groups where sutures passed through the anterior or middle tunnels and tied with the knee in 60 degrees of flexion (columns 6, 8 and 12).
Figure 29:
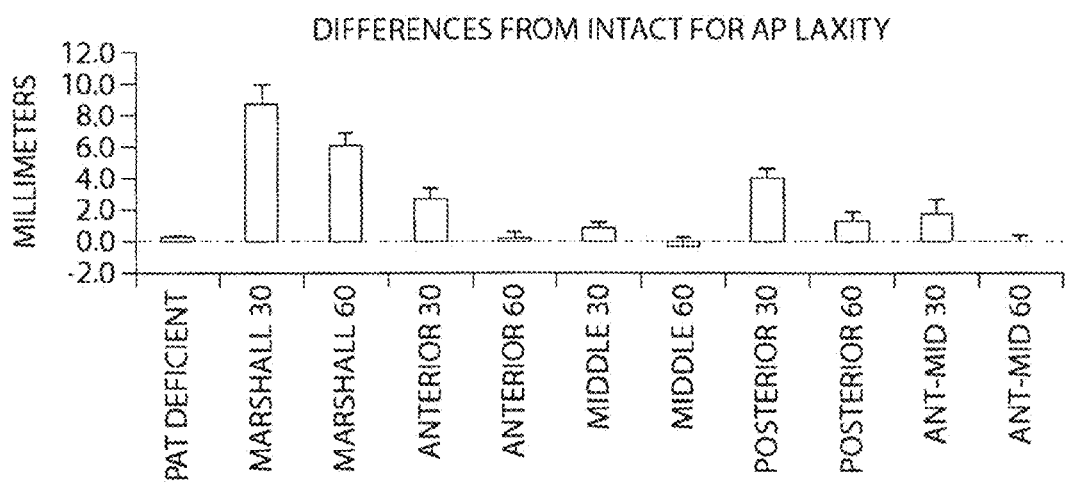
FIG. 29: Differences from the intact AP laxity of the knee for all repair conditions. Bars represent the mean, error bars represent the standard error of the mean. N=6 for all groups. Groups not significantly different from intact are marked by an asterisk.

FIGS. 27A-27C are photographs of the anterior (27A), middle (27B), and posterior (27C) tibial tunnel positions. FIG. 28 is a graph depicting AP laxity values for all specimens. FIG. 29 is a graph depicting differences from intact AP laxity values.

The AP laxity of the knee after suture repair was also dependent on the knee flexion angle when the sutures were tied (F=30, p<0.001). Laxity was greatest when the repairs were tied at 30 degrees of flexion, with less laxity noted when the repairs were tied at 60 degrees (p<0.001); however, the laxity in both groups remained higher than that of the ACL intact knees (p<0.02).

There was no interaction between tibial suture location and knee flexion angle (p=0.67).

Suture techniques that go from femur to tibia can restore the normal AP laxity of the knee at time zero, particularly if they are tied in a small amount of flexion and the tibial attachment point is within the normal ACL footprint. The data demonstrate that suture repair to the tibial stump, as in the Marshall technique, does not restore normal AP laxity of the knee, a finding which may be one of the reasons this technique of ACL repair resulted in a large percentage of patients having abnormal knee laxity post-operatively.

However, in several of the groups, there were some knees that had less AP laxity after suture repair than in the intact ACL condition. This could potentially result in overconstraining of the knee. Whether overconstraint or excess laxity are more likely to proceed to early degenerative joint changes is as yet unclear, but it is likely that repairs that result in large changes in knee laxity may not be ideal.

TABLE 5

AP laxity as a Function of Repair Type

| Location | Mean | Std. Error | df | 95% Confidence Interval | |
|---|---|---|---|---|---|
| | Lower Bound | Upper Bound | Lower Bound | Upper Bound | Lower Bound |
| Intact | 4.933(a) | 0.624 | 59.855 | 3.686 | 6.181 |
| Patellar Deficient | 5.200(a) | 0.624 | 59.855 | 3.952 | 6.448 |
| Marshall | 12.433(a)† | 0.444 | 52.094 | 11.542 | 13.325 |
| Anterior | 6.400(a) | 0.444 | 52.094 | 5.509 | 7.291 |
| Middle | 5.192(a) | 0.444 | 52.094 | 4.3 | 6.083 |
| Posterior | 7.658(a)‡ | 0.444 | 52.094 | 6.767 | 8.55 |
| Ant-Mid | 5.808(a) | 0.444 | 52.094 | 4.917 | 6.7 |

(a)Based on modified population marginal mean.
†Statistically different from the ACL intact knees (p < 0.002).
‡Statistically different from ACL intact knees (p < 0.05).

Example 8

Use of 40 Mend High Density Sponges (HDBC Sponges)

A study comparing the effectiveness of standard density collagen sponges (Gelfoam) and high density collagen sponges (HDBC) was performed. 1 cm diameter sponges of both Gelfoam and HDBC (3× increase in collagen concentration) were used as the scaffold.

The HDBC sponge was prepared by lyophilizing a collagen slurry and reconstituting it to a density of 40 mg/ml collagen. The slurry was neutralized and allowed to gel at 38° C. The resulting gels were then lyophilized. Both GELFOAM and HDBC sponges were seeded with cells suspended in platelet-rich plasma (PR or cells suspended in collagen slurry +PRP (concentration 1×10$^6$ cells/ml for both groups). Both cell solutions were allowed to absorb into the sponges for 30 min in the incubator, and then 2 drops of complete media was placed on top of the sponges to keep them moist overnight. After 12 hours, 1 ml of complete media was added to each well.

Results

Figure 30:
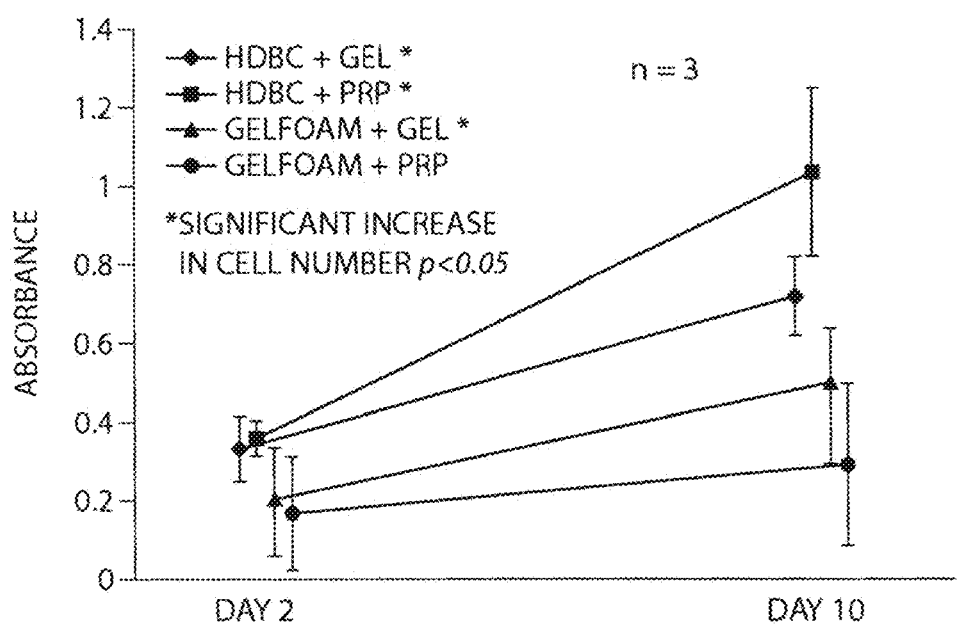
FIG. 30 is a graph depicting cell counts within the sponge/PRP preparations measured at Day 2 and Day 10.

The standard density sponges (GELFOAM) did not absorb the PRP or collagen slurry very efficiently. Cell counts within the sponges were measured at Day 2 and Day 10 (FIG. 30). The greatest cell proliferation occurred in the HDBC+PRP group and the least proliferation in the Gelfoam+PRP group.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention. Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety.

I claim:

1. A composition comprising
a sterile solution of solubilized collagen in a concentration of greater than 5 and less than or equal to 50 mg/ml and having a viscosity of 1,000-200,000 centipoise, a buffer wherein the composition has an osmolarity of 280-350 mOs/kg, wherein the composition is free of crosslinking agent.

2. The composition of claim 1, wherein the solution is a liquid or gel.

3. The composition of claim 1, wherein the solubilized collagen is present in a concentration of greater than 15 mg/ml and less than or equal to 40 mg/ml.

4. The composition of claim 1, further comprising a platelet, white blood cells, an antibiotic, an anti-plasmin agent, insoluble collagen, a plasminogen activator inhibitor, a glycosaminoglycan, decorin or biglycan.

5. The composition of claim 1, wherein the composition has a pH of 6.8-8.0.

6. The composition of claim 1, wherein the collagen is enzyme solubilized collagen or atelocollagen.

7. The composition of claim 1, wherein the solution is maintained at a temperature of 4° C.

8. A quick set composition comprising
a sterile solution of solubilized collagen in a concentration of greater than 5 and less than or equal to 50 mg/ml and having a viscosity of 1,000-200,000 centipoises and a pH of 6.8-8.0, wherein the solution has an osmolarity of 280-350 mOs/kg, wherein the solution sets into a scaffold within 10 minutes of exposure to temperatures of greater than 30° C.

9. A compressible expandable scaffold, comprising a collagen sponge, wherein the collagen is type I soluble collagen and collagen is in a concentration of grater than 5 and less than or equal to 50 mg/ml, wherein the collagen sponge is free of crosslinking agent.

* * * * *

UNITED STATES PATENT AND TRADEMARK OFFICE
CERTIFICATE OF CORRECTION

PATENT NO. : 9,849,213 B2
APPLICATION NO. : 15/082235
DATED : December 26, 2017
INVENTOR(S) : Martha M. Murray It is certified that error appears in the above-identified patent and that said Letters Patent is hereby corrected as shown below:

In the Claims

At Column 50, Line 54, Claim 9, "grater" should read --greater--.

Signed and Sealed this
Twenty-ninth Day of May, 2018

Andrei Iancu
*Director of the United States Patent and Trademark Office*